United States Patent
Pinchman et al.

(10) Patent No.: US 10,793,504 B2
(45) Date of Patent: Oct. 6, 2020

(54) METHODS FOR CROSS COUPLING

(71) Applicant: Recurium IP Holdings, LLC, San Diego, CA (US)

(72) Inventors: Joseph Robert Pinchman, San Diego, CA (US); Chad Daniel Hopkins, San Diego, CA (US); Kevin Duane Bunker, Escondido, CA (US); Peter Qinhua Huang, San Diego, CA (US)

(73) Assignee: Recurium IP Holdings, LLC, San Diego, CA (US)

( * ) Notice: Subject to any disclaimer, the term of this patent is extended or adjusted under 35 U.S.C. 154(b) by 0 days.

(21) Appl. No.: 16/326,909

(22) PCT Filed: Aug. 22, 2017

(86) PCT No.: PCT/US2017/048021
§ 371 (c)(1),
(2) Date: Feb. 20, 2019

(87) PCT Pub. No.: WO2018/039232
PCT Pub. Date: Mar. 1, 2018

(65) Prior Publication Data
US 2019/0202769 A1  Jul. 4, 2019

Related U.S. Application Data

(60) Provisional application No. 62/378,453, filed on Aug. 23, 2016.

(51) Int. Cl.
*C07C 67/343* (2006.01)
*C07D 263/56* (2006.01)
*C07D 239/26* (2006.01)
*C07D 413/08* (2006.01)
*C07D 213/26* (2006.01)
*C07F 5/02* (2006.01)
*B01J 31/22* (2006.01)

(52) U.S. Cl.
CPC .............. *C07C 67/343* (2013.01); *B01J 31/22* (2013.01); *C07D 213/26* (2013.01); *C07D 239/26* (2013.01); *C07D 263/56* (2013.01); *C07D 413/08* (2013.01); *C07F 5/02* (2013.01); *C07F 5/025* (2013.01); *B01J 2531/821* (2013.01); *B01J 2531/824* (2013.01); *B01J 2531/847* (2013.01); *C07C 2602/38* (2017.05)

(58) Field of Classification Search
CPC . C07C 67/343; C07C 69/753; C07C 2602/38; B01J 2531/821; B01J 2531/824; B01J 2531/847; B01J 31/22; B01J 2231/42; B01J 31/1616; C07D 213/26; C07D 239/26; C07D 263/56; C07D 413/08; C07F 5/02; C07F 5/025
See application file for complete search history.

(56) References Cited

U.S. PATENT DOCUMENTS 5,405,550 A    4/1995 Michl

FOREIGN PATENT DOCUMENTS

| EP | 0987238 | 3/2000 |
| WO | WO 2015/089170 | 6/2015 |
| WO | WO 2015/134710 | 9/2015 |
| WO | WO 2017/157932 | 9/2017 |

OTHER PUBLICATIONS

Is Levin et al. (Bicyclo[1.1.1]pentanes, [n]Staffanes, [1.1.1]Propellanes, and Tricyclo[2.1.0.02,5]pentanes, Chem. Rev., 100, pp. 169-234, published 2000) (Year: 2000).*
Mazal et al. (Symmetric Bridgehead-to-Bridgehead Coupling of Bicyclo[1.1.1]pentanes and [n]Staffanes, J. Org. Chem., 63, pp. 2116-2119, Published 1998) (Year: 1998).*
Adhikary, A. et al., "Nickel-Catalyzed Cross-Coupling Reactions" Pincer and Pincer-Type Complexes (2014), 117-147.
Albrecht et al., "Platinum Group Organometallics Based on "Pincer" Complexes: Sensors, Switches, and Catalysts" Angew. Chem. Int Ed. (2001) 40(20): 3750-3781.
Aldrich ChemFiles "Nájera Catalysts" (2007) 7.5, 6.
Atack, et al., "Manganese-Catalyzed Borylation of Unactivated Alkyl Chlorides" J. Am. Chem. Soc. (2016), 138 (19), 6139-6142.
Atack, et al., "Iron-Catalyzed Borylation of Alkyl Electrophiles" J. Am. Chem. Soc. (2014), 136 (27), 9521-9523.
Bruno et al., "Design and preparation of new palladium precatalysts for C—C and C—N cross-coupling reactions" Chem Sci. (2013) 4: 916-920.
Bruno et al., "New Palladium Precatalysts for Cross-Coupling Reactions" The Strem Chemiker (Jan. 2014) XXVII(1).:2-84.
Bunker et al., "Scalable Synthesis of 1-Bicyclo[1.1.1]pentylamine via a Hydrohydrazination Reaction" Org. Lett. (2011) 13(17):4746-4748.
De Meijere et al., "1,3-Bicyclo[1.1.1]pentanediyl: The Shortest Rigid Linear Connector of Phenylated Photochromic Units and a 1,5-Dimethoxy-9,10-di(phenylethynyl)anthracene Fluorophore" Chem. Eur. J. (2007) 13:2503-2516.
Han, Fu-She, "Transition-metal-catalyzed Suzuki-Miyaura cross-coupling reactions: a remarkable advance from palladium to nickel catalyst" Chem. Soc. Rev. (2013) 42:5270-5298.
Hartwig, J. F., "Organotransition Metal Chemistry—From Bonding to Catalysis" (University Science Books, Sausalito California) (2010) Table of Contents Only.

(Continued)

Primary Examiner — Yevgeny Valenrod
Assistant Examiner — Blaine G Doletski
(74) Attorney, Agent, or Firm — Knobbe Martens Olson & Bear LLP

(57) ABSTRACT

Methods of preparing substituted bicyclo[0.1.1.1]pentane compounds of Formula (I) comprise reacting a compound of Formula (A) with a compound of Formula (B) in the presence of a first transition metal catalyst selected from a palladium catalyst and a nickel catalyst, where the variables $R^1$, $R^2$, $X^1$ and $X^2$ are as described herein.

22 Claims, 1 Drawing Sheet

(56) References Cited

OTHER PUBLICATIONS

Larock, R.C., "Comprehensive Organic Transformations: A Guide to Functional Group Preparations" (2nd Ed., Wiley, John & Sons, Inc., Nov. 1999) Table of Contents Only.
Levin et al., "Bicyclo[1.1.1]pentanes, [n]Staffanes, [1.1.1]Propellanes, and Tricyclo[2.1.0.0$^{2,5}$]pentanes" (2000) *Chem. Rev.* 100:169-234.
Mazal et al., "Symmetric Bridgehead-to-Bridgehead Coupling of Bicyclo[1.1.1]pentanes and [n]Staffanes" J. Org. Chem. (1998) 63(7):2116-2119.
March, J., Advanced Organic Chemistry: Reactions, Mechanisms, and Structure (6th Ed., Wiley, John & Sons, Inc., Jan. 2007) Table of Contents Only.
Messner et al., "Nickel- and Palladium-Catalyzed Cross-Coupling Reactions at the Bridgehead of Bicyclo[1.1.1]pentane Derivatives—A Convenient Access to Liquid Crystalline Compounds Containing Bicyclo[1.1.1]pentane Moieties" Eur. J. Org. Chem. (2000) 7:1137-1155.
Metal-Catalyzed Cross coupling Reactions and More (Armin de Meijere et al., ed. Wiley-VCH) (2014) Table of Contents Only.
Miyaura et al., "Palladium-Catalyzed Cross-Coupling Reactions of Organoboron Compounds" Chem. Rev. (1995) 95, 2457-2483.
Negishi et al., "Palladium-Catalyzed Alkenylation by the Negishi Coupling" Aldrichim. Acta, (2005) 38(3), 71-88.
Noble et al., "Merging Photoredox and Nickel Catalysis: Decarboxylative Cross-Coupling of Carboxylic Acids with Vinyl Halides" J. Am. Chem. Soc. (2015) 137(2):624-627.
Phan et al., "On the Nature of the Active Species in Palladium Catalyzed Mizoroki-Heck and Suzuki-Miyaura Couplings—Homogeneous or Heterogeneous Catalysis, A Critical Review" Advanced Synthesis & Catalysis (2006) 348(6):609-679.
Prier et al., "Visible Light Photoredox Catalysis with Transition Metal Complexes: Applications in Organic Synthesis" Chem. Rev., (2013) 113:5322-5363.
Selander et al., "Catalysis by Palladium Pincer Complexes" Chem. Rev. (2011) 111:2048-2076.
Sommer, W., Aldrich ChemFiles (2007) 7.10, 17.
Takahashi, et al., "Chapter 2. Nickel-catalyzed Cross-coupling Reactions" Modern Organonickel Chemistry (2005), Table of Contents and 41-55.
Toriyama et al., "Redox-Active Esters in Fe-catalyzed C—C Coupling" J. Am. Chem. Soc. (2016) 138(35): 11132-11135.
Zuo et al., "Merging photoredox with nickel catalysis: Coupling of a-carboxyl sp$^3$-carbons with aryl halides" Science (2014) 345(6195):437-440.
International Search Report and Written Opinion dated Nov. 13, 2017 for PCT Application No. PCT/US2017/048021, filed Aug. 22, 2017.
International Preliminary Report on Patentability dated Mar. 7, 2019 for PCT Application No. PCT/US2017/048021, filed Aug. 22, 2017.
Examination Report dated Mar. 12, 2020 for New Zealand Application No. 750265, filed Aug. 22, 2017.
Extended European Search Report dated Mar. 3, 2020 for EP Application No. 17844283.6, filed Aug. 22, 2017.

\* cited by examiner

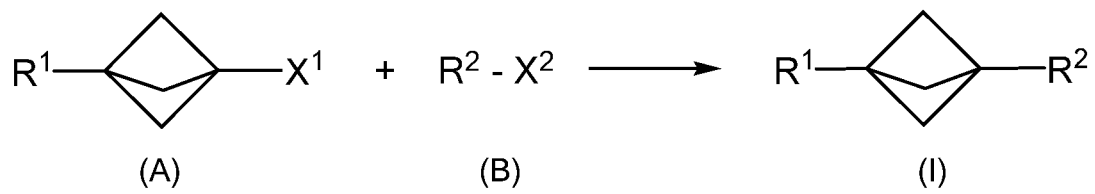

METHODS FOR CROSS COUPLING

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR 1.57.

FIELD

The present application relates to processes for transition metal catalyzed couplings of substituted bicyclo[1.1.1]pentanes to functionalized organic molecules, conditions for carrying out such couplings, and products resulting therefrom.

DESCRIPTION

A number of conditions have been demonstrated for transition metal catalyzed coupling of organic moieties. These reactions fall into the broad categories of cross coupling and homocoupling. In a cross coupling reaction, the two coupling partners are different, while in a homocoupling reaction the two are the same. Cross coupling is of particular interest because the diversity of possible reaction products is greater than from homocoupling. The organic moieties that react with one another are often components of two separate molecules, however, intramolecular reactions, i.e., those in which the two moieties are present in a single molecule, are also known.

Generally, it is believed that coupling reactions proceed by the breaking of a carbon-heteroatom bond to form a transition metal-containing organometallic moiety; transmetallation of the organometallic moiety to form a second, transient, organometallic moiety; and formation of the final carbon-carbon bond along with release of a ligated metal. These coupling reactions are generally classified in terms of the identity of the initially formed organometallic moiety, which includes a bond between a carbon atom and a metal or semi-metal atom. For example, when the initially formed organometallic moiety includes boron, the coupling reaction is typically classified as a Suzuki coupling reaction (see Miyaura et al., Chem. Rev. (1995) vol. 95, 2457-2483; Han, Chem. Soc. Rev. (2013) Vol. 42, 5270-5298). When the initially formed organometallic moiety includes zinc, the reaction is typically classified as a Negishi coupling reaction (see Negishi et al., Aldrichim. Acta, (2005) Vol. 38(3), 71-87). Other types of cross coupling reactions are recognized, including those associated with Stille (organotin), Kumada (organomagnesium halide) and Hiyama (organosilicon).

More recently, coupling reactions have been demonstrated in which a transition metal organometallic group couples with a carbon atom carrying a reduction-oxidation ("redox") labile group. (see Prier et al., Chem. Rev., (2013) Vol. 113, 5322-5363). This type of coupling has not been demonstrated to be applicable to broad range of substrates. Further, where this coupling has been demonstrated to form a bond with an $sp^3$ carbon atom, a neighboring heteroatom has been required (see Zuo et al., Science (2014) Vol. 345, Issue 6195, 437-440). In addition, tertiary alkyl carboxylic acids have not been regarded as viable coupling partners (see Noble et al., J. Am. Chem. Soc. (2015), Vol. 137 (2), 624-627). Compounds having redox labile moieties have been coupled with aryl organozinc and aryl organomagnesium species using iron catalysis (see Toriyama, F., et al., Redox-Active Esters in Fe-catalyzed C—C Coupling, J. Am. Chem. Soc., Publication Date (Web): 22 Aug. 2016).

Each of these coupling methods is generally limited to bond formation between two $sp^2$ carbon atoms. Although some coupling reactions in which a bond to an $sp^3$ carbon atom is formed have been demonstrated, such reactions have limited scope. Furthermore, cross coupling reactions have not been used to successfully create a wide variety of substituted bicyclo[1.1.1]pentanes.

SUMMARY

Various embodiments provide methods of preparing a substituted bicyclo[1.1.1]pentane compound of Formula (I), comprising reacting a compound of Formula (A) with a compound of Formula (B) in the presence of a first transition metal catalyst as illustrated in FIG. 1 and the following:

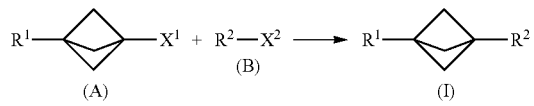

In an embodiment, the bond between $R^2$ and the bicyclo[1.1.1]pentane in the compound of Formula (I) is a carbon-carbon bond. In an embodiment, at least one of $X^1$ and $X^2$ is not a boron-containing moiety.

An embodiment provides a method for preparing a substituted bicyclo[1.1.1]pentane compound of Formula (I), can include: reacting a compound of Formula (A) with a compound of Formula (B) in the presence of a first transition metal catalyst, optionally a second transition metal catalyst, and optionally a base, under conditions selected to form a compound of Formula (I).

In an embodiment, $R^1$ in Formula (A) and Formula (I) can be selected from hydrogen, an optionally substituted $C_{1-30}$ alkyl, an optionally substituted $C_{2-30}$ alkenyl, an optionally substituted $C_{3-10}$ monocyclic cycloalkyl, an optionally substituted aryl, an optionally substituted heteroaryl, an optionally substituted heterocyclyl, a halogen, an optionally substituted C-carboxy, an amino, a mono-substituted amino, a di-substituted amino, an optionally substituted C-amido, an optionally substituted N-amido, an optionally substituted $C_{1-30}$ alkoxy, a hydroxy, an optionally substituted $C_{1-30}$ haloalkyl, a cyano, an optionally substituted S-sulfonamido, an optionally substituted N-sulfonamido, an optionally substituted O-carboxy, an optionally substituted $C_{2-30}$ alkynyl, an optionally substituted $C_{3-10}$ cycloalkenyl, an optionally substituted aryl(alkyl), an optionally substituted heteroaryl(alkyl), an optionally substituted heterocyclyl(alkyl), an optionally substituted acyl, an optionally substituted thiocarbonyl, an optionally substituted O-carbamyl, an optionally substituted N-carbamyl, an optionally substituted O-thiocarbamyl, an optionally substituted N-thiocarbamyl, an optionally substituted C-thioamido, an optionally substituted N-thioamido, an optionally substituted sulfenyl, an optionally substituted sulfinyl, an optionally substituted sulfonyl, an optionally substituted haloalkoxy, and a first boron-containing moiety, wherein the first boron-containing moiety is connected by the boron. In an embodiment, the first boron-containing moiety can be selected from an organoborane, a boronic ester, a boronic acid, a trifluoroborate salt, an N-coordinated boronate, a boronate and a boronamide.

In an embodiment, $X^1$ in Formula (A) can be selected from a halide, a pseudohalide, a —C(=O)Y, and a second boron-containing moiety. In an embodiment, the second boron-containing moiety can be selected from an organoborane, a boronic ester, a boronic acid, a trifluoroborate salt, an N-coordinated boronate, a boronate and a boronamide, wherein the second boron-containing moiety is connected by the boron.

In an embodiment, the compound of Formula (B) can have the structure $R^2$—$X^2$. In an embodiment, $R^2$ in Formula (B) and Formula (I) can be selected from an optionally substituted $C_{1-30}$ alkyl, an optionally substituted $C_{2-30}$ alkenyl, an optionally substituted $C_{3-10}$ cycloalkyl, an optionally substituted $C_{3-10}$ cycloalkenyl, an optionally substituted aryl, an optionally substituted heteroaryl and an optionally substituted heterocyclyl. In an embodiment, $X^2$ in Formula (B) can be selected from a halide, a pseudohalide, a —C(=O)Y, a zinc halide, a zinc pseudohalide and a third boron-containing moiety selected from an organoborane, a boronic ester, a boronic acid, a trifluoroborate salt, an N-coordinated boronate, a boronate and a boronamide.

In an embodiment, the reacting of the compound of Formula (A) with the compound of Formula (B) can be conducted in the presence of a first transition metal catalyst. In an embodiment, the first transition metal catalyst can be selected from a Pd catalyst and a Ni catalyst.

In an embodiment, the reacting of the compound of Formula (A) with the compound of Formula (B) can be conducted in the presence of the first transition metal catalyst and, optionally, a second transition metal catalyst. In an embodiment, the second transition metal catalyst can be selected from an Ir catalyst, a Cu catalyst and an Ru catalyst. In an embodiment, when the second transition metal catalyst is present, either $X^1$ in Formula (A) or $X^2$ in Formula (B) can be a —C(=O)Y.

In an embodiment in which $X^1$ in Formula (A) and/or $X^2$ in Formula (B) can be a —C(=O)Y, each Y can be independently selected from a halide, an optionally substituted heterocyclyl, an optionally substituted heteroaryl, $SR^6$, $OR^6$, SM and OM. In an embodiment, each $R^6$ can be independently selected from hydrogen, an optionally substituted $C_{1-30}$ alkyl, an optionally substituted $C_{2-30}$ alkenyl, an optionally substituted $C_{3-30}$ cycloalkyl, an optionally substituted heterocyclyl, an optionally substituted heteroaryl, and an optionally substituted aryl. In an embodiment, each M can be independently selected from a monovalent cation and a divalent cation.

These and other embodiments are described in greater detail below.

DRAWINGS

The FIGURE illustrates General Scheme 1 for preparing compounds of Formula (I).

DETAILED DESCRIPTION

Definitions

Unless defined otherwise, all technical and scientific terms used herein have the same meaning as is commonly understood by one of ordinary skill in the art. All patents, applications, published applications and other publications referenced herein are incorporated by reference in their entirety unless stated otherwise. In the event that there are a plurality of definitions for a term herein, those in this section prevail unless stated otherwise.

Whenever a group is described as being "optionally substituted" that group may be unsubstituted or substituted with one or more of the indicated substituents. Likewise, when a group is described as being "unsubstituted or substituted" if substituted, the substituent(s) may be selected from one or more of the indicated substituents. If no substituents are indicated, it is meant that the indicated "optionally substituted" or "substituted" group may be substituted with one or more group(s) individually and independently selected from D (deuterium), halogen, hydroxy, $C_{1-4}$ alkoxy, $C_{1-4}$ alkyl, $C_{3-10}$ cycloalkyl, aryl, heteroaryl, $C_{1-6}$ haloalkyl, cyano, alkenyl, alkynyl, $C_{3-10}$ cycloalkenyl, aryl(alkyl), heteroaryl(alkyl), heterocyclyl(alkyl), acyl, thiocarbonyl, O-carbamyl, N-carbamyl, O-thiocarbamyl, N-thiocarbamyl, C-amido, N-amido, C-thioamido, N-thioamido, S-sulfonamido, N-sulfonamido, C-carboxy, O-carboxy, sulfenyl, sulfinyl, sulfonyl, haloalkoxy, an amino, a mono-substituted amino group and a di-substituted amino group.

As used herein, "$C_a$ to $C_b$" in which "a" and "b" are integers refer to the number of carbon atoms in a group. The indicated group can contain from "a" to "b", inclusive, carbon atoms. Thus, for example, a "$C_1$ to $C_4$ alkyl" group refers to all alkyl groups having from 1 to 4 carbons, that is, $CH_3$—, $CH_3CH_2$—, $CH_3CH_2CH_2$—, $(CH_3)_2CH$—, $CH_3CH_2CH_2CH_2$—, $CH_3CH_2CH(CH_3)$— and $(CH_3)_3C$—. If no "a" and "b" are designated, the broadest range described in these definitions is to be assumed.

If two "R" groups are described as being "taken together" the R groups and the atoms they are attached to can form a cycloalkyl, cycloalkenyl, aryl, heteroaryl or heterocycle. For example, without limitation, if $R^a$ and $R^b$ of an $NR^aR^b$ group are indicated to be "taken together," it means that they are covalently bonded, either indirectly through intermediate atoms, or directly to one another, to form a ring, for example:

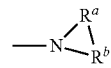

As used herein, the term "alkyl" refers to a fully saturated aliphatic hydrocarbon group. The alkyl moiety may be branched or straight chain. Examples of branched alkyl groups include, but are not limited to, iso-propyl, sec-butyl, t-butyl and the like. Examples of straight chain alkyl groups include, but are not limited to, methyl, ethyl, n-propyl, n-butyl, n-pentyl, n-hexyl, n-heptyl and the like. The alkyl group may have 1 to 30 carbon atoms (whenever it appears herein, a numerical range such as "1 to 30" refers to each integer in the given range; e.g., "1 to 30 carbon atoms" means that the alkyl group may consist of 1 carbon atom, 2 carbon atoms, 3 carbon atoms, etc., up to and including 30 carbon atoms, although the present definition also covers the occurrence of the term "alkyl" where no numerical range is designated). The alkyl group may also be a medium size alkyl having 1 to 12 carbon atoms. The alkyl group could also be a lower alkyl having 1 to 6 carbon atoms. An alkyl group may be substituted or unsubstituted.

The term "alkenyl" used herein refers to a monovalent straight or branched chain hydrocarbon group containing one or more carbon-carbon double bonds. The alkenyl group may have 2 to 30 carbon atoms, 2 to 12 carbon atoms or 2 to 6 carbon atoms. Examples of an alkenyl include, but are not limited to, 1-propenyl, 2-propenyl, 2-methyl-1-propenyl, 1-butenyl, 2-butenyl and the like. An alkenyl group may be unsubstituted or substituted.

The term "alkynyl" used herein refers to a monovalent straight or branched chain hydrocarbon group containing one or more carbon-carbon triple bonds. The alkynyl group may have 2 to 30 carbon atoms, 2 to 12 carbon atoms or 2 to 6 carbon atoms. Examples of an alkynyl include, but not limited to, 1-propynyl, 1-butynyl, 2-butynyl and the like. An alkynyl group may be unsubstituted or substituted.

As used herein, "cycloalkyl" refers to a completely saturated (no double or triple bonds) mono- or multi-cyclic hydrocarbon ring system. When composed of two or more rings, the rings may be joined together in a fused, bridged or spiro fashion. Cycloalkyl groups can contain 3 to 30 atoms in the ring(s), 3 to 20 atoms in the ring(s), 3 to 10 atoms in the ring(s), 3 to 8 atoms in the ring(s) or 3 to 6 atoms in the ring(s). A cycloalkyl group may be unsubstituted or substituted.

As used herein, the term "fused" refers to a connectivity between two rings in which two adjacent atoms sharing at least one bond (saturated or unsaturated) are common to the rings. For example, in the following structure, rings A and B are fused

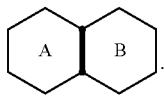

Examples of fused ring structures include, but are not limited to, decahydronaphthalene, 1H-indole, quinolone, chromane, bicyclo[2.1.0]pentane and 6,7,8,9-tetrahydro-5H-benzo[7]annulene.

As used herein, the term "bridged" refers to a connectivity wherein three or more atoms are shared between two rings. The following structures:

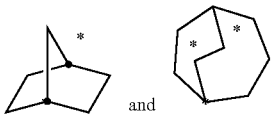 [SMILES: C1C[C@H]2CC[C@H]1C2 ; C1CC2CCC(C1)CC2]

are examples of "bridged" rings because the indicated atoms are shared between at least two rings. Examples of bridged ring structures include, but are not limited to, bicyclo[1.1.1]pentane, 2-oxabicyclo[1.1.1]pentane, 5-azabicyclo[2.1.1]hexane, 6-azabicyclo[3.1.1]heptane, adamantane and norbornane.

As used herein, the term "spiro" refers to a connectivity between two rings wherein the rings have only one atom in common. For example, in the structure

rings C and D are joined by a spiro connection. Examples of spiro connected ring structures include, but are not limited to, spiro[3.3]heptane, 2,6-diazaspiro[3.3]heptane, 2-oxa-6-azaspiro[3.3]heptane, spiro[4.5]decane and 2,6-dioxaspiro[3.3]heptane.

As used herein, "cycloalkenyl" refers to a mono- or multi-cyclic hydrocarbon ring system that contains one or more double bonds in at least one ring; although, if there is more than one, the double bonds cannot form a fully delocalized pi-electron system throughout all the rings (otherwise the group would be "aryl," as defined herein). Cycloalkenyl groups can contain 3 to 30 atoms in the ring(s), 3 to 20 atoms in the ring(s), 3 to 10 atoms in the ring(s), 3 to 8 atoms in the ring(s) or 3 to 6 atoms in the ring(s). When composed of two or more rings, the rings may be connected together in a fused, bridged or spiro fashion. A cycloalkenyl group may be unsubstituted or substituted.

As used herein, "cycloalkynyl" refers to a mono- or multi-cyclic hydrocarbon ring system that contains one or more triple bonds in at least one ring. If there is more than one triple bond, the triple bonds cannot form a fully delocalized pi-electron system throughout all the rings. Cycloalkynyl groups can contain 8 to 30 atoms in the ring(s), 8 to 20 atoms in the ring(s) or 8 to 10 atoms in the ring(s). When composed of two or more rings, the rings may be joined together in a fused, bridged or spiro fashion. A cycloalkynyl group may be unsubstituted or substituted.

As used herein, "aryl" refers to a carbocyclic (all carbon) monocyclic or multicyclic aromatic ring system (including fused ring systems where two carbocyclic rings share a chemical bond) that has a fully delocalized pi-electron system throughout all the rings. The number of carbon atoms in an aryl group can vary. For example, the aryl group can be a $C_6$-$C_{14}$ aryl group, a $C_6$-$C_{10}$ aryl group, or a $C_6$ aryl group. Examples of aryl groups include, but are not limited to, benzene, naphthalene and azulene. An aryl group may be substituted or unsubstituted.

As used herein, "heteroaryl" refers to a monocyclic, bicyclic and tricyclic aromatic ring system (a ring system with fully delocalized pi-electron system) that contain(s) one or more heteroatoms (for example, 1, 2, 3, 4 or 5 heteroatoms), that is, an element other than carbon, including but not limited to, nitrogen, oxygen and sulfur. A heteroaryl may be attached to the remainder of the molecule, and/or be substituted, through a carbon atom or a heteroatom such as a nitrogen atom. The number of atoms in the ring(s) of a heteroaryl group can vary. For example, the heteroaryl group can contain 4 to 14 atoms in the ring(s), 5 to 10 atoms in the ring(s) or 5 to 6 atoms in the ring(s). Furthermore, the term "heteroaryl" includes fused ring systems. Examples of heteroaryl rings include, but are not limited to, furan, furazan, thiophene, benzothiophene, phthalazine, pyrrole, oxazole, benzoxazole, 1,2,3-oxadiazole, 1,2,4-oxadiazole, thiazole, 1,2,3-thiadiazole, 1,2,4-thiadiazole, benzothiazole, imidazole, benzimidazole, indole, indazole, pyrazole, benzopyrazole, isoxazole, benzoisoxazole, isothiazole, triazole, benzotriazole, thiadiazole, tetrazole, pyridine, pyridazine, pyrimidine, pyrazine, purine, pteridine, quinoline, isoquinoline, quinazoline, quinoxaline, cinnoline and triazine. A heteroaryl group may be substituted or unsubstituted.

As used herein, "heterocyclyl" or "heteroalicyclyl" refers to three-, four-, five-, six-, seven-, eight-, nine-, ten-, up to 18-membered monocyclic, bicyclic and tricyclic ring system wherein carbon atoms together with from 1 to 5 heteroatoms constitute said ring system. A heterocycle may optionally contain one or more unsaturated bonds situated in such a way, however, that a fully delocalized pi-electron system does not occur throughout all the rings. The heteroatom(s) is an element other than carbon including, but not limited to, oxygen, sulfur and nitrogen. A heterocyclyl may be attached to the remainder of the molecule, and/or be substituted, through a carbon atom or a heteroatom such as a nitrogen atom. A heterocycle may further contain one or more carbonyl or thiocarbonyl functionalities, so as to make the definition include oxo-systems and thio-systems such as lactams, lactones, cyclic imides, cyclic thioimides and cyclic carbamates. When composed of two or more rings, the rings may be joined together in a fused, bridged, or spiro fashion. Additionally, any nitrogens in a heteroalicyclic may be quaternized. Heterocyclyl or heteroalicyclic groups may be unsubstituted or substituted. Examples of such "heterocyclyl" or "heteroalicyclyl" groups include, but are not limited to, 1,3-dioxin, 1,3-dioxane, 1,4-dioxane, 1,2-dioxolane, 1,3-dioxolane, 1,4-dioxolane, 1,3-oxathiane, 1,4-oxathiin, 1,3-oxathiolane, 1,3-dithiole, 1,3-dithiolane, 1,4-oxathiane, tetrahydro-1,4-thiazine, 2H-1,2-oxazine, maleimide, succinimide, barbituric acid, thiobarbituric acid, dioxopiperazine, hydantoin, dihydrouracil, trioxane, hexahydro-1,3,5-triazine, imidazoline, imidazolidine, isoxazoline, isoxazolidine, oxazoline, oxazolidine, oxazolidinone, thiazoline, thiazolidine, morpholine, oxirane, piperidine N-Oxide, piperidine, piperazine, pyrrolidine, pyrrolidone, pyrrolidione, 4-piperidone, pyrazoline, pyrazolidine, 2-oxopyrrolidine, tetrahydropyran, 4H-pyran, tetrahydrothiopyran, thiamorpholine, thiamorpholine sulfoxide, thiamorpholine sulfone and their benzo-fused analogs (e.g., benzimidazolidinone, tetrahydroquinoline and/or 3,4-methylenedioxyphenyl). Examples of bridged heterocyclic compounds include, but are not limited to, 1,4-diazabicyclo[2.2.2]octane and 1,4-diazabicyclo[3.1.1]heptane. Examples of spiro-connected heterocyclic compounds include, but are not limited to, 2-azaspiro[3.3]heptane, 2,6-diazaspiro[3.3]heptane, and 2-oxa-6-azaspiro[3.3]heptane.

As used herein, "aralkyl" and "aryl(alkyl)" refer to an aryl group connected, as a substituent, via a lower alkylene group. The lower alkylene and aryl group of an aralkyl may be substituted or unsubstituted. Examples include but are not limited to benzyl, 2-phenylalkyl, 3-phenylalkyl and naphthylalkyl.

As used herein, "heteroaralkyl" and "heteroaryl(alkyl)" refer to a heteroaryl group connected, as a substituent, via a lower alkylene group. The lower alkylene and heteroaryl group of heteroaralkyl may be substituted or unsubstituted. Examples include but are not limited to 2-thienylalkyl, 3-thienylalkyl, furylalkyl, thienylalkyl, pyrrolylalkyl, pyridylalkyl, isoxazolylalkyl and imidazolylalkyl and their benzo-fused analogs.

A "heteroalicyclyl(alkyl)" and "heterocyclyl(alkyl)" refer to a heterocyclic or a heteroalicyclylic group connected, as a substituent, via a lower alkylene group. The lower alkylene and heterocyclyl of a (heteroalicyclyl)alkyl may be substituted or unsubstituted. Examples include but are not limited tetrahydro-2H-pyran-4-yl(methyl), piperidin-4-yl(ethyl), piperidin-4-yl(propyl), tetrahydro-2H-thiopyran-4-yl (methyl) and 1,3-thiazinan-4-yl(methyl).

"Lower alkylene groups" are straight-chained —CH$_2$— tethering groups, forming bonds to connect molecular fragments via their terminal carbon atoms. Examples include but are not limited to methylene (—CH$_2$—), ethylene (—CH$_2$CH$_2$—), propylene (—CH$_2$CH$_2$CH$_2$—) and butylene (—CH$_2$CH$_2$CH$_2$CH$_2$—). A lower alkylene group can be substituted by replacing one or more hydrogen of the lower alkylene group and/or by substituting both hydrogens on the same carbon with a cycloalkyl group (e.g.,

).

As used herein, the term "hydroxy" refers to a —OH group.

As used herein, "alkoxy" refers to the formula —OR wherein R is an alkyl, an alkenyl, an alkynyl, a cycloalkyl, a cycloalkenyl, aryl, heteroaryl, heterocyclyl, cycloalkyl (alkyl), aryl(alkyl), heteroaryl(alkyl) or heterocyclyl(alkyl) is defined herein. A non-limiting list of alkoxys is methoxy, ethoxy, n-propoxy, 1-methylethoxy (isopropoxy), n-butoxy, iso-butoxy, sec-butoxy, tert-butoxy, phenoxy and benzoxy. An alkoxy may be substituted or unsubstituted.

As used herein, "acyl" refers to a hydrogen, alkyl, alkenyl, alkynyl, aryl, heteroaryl, heterocyclyl, aryl(alkyl), heteroaryl(alkyl) and heterocyclyl(alkyl) connected, as substituents, via a carbonyl group. Examples include formyl, acetyl, propanoyl, benzoyl and acryl. An acyl may be substituted or unsubstituted.

A "cyano" group refers to a "—CN" group.

The term "halogen atom" or "halogen" as used herein, means any one of the radio-stable atoms of column 7 of the Periodic Table of the Elements, such as, fluorine, chlorine, bromine and iodine.

A "thiocarbonyl" group refers to a "—C(=S)R" group in which R can be the same as defined with respect to O-carboxy. A thiocarbonyl may be substituted or unsubstituted.

An "O-carbamyl" group refers to a "—OC(=O)N (R$_A$R$_B$)" group in which R$_A$ and R$_B$ can be independently hydrogen, an alkyl, an alkenyl, an alkynyl, a cycloalkyl, a cycloalkenyl, aryl, heteroaryl, heterocyclyl, cycloalkyl(alkyl), aryl(alkyl), heteroaryl(alkyl) or heterocyclyl(alkyl). An O-carbamyl may be substituted or unsubstituted.

An "N-carbamyl" group refers to an "ROC(=O)N (R$_A$)—" group in which R and R$_A$ can be independently hydrogen, an alkyl, an alkenyl, an alkynyl, a cycloalkyl, a cycloalkenyl, aryl, heteroaryl, heterocyclyl, cycloalkyl(alkyl), aryl(alkyl), heteroaryl(alkyl) or heterocyclyl(alkyl). An N-carbamyl may be substituted or unsubstituted.

An "O-thiocarbamyl" group refers to a "—OC(=S)—N (R$_A$R$_B$)" group in which R$_A$ and R$_B$ can be independently hydrogen, an alkyl, an alkenyl, an alkynyl, a cycloalkyl, a cycloalkenyl, aryl, heteroaryl, heterocyclyl, cycloalkyl(alkyl), aryl(alkyl), heteroaryl(alkyl) or heterocyclyl(alkyl). An O-thiocarbamyl may be substituted or unsubstituted.

An "N-thiocarbamyl" group refers to an "ROC(=S)N (R$_A$)—" group in which R and R$_A$ can be independently hydrogen, an alkyl, an alkenyl, an alkynyl, a cycloalkyl, a cycloalkenyl, aryl, heteroaryl, heterocyclyl, cycloalkyl(alkyl), aryl(alkyl), heteroaryl(alkyl) or heterocyclyl(alkyl). An N-thiocarbamyl may be substituted or unsubstituted.

A "C-amido" group refers to a "—C(=O)N(R$_A$R$_B$)" group in which R$_A$ and R$_B$ can be independently hydrogen, an alkyl, an alkenyl, an alkynyl, a cycloalkyl, a cycloalkenyl, aryl, heteroaryl, heterocyclyl, cycloalkyl(alkyl), aryl(alkyl), heteroaryl(alkyl) or heterocyclyl(alkyl). A C-amido may be substituted or unsubstituted.

An "N-amido" group refers to a "RC(=O)N(R$_A$)—" group in which R and R$_A$ can be independently hydrogen, an alkyl, an alkenyl, an alkynyl, a cycloalkyl, a cycloalkenyl, aryl, heteroaryl, heterocyclyl, cycloalkyl(alkyl), aryl(alkyl), heteroaryl(alkyl) or heterocyclyl(alkyl). An N-amido may be substituted or unsubstituted.

A "C-thioamido" group refers to a "—C(=S)N(R$_A$R$_B$)" group in which R$_A$ and R$_B$ can be independently hydrogen, an alkyl, an alkenyl, an alkynyl, a cycloalkyl, a cycloalkenyl, aryl, heteroaryl, heterocyclyl, cycloalkyl(alkyl), aryl(alkyl), heteroaryl(alkyl) or heterocyclyl(alkyl). A C-thioamido may be substituted or unsubstituted.

An "N-thioamido" group refers to a "RC(=S)N($R_A$)—" group in which R and $R_A$ can be independently hydrogen, an alkyl, an alkenyl, an alkynyl, a cycloalkyl, a cycloalkenyl, aryl, heteroaryl, heterocyclyl, cycloalkyl(alkyl), aryl(alkyl), heteroaryl(alkyl) or heterocyclyl(alkyl). An N-thioamido may be substituted or unsubstituted.

An "S-sulfonamido" group refers to a "—$SO_2$N($R_A R_B$)" group in which $R_A$ and $R_B$ can be independently hydrogen, an alkyl, an alkenyl, an alkynyl, a cycloalkyl, a cycloalkenyl, aryl, heteroaryl, heterocyclyl, cycloalkyl(alkyl), aryl(alkyl), heteroaryl(alkyl) or heterocyclyl(alkyl). An S-sulfonamido may be substituted or unsubstituted.

An "N-sulfonamido" group refers to a "R$SO_2$N($R_A$)—" group in which R and $R_A$ can be independently hydrogen, an alkyl, an alkenyl, an alkynyl, a cycloalkyl, a cycloalkenyl, aryl, heteroaryl, heterocyclyl, cycloalkyl(alkyl), aryl(alkyl), heteroaryl(alkyl) or heterocyclyl(alkyl). An N-sulfonamido may be substituted or unsubstituted.

An "O-carboxy" group refers to a "RC(=O)O—" group in which R can be hydrogen, an alkyl, an alkenyl, an alkynyl, an alkoxy, a cycloalkyl, a cycloalkenyl, aryl, heteroaryl, heterocyclyl, cycloalkyl(alkyl), aryl(alkyl), heteroaryl(alkyl) or heterocyclyl(alkyl), as defined herein. An O-carboxy may be substituted or unsubstituted.

The terms "ester" and "C-carboxy" refer to a "—C(=O)OR" group in which R can be the same as defined with respect to O-carboxy. An ester and C-carboxy may be substituted or unsubstituted.

An "oxo" group refers to a "=O" group.

A "sulfenyl" group refers to an "—SR" group in which R can be hydrogen, an alkyl, an alkenyl, an alkynyl, a cycloalkyl, a cycloalkenyl, aryl, heteroaryl, heterocyclyl, cycloalkyl(alkyl), aryl(alkyl), heteroaryl(alkyl) or heterocyclyl(alkyl). A sulfenyl may be substituted or unsubstituted.

A "sulfinyl" group refers to an "—S(=O)—R" group in which R can be the same as defined with respect to sulfenyl. A sulfinyl may be substituted or unsubstituted.

A "sulfonyl" group refers to an "$SO_2$R" group in which R can be the same as defined with respect to sulfenyl. A sulfonyl may be substituted or unsubstituted.

As used herein, "haloalkyl" refers to an alkyl group in which one or more of the hydrogen atoms are replaced by a halogen (e.g., mono-haloalkyl, di-haloalkyl and tri-haloalkyl). Such groups include but are not limited to, chloromethyl, fluoromethyl, difluoromethyl, trifluoromethyl, 1-chloro-2-fluoromethyl and 2-fluoroisobutyl. A haloalkyl may be substituted or unsubstituted.

As used herein, "haloalkoxy" refers to an alkoxy group in which one or more of the hydrogen atoms are replaced by a halogen (e.g., mono-haloalkoxy, di-haloalkoxy and tri-haloalkoxy). Such groups include but are not limited to, chloromethoxy, fluoromethoxy, difluoromethoxy, trifluoromethoxy, 1-chloro-2-fluoromethoxy and 2-fluoroisobutoxy. A haloalkoxy may be substituted or unsubstituted.

The term "amino" as used herein refers to a —$NH_2$ group.

A "mono-substituted amino" group refers to a "—NHR" group in which R can be an alkyl, an alkenyl, an alkynyl, a haloalkyl, a cycloalkyl, a cycloalkenyl, aryl, heteroaryl, heterocyclyl, cycloalkyl(alkyl), aryl(alkyl), heteroaryl (alkyl) or heterocyclyl(alkyl), as defined herein. A mono-substituted amino may be substituted or unsubstituted. Examples of mono-substituted amino groups include, but are not limited to, —NH(methyl), —NH(phenyl) and the like.

A "di-substituted amino" group refers to a "—N$R_A R_B$" group in which $R_A$ and $R_B$ can be independently an alkyl, an alkenyl, an alkynyl, a haloalkyl, a cycloalkyl, a cycloalkenyl, aryl, heteroaryl, heterocyclyl, cycloalkyl(alkyl), aryl (alkyl), heteroaryl(alkyl) or heterocyclyl(alkyl), as defined herein. A di-substituted amino may be substituted or unsubstituted. Examples of di-substituted amino groups include, but are not limited to, —N(methyl)$_2$, —N(phenyl)(methyl), —N(ethyl)(methyl) and the like.

As used herein, "reacting" is a broad term that refers to the act of causing a chemical reaction by which the molecular and/or ionic structure of a substance and/or substances is rearranged. "Reacting" includes placing a molecule into an environment that results in a chemical transformation, and/or changing an environment around a molecule to result in a chemical transformation. Such acts of reacting include combining two or more molecules that chemically react with each other, either directly or through intermediate species. "Reacting" can also refer to causing chemical transformations of intermediate species arising from molecules that were placed in a particular environment.

As used herein, "ligand" is a broad term that refers to a molecule that is bound, or capable of binding, to an atom of a metal or semi-metal. A ligand may bind to a metal or semi-metal through bonding or non-bonding electrons. A ligand molecule can include a single atom or multiple atoms. A ligated metal or semi-metal is one that is coordinated by a ligand. Examples of ligands can be found in "Organotransition Metal Chemistry—From Bonding to Catalysis" John Hartwig (University Science Books, 2010).

A used herein, "pseudohalide" is a broad term that refers to a moiety capable of undergoing a reaction characteristic of a halide. For example, a pseudohalide can be a sulfonate, a phosphate, a cyanide, an azide, an isocyanate, a thioisocyanate, or a quaternary nitrogen moiety. When a pseudohalide is a sulfonate, it can be, for example, triflate, mesylate, tosylate, nitrophenyl sulfonate, bromophenyl sulfonate or benzene sulfonate.

Where the number of substituents is not specified (e.g. haloalkyl), there may be one or more substituents present. For example, "haloalkyl" may include one or more of the same or different halogens. As another example, "$C_1$-$C_3$ alkoxyphenyl" may include one or more of the same or different alkoxy groups containing one, two or three atoms.

As used herein, "free radical" refers to a species including an unpaired electron, or to an unpaired electron in such a species.

The term "pharmaceutically acceptable salt" refers to a salt of a compound that does not cause significant irritation to an organism to which it is administered and does not abrogate the biological activity and properties of the compound. In some embodiments, the salt is an acid addition salt of the compound. Pharmaceutical salts can be obtained by reacting a compound with inorganic acids such as hydrohalic acid (e.g., hydrochloric acid or hydrobromic acid), a sulfuric acid, a nitric acid and a phosphoric acid (such as 2,3-dihydroxypropyl dihydrogen phosphate). Pharmaceutical salts can also be obtained by reacting a compound with an organic acid such as aliphatic or aromatic carboxylic or sulfonic acids, for example formic, acetic, succinic, lactic, malic, tartaric, citric, ascorbic, nicotinic, methanesulfonic, ethanesulfonic, p-toluenesulfonic, trifluoroacetic, benzoic, salicylic, 2-oxopentanedioic, or naphthalenesulfonic acid. Pharmaceutical salts can also be obtained by reacting a compound with a base to form a salt such as an ammonium salt, an alkali metal salt, such as a sodium, a potassium or a lithium salt, an alkaline earth metal salt, such as a calcium or a magnesium salt, a salt of a carbonate, a salt of a bicarbonate, a salt of organic bases such as dicyclohexylamine, N-methyl-D-glucamine, tris(hydroxymethyl)methylamine, $C_1$-$C_7$ alkylamine, cyclohexylamine, triethanolamine, ethylenediamine, and salts with amino acids such as arginine and lysine. For compounds of Formula (I), those skilled in the art understand that when a salt is formed by protonation of a nitrogen-based group (for example, $NH_2$), the nitrogen-based group can be associated with a positive charge (for example, $NH_2$ can become $NH_3^+$) and the positive charge can be balanced by a negatively charged counterion (such as $Cl^-$).

It is understood that, in any compound described herein having one or more chiral centers, if an absolute stereochemistry is not expressly indicated, then each center may independently be of R-configuration or S-configuration or a mixture thereof. Thus, the compounds provided herein may be enantiomerically pure, enantiomerically enriched, racemic mixture, diastereomerically pure, diastereomerically enriched, or a stereoisomeric mixture. In addition it is understood that, in any compound described herein having one or more double bond(s) generating geometrical isomers that can be defined as E or Z, each double bond may independently be E or Z, or a mixture thereof.

It is understood that, in any compound described, all tautomeric forms are also intended to be included. For example, the following are tautomers:

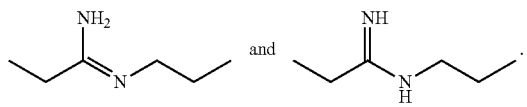

It is to be understood that where compounds disclosed herein have unfilled valencies, then the valencies are to be filled with hydrogens or isotopes thereof, e.g., hydrogen-1 (protium) and hydrogen-2 (deuterium).

It is understood that the compounds described herein can be labeled isotopically. Substitution with isotopes such as deuterium may afford certain therapeutic advantages resulting from greater metabolic stability, such as, for example, increased in vivo half-life or reduced dosage requirements. Each chemical element as represented in a compound structure may include any isotope of said element. For example, in a compound structure a hydrogen atom may be explicitly disclosed or understood to be present in the compound. At any position of the compound that a hydrogen atom may be present, the hydrogen atom can be any isotope of hydrogen, including but not limited to hydrogen-1 (protium) and hydrogen-2 (deuterium). Thus, reference herein to a compound encompasses all potential isotopic forms unless the context clearly dictates otherwise.

It is understood that the methods and combinations described herein include crystalline forms (also known as polymorphs, which include the different crystal packing arrangements of the same elemental composition of a compound), amorphous phases, salts, solvates, and hydrates. In some embodiments, the compounds described herein exist in solvated forms with pharmaceutically acceptable solvents such as water, ethanol, or the like. In other embodiments, the compounds described herein exist in unsolvated form. Solvates contain either stoichiometric or non-stoichiometric amounts of a solvent, and may be formed during the process of crystallization with pharmaceutically acceptable solvents such as water, ethanol, or the like. Hydrates are formed when the solvent is water, or alcoholates are formed when the solvent is alcohol. In addition, the compounds provided herein can exist in unsolvated as well as solvated forms. In general, the solvated forms are considered equivalent to the unsolvated forms for the purposes of the compounds and methods provided herein.

Where a range of values is provided, it is understood that the upper and lower limit, and each intervening value between the upper and lower limit of the range is encompassed within the embodiments.

Terms and phrases used in this application, and variations thereof, especially in the appended claims, unless otherwise expressly stated, should be construed as open ended as opposed to limiting. As examples of the foregoing, the term 'including' should be read to mean 'including, without limitation,' 'including but not limited to,' or the like; the term 'comprising' as used herein is synonymous with 'including,' 'containing,' or 'characterized by,' and is inclusive or open-ended and does not exclude additional, unrecited elements or method steps; the term 'having' should be interpreted as 'having at least;' the term 'includes' should be interpreted as 'includes but is not limited to;' the term 'example' is used to provide exemplary instances of the item in discussion, not an exhaustive or limiting list thereof; and use of terms like 'preferably,' 'preferred,' 'desired,' or 'desirable,' and words of similar meaning should not be understood as implying that certain features are critical, essential, or even important to the structure or function, but instead as merely intended to highlight alternative or additional features that may or may not be utilized in a particular embodiment. In addition, the term "comprising" is to be interpreted synonymously with the phrases "having at least" or "including at least". When used in the context of a process, the term "comprising" means that the process includes at least the recited steps, but may include additional steps. When used in the context of a compound, composition or device, the term "comprising" means that the compound, composition or device includes at least the recited features or components, but may also include additional features or components. Likewise, a group of items linked with the conjunction 'and' should not be read as requiring that each and every one of those items be present in the grouping, but rather should be read as 'and/or' unless the context indicates otherwise. Similarly, a group of items linked with the conjunction 'or' should not be read as requiring mutual exclusivity among that group, but rather should be read as 'and/or' unless the context indicates otherwise.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity. The indefinite article "a" or "an" does not exclude a plurality. A single processor or other unit may fulfill the functions of several items recited in the claims. The mere fact that certain measures are recited in mutually different dependent claims does not indicate that a combination of these measures cannot be used to advantage. Any reference signs in the claims should not be construed as limiting the scope.

As provided herein, a "coupling" is the formation of a sigma bond between two atoms, for example, between two carbon atoms. Each atom coupled is necessarily a constituent of a moiety, and each moiety is necessarily a constituent of a molecule. The moieties coupled may be constituents of a single molecule or of two different molecules.

As provided herein, a cross coupling catalyst is a transition metal complex (including one or more ligands) that can, under appropriate conditions, induce a coupling between two different moieties.

As provided herein, a photoredox catalyst is a transition metal complex (including one or more ligands) that can, under irradiation and in other appropriate conditions, generate a free radical by oxidizing or reducing a moiety.

Processes

Various embodiments provide a method for preparing a substituted bicyclo[1.1.1]pentane compound of Formula (I) having the following structure:

(I)

In an embodiment, the bond between $R^2$ and the bicyclo[1.1.1]pentane in the compound of Formula (I) is a carbon-carbon bond.

In an embodiment, a method for making the compound of Formula (I) includes reacting a compound of Formula (A) with a compound of Formula (B) as illustrated in FIG. 1. In an embodiment, the reaction of the compound of Formula (A) with the compound of Formula (B) is conducted in the presence of a first transition metal catalyst, optionally a second transition metal catalyst, and optionally a base, under conditions selected to form the compound of Formula (I). In an embodiment, the compound of Formula (B) can be $R^2$—$X^2$. In an embodiment, the compound of Formula (A) has the structure:

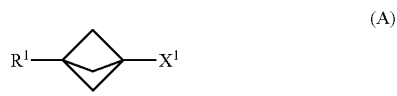

(A)

In various embodiments, the variable $R^1$ in the compounds of Formula (I) and/or Formula (A) can be hydrogen, an optionally substituted $C_{1-30}$ alkyl, an optionally substituted $C_{2-30}$ alkenyl, an optionally substituted $C_{3-10}$ monocyclic cycloalkyl, an optionally substituted aryl, an optionally substituted heteroaryl, an optionally substituted heterocyclyl, a halogen, an optionally substituted C-carboxy, an amino, a mono-substituted amino, a di-substituted amino, an optionally substituted C-amido, an optionally substituted N-amido, an optionally substituted $C_{1-30}$ alkoxy, a hydroxy, an optionally substituted $C_{1-30}$ haloalkyl, a cyano, an optionally substituted S-sulfonamido, an optionally substituted N-sulfonamido, an optionally substituted O-carboxy, an optionally substituted $C_{2-30}$ alkynyl, an optionally substituted $C_{3-10}$ cycloalkenyl, an optionally substituted aryl(alkyl), an optionally substituted heteroaryl(alkyl), an optionally substituted heterocyclyl(alkyl), an optionally substituted acyl, an optionally substituted thiocarbonyl, an optionally substituted O-carbamyl, an optionally substituted N-carbamyl, an optionally substituted O-thiocarbamyl, an optionally substituted N-thiocarbamyl, an optionally substituted C-thioamido, an optionally substituted N-thioamido, an optionally substituted sulfenyl, an optionally substituted sulfinyl, an optionally substituted sulfonyl, an optionally substituted haloalkoxy, or a first boron-containing moiety wherein the first boron-containing moiety is connected by the boron. In some embodiments, the variable $R^1$ in the compounds of Formula (I) and/or Formula (A) can be hydrogen, an optionally substituted $C_{1-30}$ alkyl, an optionally substituted $C_{2-30}$ alkenyl, an optionally substituted $C_{3-10}$ monocyclic cycloalkyl, an optionally substituted aryl, an optionally substituted heteroaryl, an optionally substituted heterocyclyl, a halogen, an amino, a mono-substituted amino, a di-substituted amino, an optionally substituted C-amido, an optionally substituted N-amido, an optionally substituted $C_{1-30}$ alkoxy, a hydroxy, an optionally substituted $C_{1-30}$ haloalkyl, a cyano, an optionally substituted S-sulfonamido, an optionally substituted N-sulfonamido, an optionally substituted O-carboxy, an optionally substituted $C_{2-30}$ alkynyl, an optionally substituted $C_{3-10}$ cycloalkenyl, an optionally substituted aryl(alkyl), an optionally substituted heteroaryl(alkyl), an optionally substituted heterocyclyl(alkyl), an optionally substituted acyl, an optionally substituted thiocarbonyl, an optionally substituted O-carbamyl, an optionally substituted N-carbamyl, an optionally substituted O-thiocarbamyl, an optionally substituted N-thiocarbamyl, an optionally substituted C-thioamido, an optionally substituted N-thioamido, an optionally substituted sulfenyl, an optionally substituted sulfinyl, an optionally substituted sulfonyl, an optionally substituted haloalkoxy, or a first boron-containing moiety wherein the first boron-containing moiety is connected by the boron. For example, in an embodiment, the first boron-containing moiety can be an organoborane, a boronic ester, a boronic acid, a trifluoroborate salt, an N-coordinated boronate, a boronate or a boronamide.

In various embodiments, the variable $X^1$ in the compounds of Formula (A) can be a halide, a pseudohalide, a —C(=O)Y or a second boron-containing moiety. In some embodiments, the second boron-containing moiety can be an organoborane, a boronic ester, a boronic acid, a trifluoroborate salt, an N-coordinated boronate, a boronate or a boronamide. In certain embodiments, each Y can independently be a halide, an optionally substituted heterocyclyl, an optionally substituted heteroaryl, $SR^6$, $OR^6$, SM or OM. In an embodiment, each $R^6$ can independently be a hydrogen, an optionally substituted $C_{1-30}$ alkyl, an optionally substituted $C_{2-30}$ alkenyl, an optionally substituted $C_{3-30}$ cycloalkyl, an optionally substituted heterocyclyl, an optionally substituted heteroaryl, or an optionally substituted aryl. In an embodiment, each M can independently be a monovalent cation (for example, $Li^+$, $Na^+$, $K^+$ or $NH_4^+$) or a divalent cation (for example, $Mg^{2+}$ or $Ca^{2+}$). In some embodiments, the variable $X^1$ in the compounds of Formula (A) can be —C(=O)$OR^6$. In some embodiments, Y can be $OR^6$ and $R^6$ can be hydrogen. In other embodiments, Y can be $OR^6$ and $R^6$ can be an unsubstituted $C_{1-30}$ alkyl. In other embodiments, Y can be $OR^6$ and $R^6$ can be an unsubstituted $C_{1-4}$ alkyl. In still other embodiments, Y can be $OR^6$ and $R^6$ can be an optionally substituted heterocyclyl. In variations of these embodiments, the heterocyclyl can have the structure

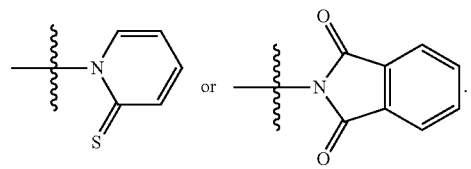 [SMILES: *n1ccccc1=S ; *N1C(=O)c2ccccc2C1=O]

In various embodiments, $X^1$ can be a sulfonate or a halide selected from a chloride, a bromide or an iodide. In various embodiments, the variable $X^1$ in the compounds of Formula (A) can be a second boron-containing moiety, such including those described herein. An advantage of the methods described herein is that $X^1$ does not need to be converted to an activated ester (for example, —C(=O)O(alkyl)) to undergo the reaction and provide good yields of the product, such as a compound of Formula (I), For example, when the second transition metal catalyst is a photoredox catalyst, $X^1$ can be a carboxylic acid (—C(=O)OH) and undergo the reaction and provide good yields of the product, such as a compound of Formula (I).

In certain embodiments, $X^1$ cannot be a halide or a pseudohalide. In certain other embodiments, $X^1$ cannot be a boron-containing moiety. In other embodiments, $X^1$ cannot be a —C(=O)Y. In still other embodiments, $X^1$ cannot be a —C(=O)O(an unsubstituted $C_{1-4}$ alkyl), such as —C(=O)OCH$_3$.

In some embodiments, $R^2$ can be an optionally substituted $C_{1-30}$ alkyl, an optionally substituted $C_{2-30}$ alkenyl, an optionally substituted $C_{3-10}$ cycloalkyl, an optionally substituted $C_{3-10}$ cycloalkenyl, an optionally substituted aryl, an optionally substituted heteroaryl or an optionally substituted heterocyclyl. In some embodiments, $R^2$ can be an optionally substituted $C_{2-30}$ alkenyl, an optionally substituted $C_{3-10}$ cycloalkenyl or an optionally substituted aryl. In various embodiments, the aryl can be a mono-substituted phenyl, a di-substituted phenyl, a tri-substituted phenyl, an ortho-substituted phenyl, a meta-substituted phenyl, or a para-substituted phenyl. In other embodiments, $R^2$ can be an optionally substituted heteroaryl, such as an optionally substituted 5- or 6-membered monocyclic heteroaryl an optionally substituted 9- or 10-membered bicyclic heteroaryl. When substituted, the heteroaryl of $R^2$ can be with one substituent. The heteroaryl of $R^2$ can be also substituted with multiple substituents. Possible substituents that can be present on a substituted $R^2$ group are provided herein under "optionally substituted". In some embodiments, $R^2$ can be a substituted when a substituent can be selected from halogen, an unsubstituted $C_{1-4}$ alkyl, an unsubstituted $C_{1-4}$ alkoxy, an unsubstituted $C_{1-4}$ haloalkyl, an unsubstituted $C_{1-4}$ haloalkoxy, an unsubstituted mono-substituted amino, an unsubstituted di-substituted amino, cyano, nitro, an optionally substituted sulfenyl, an optionally substituted sulfinyl, an optionally substituted sulfonyl, an optionally substituted acyl, an optionally substituted aryl, an optionally substituted heteroaryl and an optionally substituted heterocyclyl. In further embodiments, $R^2$ can be an optionally substituted (E)-$C_{2-30}$ alkenyl or an optionally substituted (Z)—$C_{2-30}$ alkenyl. In still further embodiments, $R^2$ cannot comprise a heteroatom at an alpha (α) position. $R^2$ substitution described in this paragraph is irrespective of substitution by $X^2$.

In some embodiments, $X^2$ can be a halide, a pseudohalide, a —C(=O)Y, a zinc halide, a zinc pseudohalide or a third boron-containing moiety. In an embodiment, the third boron-containing moiety can be an organoborane, a boronic ester, a boronic acid, a trifluoroborate salt, an N-coordinated boronate, a boronate or a boronamide. In certain embodiments, when $R^2$ is alkyl, $X^2$ cannot be a halide or a pseudohalide. In certain other embodiments, at least one of $X^1$ and $X^2$ cannot be a halide or pseudohalide. In various embodiments, the bond between $R^2$ and $X^2$ can be an sp$^2$ carbon-heteroatom bond.

In some embodiments, the first transition metal catalyst can be a Pd catalyst or a Ni catalyst. In some embodiments, when the first transition metal catalyst is a Pd catalyst, the second transition metal catalyst is not present.

In some embodiments, the second transition metal catalyst can be an Ir catalyst, a Cu catalyst or a Ru catalyst. In certain embodiments, when the second transition metal catalyst is present, the second transition metal catalyst can be an Ir catalyst, the first transition metal catalyst can be an Ni catalyst, $X^1$ can be a —C(=O)Y, and $X^2$ can be a halide or pseudohalide.

In some embodiments, at least one of $X^1$ and $X^2$ cannot be a boron-containing moiety.

In some embodiments, when the second transition metal catalyst is present, either $X^1$ or $X^2$ is a —C(=O)Y.

In certain embodiments, the first transition metal catalyst can be a cross coupling catalyst. In various embodiments, the cross coupling catalyst can be a Suzuki coupling catalyst or a Negishi coupling catalyst. In certain embodiments, the first transition metal catalyst is selected to undergo oxidative addition to the compound of Formula (A) and/or the compound of Formula (B). In an embodiment, the first transition metal catalyst is not an iron (Fe) catalyst that includes an Fe atom.

In certain embodiments, the first transition metal catalyst can be a Pd catalyst comprising a Pd atom. In variations of these embodiments, the Pd atom can be ligated by one or more of a halide, a sulfonate, a carboxylate, a phosphine, an imine, an aromatized N (e.g., pyridine), an alkene, an amine, a nitrile, a carbanion or a carbene. In further variations, a Pd catalyst can include a Pd(O) atom. In still further variations, a Pd catalyst can include a Pd(II) atom. In some variations, a Pd atom can be ligated by a bidentate moiety. In some further variations, a Pd atom can be ligated by a tridentate moiety.

In some embodiments, a Pd catalyst can be a catalyst as described elsewhere herein. In certain embodiments, a Pd catalyst can be Pd(PPh$_3$)$_4$.

In some embodiments, the first transition metal catalyst can be a Ni catalyst including a Ni atom. In variations of these embodiments, the Ni atom can be ligated by one or more of a halide, a sulfonate, a carboxylate, a phosphine, an imine, an aromatized N, an alkene, an amine, a nitrile, a carbanion or a carbene. In further variations, a Ni catalyst can include a Ni(O) atom. In still further variations, a Ni catalyst can include a Ni(II) atom. In some variations, a Ni atom can be ligated by a bidentate moiety. In some further variations, a Ni atom can be ligated by a tridentate moiety.

In some embodiments, a Ni catalyst can be a catalyst as described elsewhere herein. In some embodiments, a Ni catalyst can be NiCl$_2$.dimethoxyethane.

In some embodiments, the second transition metal catalyst can be a photoredox catalyst. In an embodiment, the second transition metal catalyst is not an iron (Fe) catalyst that includes an Fe atom.

In some embodiments, the second transition metal catalyst can be a Ru catalyst including a Ru atom. In variations of these embodiments, the Ru atom can be ligated by one or more of a halide, a sulfonate, a carboxylate, a phosphine, an imine, an aromatized N (e.g., pyridine), an alkene, an amine, a nitrile, a carbanion or a carbene. In further variations, the Ru atom can be ligated by a bidentate moiety, for example, a bipyridine (bpy) or a derivative thereof. In some embodiments, a Ru catalyst can be a catalyst as described elsewhere herein.

In some embodiments, the second transition metal catalyst can be an Ir catalyst including an Ir atom. In variations of these embodiments, the Ir atom can be ligated by one or more of a halide, a sulfonate, a carboxylate, a phosphine, an imine, an aromatized N (e.g., pyridine), an alkene, an amine, a nitrile, a carbanion or a carbene. In further variations, the Ir atom can be ligated by a bidentate moiety, for example, a bipyridine (bpy) or a derivative thereof. In some embodiments, an Ir catalyst can be a catalyst as described elsewhere herein. In certain embodiments, an Ir catalyst can be [Ir{dF(CF$_3$)ppy}$_2$(dtbpy)]PF$_6$.

In some embodiments, the second transition metal catalyst can be a Cu catalyst comprising a Cu atom.

In some embodiments, the compound of Formula (A) can have the structure:

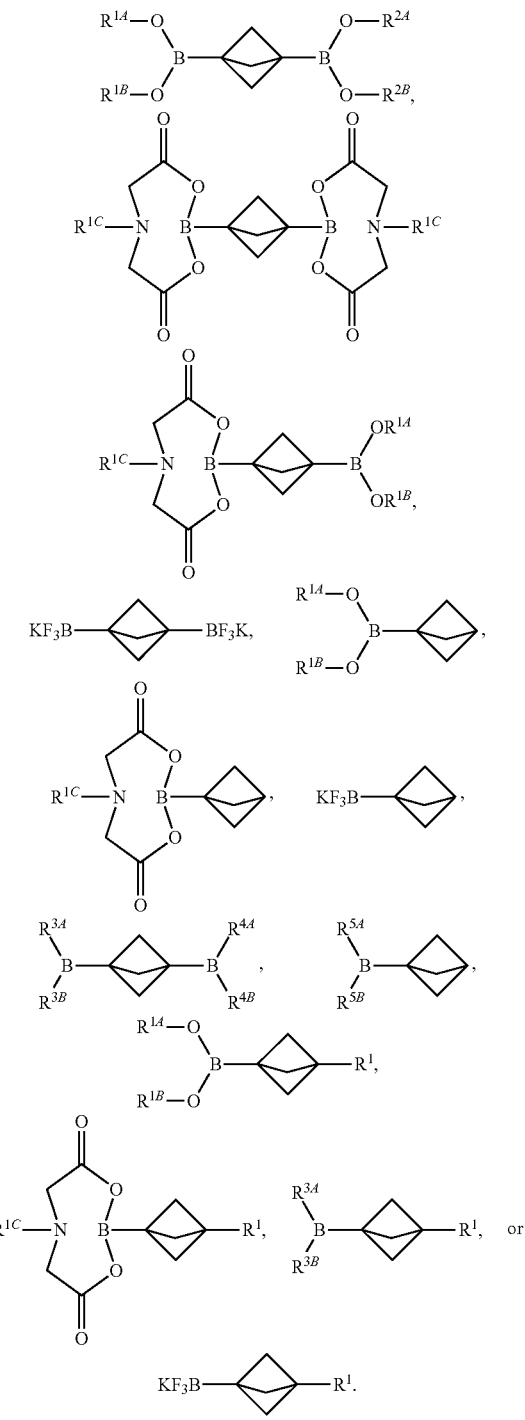

In some embodiments, $R^{1A}$ and $R^{1B}$ can independently be hydrogen, an optionally substituted $C_{1-30}$ alkyl or an optionally substituted $C_{3-10}$ cycloalkyl. In other embodiments, $OR^{1A}$, $OR^{1B}$ and the boron atom to which they attach can be taken together to form an optionally substituted heterocyclyl. For example, $OR^{1A}$, $OR^{1B}$ and the boron atom can form an optionally substituted 5-membered heterocyclyl, such as

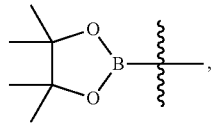

or a 8-membered heterocyclyl, such as

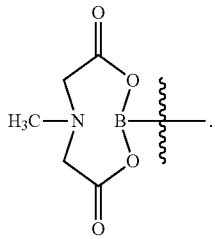 [SMILES: *B1OC(=O)CN(C)CC(=O)O1]

In some embodiments, $R^{1A}$ and $R^{1B}$ can each be hydrogen. In some embodiments, each $R^{1C}$ can independently be hydrogen, an optionally substituted $C_{1-30}$ alkyl or an optionally substituted $C_{3-10}$ cycloalkyl.

In some embodiments, $R^{2A}$ and $R^{2B}$ can independently be hydrogen or an optionally substituted $C_{1-30}$ alkyl. In other embodiments, $OR^{2A}$, $OR^{2B}$ and the boron atom to which they attach can be taken together to form an optionally substituted heterocyclyl. For example, $OR^{2A}$, $OR^{2B}$ and the boron atom can form an optionally substituted 5-membered heterocyclyl, such as

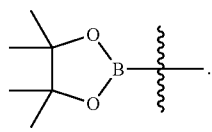 [SMILES: *B1OC(C)(C)C(C)(C)O1]

In some embodiments, $R^{3A}$ and $R^{3B}$ can independently be an optionally substituted $C_{1-30}$ alkyl, an optionally substituted $C_{3-10}$ cycloalkyl, an amine, an arylamine, or an alkylamine. In other embodiments, $R^{3A}$, $R^{3B}$ and the boron atom to which they attach can be taken together to form an optionally substituted heterocyclyl.

In some embodiments, $R^{4A}$ and $R^{4B}$ can independently be an optionally substituted $C_{1-30}$ alkyl, an optionally substituted $C_{3-10}$ cycloalkyl, an amine, an arylamine, or an alkylamine. In other embodiments, $R^{4A}$, $R^{4B}$ and the boron atom to which they attach can be taken together to form an optionally substituted heterocyclyl.

In some embodiments, $R^{5A}$ and $R^{5B}$ can independently be an optionally substituted $C_{1-30}$ alkyl, an optionally substituted $C_{3-10}$ cycloalkyl, an amine, an arylamine, or an alkylamine. In other embodiments, $R^{5A}$, $R^{5B}$ and the boron atom to which they attach can be taken together to form an optionally substituted heterocyclyl.

In some embodiments, $X^1$ can be a halide, for example, a chloride, a bromide, or an iodide.

In some embodiments, $X^1$ can be a pseudohalide, for example, a sulfonate, a phosphate, a cyanide, an azide, an isocyanate, a thioisocyanate, or a quaternary nitrogen moiety. In variations of these embodiments, $X^1$ can be a sulfonate, for example, triflate, mesylate, tosylate, nitrophenyl sulfonate, bromophenyl sulfonate or benzene sulfonate.

In some embodiments, $X^2$ can be a halide, for example, a chloride, a bromide, or an iodide.

In some embodiments, $X^2$ can be a zinc halide or a zinc pseudohalide, for example, a zinc chloride or zinc bromide. In certain embodiments, when $X^2$ is a zinc halide or a zinc pseudohalide, the first transition metal catalyst can be a Negishi coupling catalyst. In other embodiments, $X^2$ can be a magnesium halide or a magnesium pseudohalide, for example, a magnesium chloride or magnesium bromide.

In some embodiments, $R^1$ can be hydrogen. In other embodiments, $R^1$ can be an optionally substituted aryl, for example an unsubstituted or substituted phenyl. In some embodiments, $R^1$ can be a mono-substituted phenyl. Possible substituents that can be present on a mono-substituted phenyl are provided herein under "optionally substituted". In some embodiments, $R^1$ can be a mono-substituted phenyl, wherein the substitution can be selected from halogen, hydroxy, an unsubstituted $C_{1-4}$ alkyl, an unsubstituted $C_{1-4}$ alkoxy, an unsubstituted $C_{1-4}$ haloalkyl, an unsubstituted $C_{1-4}$ haloalkoxy, an unsubstituted a mono-substituted amino, an unsubstituted di-substituted amino, cyano, nitro, an optionally substituted sulfenyl, an optionally substituted sulfinyl, an optionally substituted sulfonyl, an optionally substituted acyl, an optionally substituted aryl, an optionally substituted heteroaryl and an optionally substituted heterocyclyl. In still other embodiments, $R^1$ can be an optionally substituted heteroaryl. For example, $R^1$ can be an unsubstituted or substituted monocyclic heteroaryl or an unsubstituted or substituted bicyclic heteroaryl. In some embodiments, $R^1$ can be an optionally substituted 5- or 6-membered monocyclic heteroaryl. In other embodiments, $R^1$ can be an optionally substituted 9- or 10-membered bicyclic heteroaryl. When substituted, the heteroaryl of $R^1$ can be mono-substituted. The heteroaryl of $R^1$ can be also substituted with multiple substituents. Possible substituents that can be present on a substituted heteroaryl of $R^1$ are provided herein under "optionally substituted". In some embodiments, $R^1$ can be a mono-substituted heteroaryl, wherein the substitution can be selected from halogen, hydroxy, an unsubstituted $C_{1-4}$ alkyl, an unsubstituted $C_{1-4}$ alkoxy, an unsubstituted $C_{1-4}$ haloalkyl, an unsubstituted $C_{1-4}$ haloalkoxy, an unsubstituted mono-substituted amino, an unsubstituted di-substituted amino, cyano, nitro, an optionally substituted sulfenyl, an optionally substituted sulfinyl, an optionally substituted sulfonyl, an optionally substituted acyl, an optionally substituted aryl, an optionally substituted heteroaryl and an optionally substituted heterocyclyl. In yet still other embodiments, $R^1$ can be a first boron-containing moiety, wherein the first boron-containing moiety is connected by the boron. Examples of first boron-containing moieties are described herein in further detail. In some embodiments, $R^1$ can be an optionally substituted C-carboxy, such as an optionally substituted —C(=O)—O-(an optionally substituted heteroaryl). In other embodiments, $R^1$ can be an optionally substituted N-carbamyl. For example, $R^1$ can be —NH(C(=O))O—($C_{1-4}$ alkyl).

In some embodiments, $R^1$ can be a first boron-containing moiety, wherein the first boron-containing moiety is connected by the boron; and $X^1$ can be a second boron-containing moiety, such as those described herein. In other embodiments, $R^1$ can be an optionally substituted aryl or an optionally substituted heteroaryl; and $X^1$ can be —C(=O)Y, such as —C(=O)$OR^6$ (for example, —C(=O)OH). In still other embodiments, $R^1$ can be an optionally substituted aryl or an optionally substituted heteroaryl; and $X^1$ can be a second boron-containing moiety. In still other embodiments, $R^1$ can be an optionally substituted C-carboxy; and $X^1$ can be —C(=O)Y, such as —C(=O)$OR^6$ (for example, —C(=O)OH). As described herein $X^1$ can be —C(=O)OH or —C(=O)O(unsubstituted $C_{1-4}$ alkyl).

In some embodiments, the reacting of the compound of Formula (A) with the compound of Formula (B) to form the compound of Formula (I) can take place in the presence of a ligand. In variations of these embodiments, the ligand can be A-caPhos, a-taPhos, Binap, BIPHEP, BippyPhos, Ad-BrettPhos, ditBuBrettPhos, BrettPhos, CataCXcium POMeCy, CataCXcium PtB, CataCXium PiCy, CataCXium FBn, CataCXium PCy, CataCXium PInCy, CataCXium POMetB, CataXCium A, CataXCium ABn, CataXCium AHI, CataXCium C, CataXCium FBu, CataXCium FPrPh, CataXCium FSulf, CataXCium PIntB, CPhos, Cy-BIPHEP, Cy-BippyPhos, Cy-JohnPhos, Cy-PhenCarPhos, DavePhos, DCEPhos, DCyPF, DiPPF, di-tBu-neopentylPhosphonium $HBF_4$, DPEPhos, DPPBz, DPPE, DPPF, DtBPF, DTP-DPEPhos, JackiePhos, JohnPhos, Me4XPhos, Me4t-BuX-Phos, MeDalPhos, MePhos, MorDalPhos, N-dicyclohexyl-phosphino-2-(2'-methylphenyl)-1H-indole, XantPhos, $PCy_3$ $HBF_4$, P(o-OMePh)$_3$, PPh$_3$, PtBu$_3$ $HBF_4$, PXy$_3$, QPhos, PhDavePhos, RockPhos, RuPhos, SL-J003-1, SL-J009-1, SPhos, SPhos-SO$_3$Na, SymPhos, tBuBiNap, tBuDavePhos, tBuMePhos, tBuXantPhos, tBuXPhos, TrixiePhos, XantPhos, XPhos, XPhos-SO$_3$Na, Me$_3$P $HBF_4$, Et$_3$P $HBF_4$, xyl-Binap, Cy-cBRIDP, AmindolePhos, NPCy o-Andole-Phos, NPCy Phendole-Phos, cBRIDP, vBRIDP, CyvBRIDP, CM-Phos, KitPhos, 4,4'-di-tert-butyl-2,2'-dipyridyl (bbbpy), 2,2'-bipyridyl, 4,4'-dimethoxy-2,2'-bipyridyl, 2,2'-biquinoline, bathophenanthroline, s-BuPyBox, neocuproine, trans-2-aminocyclohexanol or combinations thereof. In some embodiments, a ligand can be bbbpy.

In some embodiments, reacting of the compound of Formula (A) with the compound of Formula (B) to form the compound of Formula (I) can take place in the presence of a precatalyst. In variations of these embodiments, the precatalyst can be XantPhos 3rd gen, tBuXPhos 3rd gen, CPhos 3rd gen, APhos 3rd gen, phosphaadamantane 3rd gen, XPhos 3rd gen, RuPhos 3rd gen, JackiePhos 3rd gen, 1st gen BrettPhos, 1st gen ditBuXPhos, 1st gen RuPhos, 1st gen SPhos, 1st gen XPhos, 2nd gen RuPhos, 2nd gen SPhos, 2nd gen XPhos, OMs Pd Dimer or combinations thereof.

In some embodiments, reacting of the compound of Formula (A) with the compound of Formula (B) to form the compound of Formula (I) can take place in the presence of a base. In some embodiments, the base can be a metal hydroxide base, a metal carbonate base, a metal bicarbonate base, an amine base, a metal fluoride base, a metal alkoxide base, a metal carboxylate base or a metal phosphate base. In variations of these embodiments, the base can be a base as described elsewhere herein.

In some embodiments, the variable M in the description of Y and $X^1$, can be a monovalent cation, for example, Li$^+$, Na$^+$, K$^+$, Rb$^+$, Cs$^+$, or a quaternary nitrogen. In other embodiments, M can be a divalent cation, for example, $Mg^{+2}$, $Ca^{+2}$, $Sr^{+2}$, or $Ba^{+2}$.

In some embodiments, each $R^6$ can independently be a hydrogen or a $C_{1-4}$ alkyl. In some embodiments, each $R^6$ can hydrogen In some embodiments, reacting of the compound of Formula (A) with the compound of Formula (B) to form the compound of Formula (I) can take place in the presence of visible light. In further embodiments, when the second transition metal catalyst is present as a photoredox catalyst, such reacting can take place in the presence of visible light.

In some embodiments, the compound of Formula (I) can be prepared as a salt.

In some embodiments, the molar ratio of a compound of Formula (A) to a compound of Formula (B) can be about 0.1:1 to about 10:1, the base can be a metal alkoxide base, the first transition metal catalyst can be a Pd catalyst. In some embodiments of the reaction, $X^1$ can be a second boron-containing moiety selected from an organoborane, a boronic ester, a boronic acid, a trifluoroborate salt, an N-coordinated boronate, a boronate or a boronamide. In some embodiments of the reaction, $X^1$ can be a halide selected from a chloride, a bromide and an iodide.

In some embodiments, the molar ratio of a compound of Formula (A) to a compound of Formula (B) in the reaction to form the compound of Formula (I) can be in the range of about 0.1:1 to about 10:1, the base can be a metal carbonate base, the first transition metal catalyst can be a Ni catalyst, $X^1$ can be a —C(=O)Y, Y can be $OR^6$, and $X^1$ can be a halide selected from a chloride, a bromide and an iodide.

A person of skill in the art, guided by the detailed teachings herein, can select an appropriate cross coupling catalyst as the first transition metal catalyst. A cross coupling catalyst generally will be selected to perform at least two functions: an oxidative addition and a reductive elimination. In an oxidative addition, a metal, (e.g., the transition metal), donates a pair of electrons to an organic halide or organic pseudohalide to generate a first intermediate organometallic species. In general, an electron-rich or low valent transition metal species will undergo oxidative addition. In a reductive elimination, a metal in a carbon-metal bond in a second intermediate organometallic species undergoes a two electron reduction, leaving a new bond between two organic molecule ligands. In general, an electron poor or high valent transition metal species will undergo reductive elimination. Thus, selecting the first transition metal catalyst can comprise identifying a cross coupling catalyst that can cycle between these two types of species. When no photoredox catalyst is present in a reaction mixture, a cross coupling catalyst may also be selected to perform a transmetallation function. In a transmetallation, a first metal or semi-metal bonded to an organic moiety is replaced with a second metal to generate a second intermediate organometallic species, where the first metal or semi-metal can be, for example, a boron atom of a boron-containing moiety or a zinc atom of a zinc-containing moiety, and the second metal can be a transition metal of a cross coupling catalyst, for example, included in a first intermediate organometallic species. A cross coupling catalyst, particularly when combined in a reaction mixture with a photoredox catalyst, can also be selected to undergo a single electron oxidation function with a free radical (wherein the free radical is reduced). In such a function, a metal, for example, a transition metal of a cross coupling catalyst included in a first intermediate organometallic species, donates an electron to a free radical to form a new carbon-metal bond. The various functions of a cross coupling catalyst can occur separately or be coextensive, and generally each is accompanied by a cycling of the oxidation state of a transition metal in the catalyst.

A cross coupling catalyst can perform the functions described herein in the form it is added to a reaction mixture, or may be active in a different form, for example, a form that is generated in situ in a reaction mixture, for example, by ligand exchange. A cross coupling catalyst can be charged or uncharged, and can cycle between uncharged and charged in a reaction mixture. A transition metal atom in a cross coupling catalyst generally can be any suitable transition metal atom for performing oxidative addition, transmetallation, single electron oxidation with a free radical and/or reductive elimination. Such atoms are known to include Ni atoms and Pd atoms, although in some contexts other transition metals may be effective to induce a coupling reaction. A cross coupling catalyst may include one or more transition metal atoms. In some embodiments, a cross coupling catalyst can be a Ni catalyst including a Ni atom. In other embodiments, a cross coupling catalyst can be a Pd catalyst including a Pd atom. The transition metal in a cross coupling catalyst will be ligated by one or more ligands. A person of skill in the art can select an appropriate catalyst and ligands based on knowledge available to such a person as guided by the detailed teachings provided herein. For a discussion of cross coupling catalysts, see Meijere et al., Eds., Metal-Catalyzed Cross coupling Reactions and More (2014, Wiley-VCH); Phan et al., On the Nature of the Active Species in Palladium Catalyzed Mizoroki-Heck and Suzuki-Miyaura Couplings—Homogeneous or Heterogeneous Catalysis, A Critical Review, Advanced Synthesis & Catalysis (2006) Vol. 348, Issue 6, pages 609-679; "Organotransition Metal Chemistry—From Bonding to Catalysis" John Hartwig (University Science Books, 2010). A catalyst loading should be chosen as to provide a desired yield. In some embodiments, a cross coupling catalyst can be included in about 0.1 mol %, about 1 mol %, about 5 mol % or about 10 mol % based on a compound of Formula (A).

A Suzuki coupling catalyst is a cross coupling catalyst that can, under appropriate conditions, induce a coupling between an organic halide or pseudohalide and a boron-containing organic moiety. A person of ordinary skill in the art guided by the teachings provided herein can select a suitable Suzuki coupling catalyst and determine an effective amount for a particular reaction. See Miyaura et al., Chem. Rev. (1995) vol. 95, 2457-2483; Han, Chem. Soc. Rev. (2013) Vol. 42, 5270-5298. A Negishi coupling catalyst is a cross coupling catalyst that can, under appropriate conditions, induce a coupling between an organic halide or pseudohalide and a zinc-containing organic moiety. A person of ordinary skill guided by the teachings provided herein can select a suitable Negishi coupling catalyst for a particular reaction. See Negishi et al., Aldrichim. Acta, (2005) Vol. 38(3), 71-87.

Various Ni catalysts are cross coupling catalysts that can induce a coupling reaction. A person of ordinary skill guided by the teachings provided herein can select a suitable Ni catalyst and determine an effective amount for a particular coupling reaction. A Ni catalyst can include ligands which dissociate under certain conditions to be substituted by, for example, a solvent molecule or another ligand. A Ni catalyst may be active in the form it is added to a reaction mixture, or may be active in a different form that is generated in situ. In some embodiments, a Ni catalyst can be selected to undergo oxidative addition to a carbon-halide or carbon-pseudohalide bond. In further embodiments, an Ni catalyst can be selected to undergo oxidative addition to the compound of Formula (A) or the compound of Formula (B). In other embodiments, a Ni catalyst can comprise a Ni atom in a particular oxidation state, for example, a Ni(0) atom or a Ni(II) atom. In some embodiments, an Ni catalyst can be selected from $NiCl_2$(dtbpy), chloro(2-methylphenyl)bis(triphenylphosphine)nickel(II), [1,2-bis(diphenylphosphino)ethane]dichloronickel(II), Ni(acac)$_2$, $NiCl_2(PCy_3)_2$, Ni(1,5-COD)$_2$, $NiCl_2$*dimethoxyethane, $NiCl_2$-glyme, $NiCl_2$, $NiCl_2$(dppf), $NiCl_2$(dppe), Bis(cyclopentadienyl)nickel(II), 2,3-Bis(2,6-diisopropylphenylimino)butane nickel(II)

dibromide, Bis[(2-dimethylamino)phenyl]amine nickel(II) chloride, Bis(isopropylcyclopentadienyl)nickel, Bis(methylcyclopentadienyl)nickel(II), N,N'-Bis(salicylidene)ethylenediaminonickel(II), Bis(triphenylphosphine)nickel(II) dichloride, Chloro(cyclopentadienyl)(triphenylphosphine)nickel(II), Chloro(ethylcyclopentadienyl)(triphenylphosphinenickel(II), Chloro(2-methylphenyl)bis(triphenylphosphine)nickel(II), Chloro(1-naphthyl)bis(triphenylphosphine)nickel(II), Dibromobis (tributylphosphine)nickel(II), Dibromobis (triphenylphosphine)nickel(II), Dichlorobis (tributylphosphine)nickel(II), Dichlorobis (trimethylphosphine)nickel(II), methallylnickel chloride dimer, Hexaamminenickel(II) bromide, Nickel(II) acetate, Nickel(II) acetylacetonate, Nickel(II) bis(trifluoromethanesulfonimide), Nickel(II) bromide, Nickel(II) hexafluoroacetylacetonate, Nickel(II) trifluoromethanesulfonate, Tetrakis(triphenylphosphite)nickel(0), Trovitch Ni-Precatalyst and NiCl$_2$(dppp). See Adhikary, A. et al., Pincer and Pincer-Type Complexes (2014), 117-147; Takahashi, T. et al., Modern Organonickel Chemistry (2005), 41-55. In some embodiments, when a photoredox catalyst is present, a Ni catalyst can be selected from

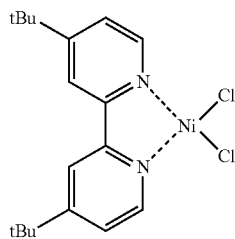

and NiCl$_2$.glyme.

Various Pd catalysts are cross coupling catalysts that can induce a coupling reaction. A person of ordinary skill guided by the teachings provided herein can select a suitable Pd catalyst and determine an effective amount for a particular coupling reaction. A Pd catalyst can include ligands which dissociate under certain conditions to be substituted by, for example, a solvent molecule or another ligand. A Pd catalyst may be active in the form it is added to a reaction mixture, or may be active in a different form that is generated in situ. In some embodiments, a Pd catalyst is selected to undergo oxidative addition to a carbon-halide or carbon-pseudohalide bond. In further embodiments, a Pd catalyst is selected to undergo oxidative addition to the compound of Formula (A) or the compound of Formula (B). In other embodiments, a Pd catalyst can comprise a Pd atom in a particular oxidation state, for example, a Pd(0) atom or a Pd(II) atom. In some embodiments, a Pd catalyst can be selected from PdCl$_2$, Pd(ACN)$_2$Cl$_2$, Pd(benzonitrile)$_2$Cl$_2$, Pd(1,5-COD)Cl$_2$, allylpalladium chloride dimer, Pd(dba)$_2$, Pd$_2$(dba)$_3$, Pd(OAc)$_2$, Pd(AmPhos)$_2$, Pd(P(tBu)$_3$)$_2$, Pd(AmPhos)$_2$Cl$_2$, Pd(P(o-tolyl)$_3$)$_2$, Pd(PPh$_3$)$_4$, Pd(QPhos)$_2$, PdCl$_2$(dtbpf), Pd(PCy$_3$)$_2$, bis(di-t-butyl-phenylphosphine)Pd(Cl)$_2$, PdCl$_2$(PPh$_3$)$_4$, PdCl$_2$(dppf), Chloro{2-[1-(N-methoxy)iminoethyl]phenyl}{[1,3-bis(2,6-di-i-propylphenyl]imidzole-2-ylidene}palladium(II), Chloro {2-[(1-(N-phenyl)iminoethyl]phenyl}{[1,3-bis(2,6-di-i-propylphenyl]imidzole-2-ylidene}palladium(II), Methanesulfonato(1,1-bis(di-t-butylphosphino)ferrocene)(2'-amino-1,1'-biphenyl-2-yl)palladium(II), Methanesulfonato(2-di-t-butylphosphino-3,4,5,6-tetramethyl-2',4',6'-tri-i-propylbiphenyl)(2'-amino-1,1'-biphenyl-2-yl)palladium(II), Allyl(cyclopentadienyl)palladium(II), Methanesulfonato(2-di-t-butylphosphino-1,1'-binaphthyl)(2'-amino-1,1'-biphenyl-2-yl)palladium(II), Di-MU-iodobis(tri-t-butylphosphino)dipalladium(I), Methanesulfonato[2-diethylphosphino-2',6'-bis(dimethylamino)-1,1-biphenyl](2'-amino-1,1'-biphenyl-2-yl)palladium(II), Acetato(2'-di-t-butylphosphino-1,1'-biphenyl-2-yl)palladium(II), Acetato (2,9-dimethyl-1,10-phenanthroline)palladium(II) dimer bis (trifluoromethanesulfonate), Allylchloro[1,3-bis(2,6-di-i-propylphenyl)-4,5-dihydroimidazol-2-ylidene]palladium (II), Allylchloro[1,3-bis(2,6-di-i-propylphenyl)imidazol-2-ylidene]palladium(II), Allylchloro[1,3-bis(2,4,6-trimethylphenyl)imidazol-2-ylidene]palladium(II), trans-Bis(dicyclohexylamine)bis(acetato)palladium(II), Bis{[4-(N,N-dimethylamino)phenyl]di-t-butylphosphino}palladium(0), N,N'-[Bis(2,6-dimethylphenyl)-1,3-dimethyl-1,3-propanediylidene](methyl) (triethylphosphine)palladium(II), [1,3-Bis(2,6-di-i-propylphenyl)-4,5-dihydroimidazol-2-ylidene]{2-[(dimethylamino-kN)methyl]phenyl-kC}(pyridine) palladium(II) tetrafluoroborate, 1,3-Bis(2,6-di-i-propylphenyl)imidazol-2-ylidene(1,4-naphthoquinone) palladium(0), [P,P'-1,3-Bis(di-i-propylphosphino)propane] [P-1,3-bis(di-i-propylphosphino)propane]palladium(0), 1,2-Bis(phenylsulfinyl)ethanepalladium(II) acetate, Bis(tri-t-butylphosphine)palladium(0), [1,3-Bis(2,4,6-trimethylphenyl)-4,5-dihydroimidazol-2-ylidene]{2-[(dimethylamino-kN)methyl]phenyl-kC}(pyridine) palladium (II) tetrafluoroborate, 1,3-Bis(2,4,6-trimethylphenyl)imidazol-2-ylidene(1,4-naphthoquinone) palladium(0) dimer, Bis(tri-o-tolylphosphine)palladium(0), Chloro(1-t-butylindenyl) [1,3-bis(2,6-di-i-propylphenyl) imidazol-2-yl]palladium(II), Chloro(1-t-butylindenyl)[2-(dicyclohexylphosphino)-2',6'-dimethoxy-1,1'-biphenyl]palladium(II), Chloro(1-t-butylindenyl)[2-(dicyclohexylphosphino)-2',6'-di-i-propoxy-1,1'-biphenyl]palladium(II), Chloro(1-t-butylindenyl)[2-(dicyclohexylphosphino)-2',4',6'-tri-i-propyl-1,1'-biphenyl] palladium(II), Chloro(1-t-butylindenyl)palladium(II) dimer, Chloro(2-di-t-butylphosphino-2',4',6'-tri-i-propyl-1,1'-biphenyl) [2-(2-aminoethyl)phenyl] palladium(II), Chloro(2-dicyclohexylphosphino-2',6'-dimethoxy-1,1'-biphenyl)(2'-amino-1,1'-biphenyl-2-yl)palladium(II), Chloro(2-dicyclohexylphosphino-2',6'-dimethoxy-1,1'-biphenyl) [2-(2-aminoethylphenyl)]palladium(II), Chloro(2-dicyclohexylphosphino-3,6-dimethoxy-2',4',6'-tri-i-propyl-1,1'-biphenyl)(2'-amino-1,1'-biphenyl-2-yl)palladium(II), Chloro[2-(dicyclohexylphosphino)-3,6-dimethoxy-2',4',6'-tri-i-propyl-1,1'-biphenyl][2-(2-aminoethyl)phenyl]palladium(II), Chloro[2-(dicyclohexylphosphino)-2'-(N,N-dimethylamino)-1,1'-biphenyl](2'-amino-1,1'-biphenyl-2-yl) palladium(II), Chloro(2-dicyclohexylphosphino-2',6'-di-i-propoxy-1,1'-biphenyl)(2'-amino-1,1'-biphenyl-2-yl) palladium(II), Chloro(2-dicyclohexylphosphino-2',6'-di-i-propoxy-1,1'-biphenyl)[2-(2-aminoethylphenyl)]palladium (II), Chloro(2-dicyclohexylphosphino-2',4',6'-tri-i-propyl-1,1'-biphenyl)(2'-amino-1,1'-biphenyl-2-yl) palladium(II), Chloro(2-dicyclohexylphosphino-2',4',6'-tri-i-propyl-1,1'-biphenyl)[2-(2-aminoethyl)phenyl] palladium(II), Chloro{[4-(N,N-dimethylamino)phenyl]di-t-butylphosphino}(2'-amino-1,1'-biphenyl-2-yl)palladium(II), Chloro[9,9-dimethyl-4,5-bis(diphenylphosphino)xanthene][2'-amino-1,1'-biphenyl]palladium(II), Chloro(di-2-norbornylphosphino) (2'-dimethylamino-1,1'-biphenyl-2-yl)palladium(II), Chloro (di-2-norbornylphosphino)(2-dimethylaminomethylferrocen-1-yl)palladium(II), Chloro

[(1,2,3-η)-1-phenyl-2-propen-1-yl]-{[1,3-bis[2,6-bis(diphenylmethyl)-4-methylphenyl]-2H-imidazol-2-ylidene}palladium(II), Chloro[(1,2,3-η)-3-phenyl-2-propenyl][1,3-bis(2,6-di-i-propylphenyl)-4,5-dihydroimidazol-2-ylidene]palladium(II), Chloro[(1,2,3-η)-3-phenyl-2-propenyl][1,3-bis(2,6-di-i-propylphenyl)imidazol-2-ylidene]palladium(II), Chloro(tri-t-butylphosphine)(2'-amino-1,1'-biphenyl-2-yl)palladium(II), Diacetato[1,3-bis(diphenylphosphino)propane]palladium(II), trans-Di(μ-acetato)bis[o-(di-o-tolylphosphino)benzyl]dipalladium(II), Di-μ-bromobis(tri-t-butylphosphino)dipalladium(I), Dichlorobis(acetonitrile)palladium(II), Dichlorobis(benzonitrile)palladium(II), Dichlorobis(di-t-butylphenylphosphino)palladium(II), Dichloro[1,1'-bis(dicyclohexylphosphino)ferrocene]palladium(II), Dichloro[(R)-(+)-2,2'-bis(di-2-furanylphosphino)-6,6'-dimethoxy-1,1'-biphenyl]palladium(II), Dichlorobis{[4-(N,N-dimethylamino)phenyl]di-t-butylphosphino}palladium(II), Dichloro[(R)-(+)-2,2'-bis(diphenylphosphino)-1,1'-binaphthyl]palladium(II), Dichloro[(S)-(−)-2,2'-bis(diphenylphosphino)-1,1'-binaphthyl]palladium(II), Dichloro[1,4-bis(diphenylphosphino)butane]palladium(II), Dichloro[1,1'-bis(diphenylphosphino)ferrocene]palladium(II), Dichloro{bis[2-(diphenylphosphino)phenyl]ether}palladium(II), Dichloro[1,1'-bis(di-i-propylphosphino)ferrocene]palladium(II), trans-Dichlorobis(triphenylphosphine)palladium(II), Dichloro(di-μ-chloro)bis[1,3-bis(2,6-di-i-propylphenyl)imidazol-2-ylidene]dipalladium(II), Dichloro[9,9-dimethyl-4,5-bis(diphenylphosphino)xanthene]palladium(II), Dichloro(norbornadiene)palladium(II), Methanesulfonato[2,2'-bis(diphenylphosphino)-1,1'-binaphthyl](2'-amino-1,1'-biphenyl-2-yl)palladium(II), Methanesulfonato[1,1'-bis(diphenylphosphino)ferrocene)](2'-amino-1,1'-biphenyl-2-yl)palladium(II), Methanesulfonato[4,6-bis(diphenylphosphino)phenoxazine](2'-amino-1,1'-biphenyl-2-yl)palladium(II), Methanesulfonato[2-bis(3,5-di(trifluoromethyl)phenylphosphino)-3,6-dimethoxy-2',4',6'-tri-i-propyl-1,1'-biphenyl](2'-amino-1,1'-biphenyl-2-yl)palladium(II), Methanesulfonato(diadamantyl-n-butylphosphino)-2'-amino-1,1'-biphenyl-2-yl)palladium(II), Methanesulfonato[2-(di-1-adamantylphosphino)-3,6-dimethoxy-2',4',6'-tri-i-propyl-1,1'-biphenyl](2'-amino-1,1'-biphenyl-2-yl)palladium(II), Methanesulfonato[di-t-butyl(n-butyl)phosphine](2'-amino-1,1'-biphenyl-2-yl)palladium(II), Methanesulfonato(di-t-butylneopentylphosphine)(2'-amino-1,1'-biphenyl-2-yl)palladium(II), Methanesulfonato[2-(di-t-butylphosphino)-2'-(N,N-dimethylamino)-1,1'-biphenyl](2'-amino-1,1'-biphenyl-2-yl)palladium(II), Methanesulfonato(2-(di-t-butylphosphino)-3,6-dimethoxy-2',4',6'-tri-i-propyl-1,1'-biphenyl)(2'-amino-1,1'-biphenyl-2-yl)palladium(II), Methanesulfonato(2-(di-t-butylphosphino)-3-methoxy-6-methyl-2',4',6'-tri-i-propyl-1,1'-biphenyl)(2'-amino-1,1'-biphenyl-2-yl)palladium(II), Methanesulfonato(2-di-t-butylphosphino-2',4',6'-tri-i-propyl-1,1'-biphenyl)(2'-amino-1,1'-biphenyl-2-yl)palladium(II), Methanesulfonato(2-di-t-butylphosphino-2',4',6'-tri-i-propyl-1,1'-biphenyl)(2'-methylamino-1,1'-biphenyl-2-yl)palladium(II), Methanesulfonato(2-dicyclohexylphosphino-2',6'-bis(dimethylamino)-1,1'-biphenyl)(2'-amino-1,1'-biphenyl-2-yl)palladium(II), Methanesulfonato(2-dicyclohexylphosphino-2',6'-dimethoxy-1,1'-biphenyl)(2'-amino-1,1'-biphenyl-2-yl)palladium(II), Methanesulfonato(2-dicyclohexylphosphino-2',6'-dimethoxy-1,1'-biphenyl)(2'-methylamino-1,1'-biphenyl-2-yl)palladium(II), Methanesulfonato(2-dicyclohexylphosphino-3,6-dimethoxy-2',4',6'-tri-i-propyl-1,1'-biphenyl)(2'-amino-1,1'-biphenyl-2-yl)palladium(II), Methanesulfonato(2-dicyclohexylphosphino-3,6-dimethoxy-2',4',6'-tri-i-propyl-1,1'-biphenyl)(2'-methylamino-1,1'-biphenyl-2-yl)palladium(II), Methanesulfonato[2-(dicyclohexylphosphino)-2'-(N,N-dimethylamino)-1,1'-biphenyl](2'-amino-1,1'-biphenyl-2-yl)palladium(II), Methanesulfonato(2-dicyclohexylphosphino-2',6'-di-i-propoxy-1,1'-biphenyl)(2'-amino-1,1'-biphenyl-2-yl)palladium(II), Methanesulfonato(2-dicyclohexylphosphino-2',6'-di-i-propoxy-1,1'-biphenyl)(2'-methylamino-1,1'-biphenyl-2-yl)palladium(II), Methanesulfonato {(R)-(−)-1-[(S)-2-(dicyclohexylphosphino)ferrocenyl]ethyldi-t-butylphosphine}(2'-amino-1,1'-biphenyl-2-yl)palladium(II), Methanesulfonato(2-dicyclohexylphosphino-2',4',6'-tri-i-propyl-1,1'-biphenyl)(2'-amino-1,1'-biphenyl-2-yl)palladium(II), Methanesulfonato(2-dicyclohexylphosphino-2',4',6'-tri-i-propyl-1,1'-biphenyl)(2'-methylamino-1,1'-biphenyl-2-yl)palladium(II), Methanesulfonato {[4-(N,N-dimethylamino)phenyl]di-t-butylphosphino}(2'-amino-1,1'-biphenyl-2-yl)palladium(II), Methanesulfonato[9,9-dimethyl-4,5-bis(diphenylphosphino)xanthene][2'-amino-1,1'-biphenyl]palladium(II), Methanesulfonato[9,9-dimethyl-4,5-bis(diphenylphosphino)xanthene](2'-methylamino-1,1'-biphenyl-2-yl)palladium(II), Methanesulfonato(tri-t-butylphosphino)(2'-amino-1,1'-biphenyl-2-yl)palladium(II), Methanesulfonato(tri-t-butylphosphino)(2'-methylamino-1,1'-biphenyl-2-yl)palladium(II), Methanesulfonato(tricyclohexylphosphine)(2'-amino-1,1'-biphenyl-2-yl)palladium(II), Methanesulfonato(tricyclohexylphosphino)(2'-methylamino-1,1'-biphenyl-2-yl)palladium(II), (2'-Methylamino-1,1'-biphenyl-2-yl)methanesulfonatopalladium(II) dimer, Tris{tris[3,5-bis(trifluoromethyl)phenyl]phosphine}palladium (O), chloro($\eta^2$-P,C-tris(2,4-di-tert-butylphenyl)phosphite)(tricyclohexylphosphine)palladium(II), 2-(2'-di-tert-butylphosphine)biphenylpalladium(II) acetate, di-t-chlorobis[5-chloro-2-[(4-chlorophenyl)(hydroxyimino-κN)methyl]phenyl-κC]palladium dimer, di-μ-chlorobis[5-hydroxy-2-[1-(hydroxyimino-κN)ethyl]phenyl-κC]palladium(II) dimer, dicyclohexyl[9-(3-phenylpropyl)-9-fluorenyl]phosphonium tetrafluoroborate, dicyclohexyl-{2-sulfo-9-[3-(4-sulfo-phenyl)propyl]-9-fluorenyl}phosphonium-hydrogen-sulfate, 2'-(dimethylamino)-2-biphenylyl-palladium(II) chloride dinorbornylphosphine complex, 2-(dimethylaminomethyl)ferrocen-1-yl-palladium(II) chloride dinorbornylphosphine, a Buchwald catalyst, for example a Buchwald palladacycle catalyst (see Bruno et al., Chem Sci. (2013) 4: 916-920; Bruno et al., The Strem Chemiker Vol. XXVII No. 1, January, 2014 and references cited therein), a cyclopalladated 2-aminobiphenylmesylate, a Bedford catalyst (see Sommer, W., Aldrich ChemFiles (2007) 7.10, 17), a Nájera catalyst (see Aldrich ChemFiles (2007) 7.5, 6), a Pd pincer complex (see Selander et al., Chem. Rev. (2011) Vol. 111, 2048-2076; Albrecht et al., Angew. Chem. Int Ed. (2001) Vol. 40, 3750-3781 and references cited therein) and a Pd nanoparticle catalyst.

A person of skill in the art, guided by the detailed teachings herein, can select an appropriate photoredox catalyst as the second transition metal catalyst. A photoredox catalyst generally will be selected to perform at least two functions: excitation under irradiation and a single electron oxidation and/or reduction of an organic molecule. A photoredox catalyst can be selected to undergo excitation of a bound electron under irradiation, especially irradiation by visible light. In a single electron oxidation, a metal (e.g., the transition metal) in an excited catalyst donates a single electron to an organic molecule. If the organic molecule initially includes only paired electrons, the result of the oxidation or reduction will be a free radical. Such a free radical can form a carbon-metal bond with a cross coupling catalyst, as described above. Thus, selecting the second transition metal catalyst can comprise identifying a photoredox catalyst that can be excited by irradiation, especially by visible light, and that can undergo a single electron oxidation and/or reduction of a moiety in an organic molecule. The source of light can be any source emitting a suitable wavelength to interact with a selected photoredox catalyst, as guided by the teachings herein and the knowledge of a person of skill in the art, and can be, for example, a household light source such as an incandescent bulb or a fluorescent bulb, a light emitting diode and the like. An excited photoredox catalyst can accept an electron from, or donate an electron to, a moiety in an organic molecule, where the moiety can be, for example, a carboxylate or a thiohydroxamate ester (e.g., a Barton ester). In some embodiments, a photoredox catalyst can oxidize a carboxylate anion. A photoredox catalyst may perform the functions described herein in the form it is added to a reaction mixture, or may be active in a different form, for example, a form that is generated in situ in a reaction mixture, for example, by ligand exchange. A photoredox catalyst can be charged or uncharged, and can cycle between uncharged and charged in a reaction mixture. For examples of photoredox catalysts, see Zuo et al., Merging photoredox with nickel catalysis: Coupling of a-carboxyl sp$^3$-carbons with aryl halides, Science (2014) Vol. 345, Issue 6195, 437-440; Prier et al., Visible Light Photoredox Catalysis with Transition Metal Complexes: Applications in Organic Synthesis, Chem. Rev., (2013) Vol. 113, 5322-5363. A catalyst loading should be chosen as to provide a desired yield. In some embodiments, a photoredox catalyst can be included in about 0.1 mol %, about 1 mol %, about 5 mol %, about 10 mol %, or about 20 mol % based on a compound of Formula (A), with 1 mol % being preferred.

A transition metal atom in a photoredox catalyst generally can be any suitable transition metal atom which undergoes excitation under irradiation to create a species capable of accepting an electron from an organic molecule. Such atoms are known to include Ir atoms, Ru atoms and Cu atoms, although in some contexts other transition metals may be suitable to induce a photoredox reaction. A photoredox catalyst can include one or more transition metal atoms. A transition metal atom in a photoredox catalyst is preferably ligated by one or more of a bpy ligand, a bpm ligand, a bpz ligand, a bipy ligand, a phen ligand, a dap ligand, and a ppy ligand, where a ppy ligand is especially preferred.

In some embodiments, a photoredox catalyst can be a Ru catalyst. A person of ordinary skill guided by the teachings provided herein can select a suitable Ru catalyst and determine an effective amount for a particular coupling reaction. A Ru catalyst can include ligands which dissociate under certain conditions to be substituted by, for example, a solvent molecule or another ligand. A Ru catalyst may be active in the form it is added to a reaction mixture, or may be active in a different form that is generated in situ. In some embodiments, a Ru catalyst can be selected from Ru(bpy)$_3$Cl$_2$, Ru(bpm)$_3$(PF$_6$)$_2$, Ru(bpz)$_3$(PF$_6$)$_2$, Ru(bpy)$_3$(PF$_6$)$_2$ Ru(menbpy)$_3$(PF$_6$)$_2$ Ru(bpm)$_3$(PF$_6$)$_2$ and Ru(phen)$_3$(PF$_6$)$_2$.

In other embodiments, a photoredox catalyst can be an Ir catalyst. A person of ordinary skill guided by the teachings provided herein can select a suitable Ir catalyst and determine an effective amount for a particular coupling reaction. An Ir catalyst can include ligands which dissociate under certain conditions to be substituted by, for example, a solvent molecule or another ligand. An Ir catalyst may be active in the form it is added to a reaction mixture, or may be active in a different form that is generated in situ. In some embodiments, an Ir catalyst can be selected from Ir[dF(CF$_3$)ppy]$_2$(bpy)PF$_6$, Ir[dF(Me)ppy]$_2$(dtbpy)PF$_6$, Ir[dF(CF$_3$)ppy]$_2$ (dtbpy)PF$_6$, Ir(ppy)$_2$(dtbpy)PF$_6$, Ir(ppy)$_3$, Ir[p-F(t-Bu)ppy]$_3$, Ir(dFppy)$_3$ and Ir(Fppy)$_3$.

In some embodiments, a photoredox catalyst can be an Ir complex or a Ru complex having the structure:

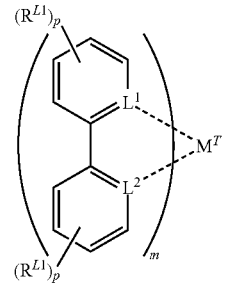

wherein $M^T$ can be Ir or Ru, each $L^1$ and $L^2$ can independently be C or N, m is 3, each $R^{L1}$ can independently be F, CF$_3$, or C$_{1-4}$ alkyl and each p can independently be 0 to 3, and wherein the complex may be positively charged or uncharged and if positively charged, can be associated with one or more counterions selected from perchlorate (ClO$_4^-$), acetate (CH$_3$CO$_2^-$), chloride (Cl$^-$), cyanide (CN$^-$), tetrafluoroborate (BF$_4^-$) and hexafluorophosphate (PF$_6^-$).

As used herein, the term "base" has its ordinary and customary meaning to a person of ordinary skill in the art (and is not to be limited to a special or customized meaning), and refers without limitation to a compound that can bind a proton. A base can optionally perform other functions, for example, a base may be a ligand and/or activate a boron-containing moiety. A base can be charged or uncharged, and can cycle between charged and uncharged, and between different states of charge, upon binding to a proton. A proton bound by a base may be bound at any suitable position or positions of the base, generally by a lone pair of electrons supplied by an atom in the base. In some embodiments, a base can be included in about 1 mol %, about 5 mol %, about 10 mol %, about 100 mol %, about 200 mol %, about 300 mol % or in excess based on a compound of Formula (A). A base should be included in a molar amount selected to react with each mole of protons generated by a reaction as provided herein, and preferably is included in about 100 mol % based on a compound of Formula (A). In some embodiments, a base can be Et$_3$N, Hunig's base, pyridine, piperidine, morpholine, Proton Sponge™, DBU, Na$_2$CO$_3$, K$_2$CO$_3$, Li$_2$CO$_3$, Cs$_2$CO$_3$, KOtBu, K$_2$HPO$_4$, Na$_2$HPO$_4$, Na$_3$PO$_4$, K$_3$PO$_4$, NaOH, KOH, CsOH, LiOH, KF, CsF, NaOAc, KOAc, CsOAc, LiOAc, LiOtBu, NaOtBu, NaHCO$_3$, KHCO$_3$, CsHCO$_3$ or LiHCO$_3$.

In some embodiments, a compound of Formula (A) can be represented by Formula (A1), Formula (A2), Formula (A3), Formula (A4), Formula (A5) Formula (A6) or Formula (A7), having the structures:

Formula (A1)

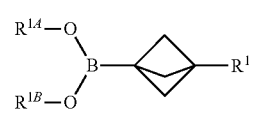

-continued

Formula (A2)
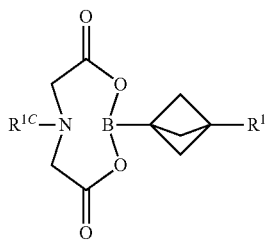

Formula (A3)
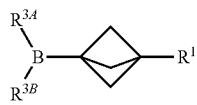

Formula (A4)
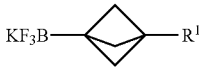

Formula (A5)
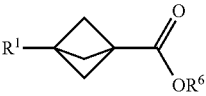

Formula (A6)
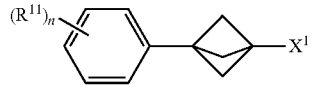

Formula (A7)
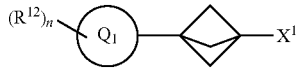

In various embodiments of such compounds of Formula (A), the variables $R^1$, $R^{1A}$, $R^{1B}$, $R^{1C}$, $R^{3A}$, $R^{3B}$, $R^6$, and $X^1$ can be as described elsewhere herein. Each $R^{11}$ and each $R^{12}$ in such compounds of Formula (A) can independently be D (deuterium), halogen, hydroxy, $C_{1-4}$ alkoxy, $C_{1-4}$ alkyl, $C_{3-10}$ cycloalkyl, an optionally substituted $C_{3-10}$ cycloalkenyl, aryl, heteroaryl, $C_{1-6}$ haloalkyl, cyano, alkenyl, alkynyl, cycloalkenyl, aryl(alkyl), heteroaryl(alkyl), heterocyclyl(alkyl), acyl, thiocarbonyl, O-carbamyl, N-carbamyl, O-thiocarbamyl, N-thiocarbamyl, C-amido, N-amido, C-thioamido, N-thioamido, S-sulfonamido, N-sulfonamido, C-carboxy, O-carboxy, sulfenyl, sulfinyl, sulfonyl, haloalkoxy, an amino, a mono-substituted amino group or a di-substituted amino group.

In an embodiment, the variable n in such compounds of Formula (A) is an integer from 0 to 4. In an embodiment, the variable $Q_1$ is an optionally substituted monocyclic or bicyclic heteroaryl or an optionally substituted monocyclic or bicyclic heterocyclyl including 0 to 4 heteroatom moieties selected from —N═, —N($R^{2B}$)—,

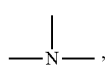

—O— and —S—. In an embodiment, each $R^{2B}$ can independently be D (deuterium), hydroxy, $C_{1-4}$ alkoxy, $C_{1-4}$ alkyl, $C_{3-10}$ cycloalkyl, aryl, heteroaryl, $C_{1-6}$ haloalkyl, alkenyl, alkynyl, cycloalkenyl, aryl(alkyl), heteroaryl(alkyl), heterocyclyl(alkyl), acyl, sulfenyl, sulfinyl, sulfonyl, an amino, a mono-substituted amino group or a di-substituted amino group.

In certain embodiments, a method for preparing a substituted bicyclo[1.1.1]pentane compound of Formula (I) includes reacting a compound of Formula (A1), Formula (A2), Formula (A3) or Formula (A4) with a compound of Formula (B). In further embodiments, a method for preparing a substituted bicyclo[1.1.1]pentane compound of Formula (I) includes reacting a compound of Formula (A5), Formula (A6) or Formula (A7) with a compound of Formula (B).

In various embodiments, a compound of Formula (A1) can be a compound of Formula (A1a), Formula (A1b), Formula (A1c) or Formula (A1d):

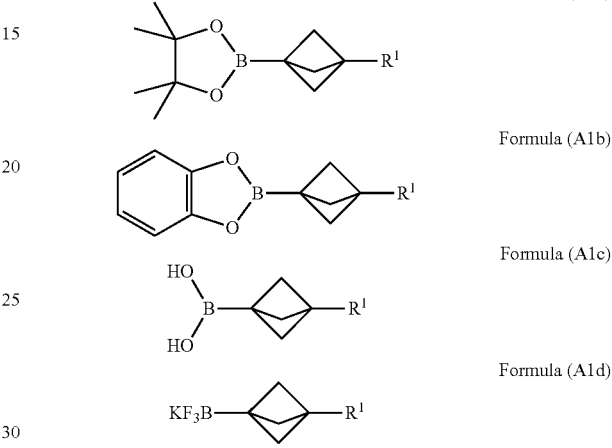

In some embodiments, $R^1$ of Formula (A1a), Formula (A1b), Formula (A1c) and/or Formula (A1d) can be selected from an optionally substituted $C_{1-30}$ alkyl, an optionally substituted $C_{2-30}$ alkenyl, an optionally substituted $C_{3-10}$ monocyclic cycloalkyl, an optionally substituted aryl, an optionally substituted heteroaryl, an optionally substituted heterocyclyl, a halogen, an optionally substituted C-carboxy, an amino, a mono-substituted amino, a di-substituted amino, an optionally substituted C-amido, an optionally substituted N-amido, an optionally substituted $C_{1-30}$ alkoxy, a hydroxy, an optionally substituted $C_{1-30}$ haloalkyl, a cyano, an optionally substituted S-sulfonamido, an optionally substituted N-sulfonamido, an optionally substituted O-carboxy, an optionally substituted $C_{2-30}$ alkynyl, an optionally substituted $C_{3-10}$ cycloalkenyl, an optionally substituted aryl(alkyl), an optionally substituted heteroaryl(alkyl), an optionally substituted heterocyclyl(alkyl), an optionally substituted acyl, an optionally substituted thiocarbonyl, an optionally substituted O-carbamyl, an optionally substituted N-carbamyl, an optionally substituted O-thiocarbamyl, an optionally substituted N-thiocarbamyl, an optionally substituted C-thioamido, an optionally substituted N-thioamido, an optionally substituted sulfenyl, an optionally substituted sulfinyl, an optionally substituted sulfonyl, an optionally substituted haloalkoxy, and a first boron-containing moiety, wherein the first boron-containing moiety is connected by the boron.

In some embodiments, $R^1$ of Formula (A1a), Formula (A1b), Formula (A1c) and/or Formula (A1d) can be an optionally substituted N-carbamyl, for example, —NH(C═O))O—($C_{1-4}$ alkyl). In other embodiments, $R^1$ of Formula (A1a), Formula (A1b), Formula (A1c) and/or Formula (A1d) can be an optionally substituted aryl, such as a substituted or unsubstituted phenyl. In still other embodiments, $R^1$ of Formula (A1a), Formula (A1b), Formula (A1c)

and/or Formula (A1d) can be an optionally substituted monocyclic heteroaryl, such as a substituted or unsubstituted 5- or 6-membered heteroaryl. In yet still other embodiments, R¹ of Formula (A1a), Formula (A1b), Formula (A1c) and/or Formula (A1d) can be an optionally substituted bicyclic heteroaryl, such as a substituted or unsubstituted 9- or 10-membered heteroaryl. In some embodiments, R¹ of Formula (A1a), Formula (A1b), Formula (A1c) and/or Formula (A1d) can be a first boron-containing moiety. Examples of the first boron-containing moiety for R¹ include, but are not limited to,

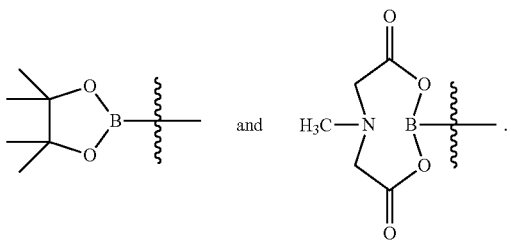

In some embodiments, a compound selected from Formula (A1a), Formula (A1b), Formula (A1c) and Formula (A1d), wherein the compound can be selected from:

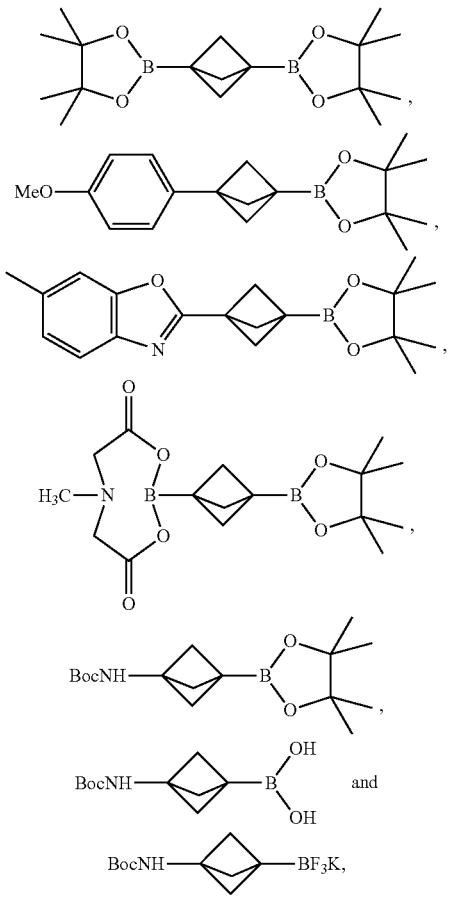

or a pharmaceutically acceptable salt of any of the foregoing.

In some embodiments of the reaction of the compound of Formula (A) with the compound of Formula (B) to form the compound of Formula (I), when a compound of Formula (A) is a compound of Formula (A1), Formula (A2), Formula (A3) or Formula (A4), the first transition metal catalyst can be a Suzuki coupling catalyst, the second transition metal catalyst is not present and $X^2$ can be a halide or pseudohalide. In some embodiments, when a compound of Formula (A) is a compound of Formula (A5), the first transition metal catalyst can be a Ni catalyst, the second transition metal catalyst can be present, the second transition metal catalyst can be a photoredox catalyst, and $X^2$ can be a halide or pseudohalide.

In some embodiments, a compound of Formula (B) can be represented by Formula (B1) or Formula (B2), having the structure:

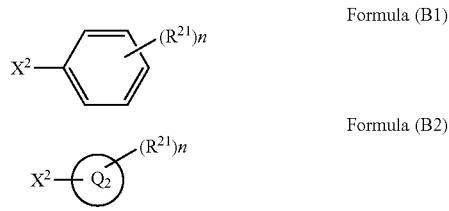

Formula (B1)

Formula (B2)

In various embodiments of such compounds of Formula (B), the variable $X^2$ can be as described elsewhere herein. Each $R^{21}$ in such compounds of Formula (B) can independently be D (deuterium), halogen, hydroxy, $C_{1-4}$ alkoxy, $C_{1-4}$ alkyl, $C_{3-10}$ cycloalkyl, an optionally substituted $C_{3-10}$ cycloalkenyl, aryl, heteroaryl, $C_{1-6}$ haloalkyl, cyano, alkenyl, alkynyl, cycloalkenyl, aryl(alkyl), heteroaryl(alkyl), heterocyclyl(alkyl), acyl, thiocarbonyl, 0-carbamyl, N-carbamyl, O-thiocarbamyl, N-thiocarbamyl, C-amido, N-amido, C-thioamido, N-thioamido, S-sulfonamido, N-sulfonamido, C-carboxy, O-carboxy, sulfenyl, sulfinyl, sulfonyl, haloalkoxy, an amino, a mono-substituted amino group or a di-substituted amino group. In various embodiments, n is an integer from 0 to 4. In various embodiments, $Q_2$ is an optionally substituted monocyclic or bicyclic heteroaryl or an optionally substituted monocyclic or bicyclic heterocyclyl including 0 to 4 heteroatom moieties selected from —N═, —N($R^{2B}$)—,

—O— and —S—. In various embodiments, each $R^{2B}$ can independently be D (deuterium), hydroxy, $C_{1-4}$ alkoxy, $C_{1-4}$ alkyl, $C_{3-10}$ cycloalkyl, aryl, heteroaryl, $C_{1-6}$ haloalkyl, alkenyl, alkynyl, cycloalkenyl, aryl(alkyl), heteroaryl(alkyl), heterocyclyl(alkyl), acyl, sulfenyl, sulfinyl, sulfonyl, an amino, a mono-substituted amino group or a di-substituted amino group.

In some embodiments of the compound of Formula (A), R¹ cannot be hydrogen. In additional embodiments, R¹ cannot be an unsubstituted phenyl. In other embodiments, R¹ cannot be a mono-substituted phenyl. In still other embodiments, R¹ cannot be a di-substituted phenyl. In various embodiments, R¹ cannot be a substituted or an unsubstituted alkyl. In further embodiments, R¹ cannot be a substituted or an unsubstituted alkenyl. In various embodiments, R¹ cannot be a substituted or unsubstituted heterocyclyl. In further embodiments, R¹ cannot be a substituted or an unsubstituted heteroaryl. In certain embodiments, R[1] cannot be substituted by a substituted or an unsubstituted $C_{1-4}$ alkyl. In some embodiments, R[1] cannot be an optionally substituted C-carboxy, for example —C(=O)O(an unsubstituted $C_{1-4}$ alkyl). In some embodiments, R[1] cannot be an optionally substituted C-carboxy, for example —C(=O)OCH$_3$.

Starting materials, including compounds of Formula (A) and compounds of Formula (B), can be prepared by any suitable method. A person of skill in the art informed by the guidance provided herein has knowledge and skills to prepare such compounds by various available methods. Regarding compounds of Formula (A), see, for example, WO 2015/089170; WO 2015/134710; U.S. Pat. No. 5,405,550; Levin et al., Chem. Rev. (2000), Vol. 100, 169-234; Bunker et al., Org. Lett. (2011), Vol. 13(17), 4746-4748; Atack, T. C., et al., J. Am. Chem. Soc. (2014), Vol. 136 (27), 9521-9523; and Atack, T. C., et al., J. Am. Chem. Soc. (2016), Vol. 138 (19), 6139-6142. Any preliminary reaction steps used to form starting compounds of the Formula (A) can be readily carried out by those skilled in the art. Methods and techniques useful for the preparation of compounds of Formula (B) are also well known to those of skill in the art. (see, for example, March, J., Advanced Organic Chemistry: Reactions, Mechanisms, and Structure (6th Ed., Wiley, John & Sons, Inc., January 2007); Larock, R. C., Comprehensive Organic Transformations, A Guide to Functional Group Preparations (Wiley 1999, 2nd Ed.)).

In certain embodiments, a compound of Formula (A) or a compound of Formula (B) can be present as a salt.

In some embodiments, a compound described herein can be selected from:

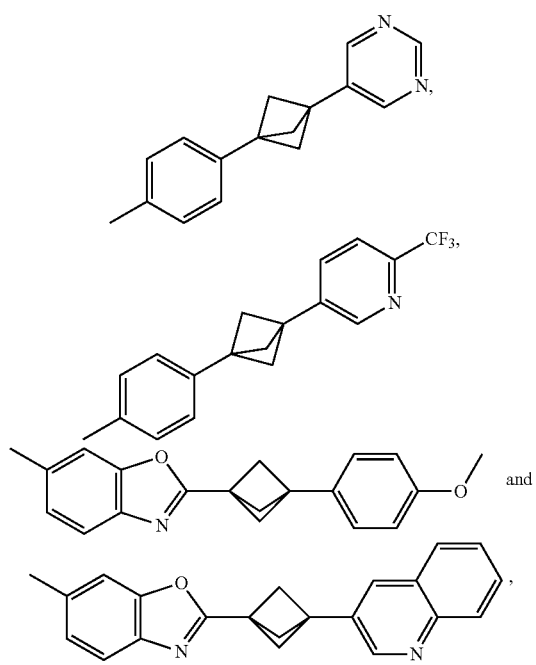

or a pharmaceutically acceptable salt of any of the foregoing.

The methods provided herein can be carried out in various ways by those skilled in the art as guided by the detailed teachings provided herein. Generally, unless provided otherwise, components, for example, a compound of Formula (A), a compound of Formula (B), a first transition metal catalyst, optionally a second transition metal catalyst, and optionally a base, can be combined into a reaction mixture with one or more solvents, and the reaction mixture exposed to conditions of temperature and pressure, as guided by the teachings herein. Physical agitation such as stirring of the reaction mixture is preferred. Components of a reaction mixture are generally in a solution state, but can be suspended in a solvent, or may be partially dissolved and partially suspended. In particular, a compound of Formula (A), a compound of Formula (B), a first transition metal catalyst, and optionally a second transition metal catalyst are preferably to be dissolved. A component, for example, a catalyst, can be bound to a polymer or adsorbed on a solid medium, for example, silica, alumina, charcoal and the like.

Routine experimentation informed by the guidance provided herein can be used to select the sequence of mixing of components and application of conditions to give rise to a desired coupling reaction. Generally, the order of addition of various components to a reaction mixture is not critical to achieving a coupling reaction, however, generally a coupling will proceed when the compound of Formula (A), compound of Formula (B), the first transition metal catalyst and optionally the second transition metal catalyst are combined in a reaction mixture. A compound of Formula (A) or Formula (B), a first transition metal catalyst, a second transition metal catalyst and a base can be added to a reaction mixture as a solid, an oil, a solution or in any suitable manner. A component is generally added at once, but may be added portionwise during the course of a reaction.

The reactions described herein can be performed at various temperatures. In some embodiments, a method provided herein is performed at room temperature, about 0° C., about 20° C., about 40° C., about 60° C., about 80° C., about 100° C., about 120° C., about 140° C., about 160° C., about 180° C., about 200° C. or values there between. Preferred temperatures are typically in the range of from room temperature to about 80° C. Such a temperature is measured at a heating or cooling source. Generally, temperature will vary during the course of a reaction, but the highest temperature reached is taken to be the temperature of the reaction.

A reaction described herein should generally be performed for the length of time necessary to secure a desired amount of a reaction product. The formation of a desired product, such as a compound of Formula (I), can be monitored by any suitable analytical method. Generally, a reaction time will require a few minutes to a few days.

A person of skill in the art, guided by the teachings provided herein, can select the molar ratios of various reaction components in the practice of the methods described herein. In certain embodiments, one or more of the compound of Formula (A) and the compound of Formula (B) can be present in a molar ratio of about 1.1:1, about 1.5:1, about 2:1, about 3:1, about 0.9:1, about 0.7:1, about 0.5:1, about 0.3:1, about 0.1:1 or values there between, with respect to each other. In further embodiments, a compound of Formula (A) and a compound of Formula (B) can be included in a molar ratio of about 1:1.

Generally, reacting is conducted under an inert atmosphere such as a nitrogen or argon atmosphere. In some embodiments, reacting takes place in a medium substantially free from oxygen, where substantially free is determined by that needed to ensure the stability of an included catalyst or other component.

A person of skill in the art can select an appropriate solvent based on available knowledge and the detailed teachings herein. Generally, an aprotic solvent is preferred. In some embodiments, the solvent can include an ether, such as tetrahydrofuran, a sulfoxide, such as dimethylsulfoxide, an amide, such as dimethylformamide or N-methyl pyrrolidinone, an alkyl halide, such as dichloromethane, an optionally substituted benzene, such as toluene, a nitrile, such as acetonitrile, an ester, such as ethyl acetate, an optionally substituted alkane, such as heptane, an alcohol, such as ethanol, or a combination of these. In some embodiments, a solvent can be selected from dimethylformamide, acetonitrile or tetrahydrofuran.

In some embodiments, an oxidating or reducing agent can be included in a reaction mixture. An oxidating or reducing agent, when included, can, for example, restore a catalyst to its active state or modulate the oxidation state of a moiety in a compound of Formula (A), Formula (B), or Formula (I).

In some embodiments, a water scavenger can be included in a reaction mixture. Suitable scavengers include, for example, solution phase scavengers such as a trialkyl orthoformate or solid phase scavengers such as molecular sieves, zeolites, and the like. In some embodiments, reacting takes place in a medium substantially free of water, where substantially free is determined by that needed to prevent reduction in reaction yield due to the presence of water.

In some embodiments, stepwise or multistep reaction may be appropriate. For example, without limitation, a catalyst may be chemically modified with one or more ligands before being combined with other components of a reaction. As additional examples, protecting group manipulation, ligand exchange, oxidation state manipulation or pseudohalide formation followed by coupling in a single vessel is provided. In particular, a carboxylate moiety may be chemically transformed in situ. For example, a carboxylic acid can be deprotonated, or an ester, thioester, or acyl halide can be hydrolyzed, to form a carboxylate anion. In some embodiments, where $X^1$ or $X^2$ is —C(=O)Y and Y is OM, $X^1$ or $X^2$ can be formed. Further examples of suitable transformations are provided in Richard C. Larock Comprehensive Organic Transformations: A Guide to Functional Group Preparations (2nd Ed., Wiley, John & Sons, Inc., November 1999); and Jerry March, (Advanced Organic Chemistry: Reactions, Mechanisms, and Structure (6th Ed., Wiley, John & Sons, Inc., January 2007).

In some embodiments, a compound of Formula (I) can be an oligomer or a polymer.

Further processing may be desired to isolate and/or purify a compound of Formula (I). Routine experimentation informed by the guidance provided herein may be used to identify appropriate isolation and/or purification conditions. For example, standard methods such as partitioning a reaction mixture between solvents of disparate hydrophobicities, for example extraction, precipitation, for example crystallization, distillation and chromatography are available. Those of skill in the art have knowledge and skills available that allow them to isolate and/or purify compounds of Formula (I) using routine experimentation guided by the teachings provided herein.

In some embodiments, a compound of Formula (I) is prepared in at least about 10%, at least about 20%, at least about 30%, at least about 40%, at least about 50%, at least about 60%, at least about 70%, at least about 80% or at least about 90% yield, based on the starting compound of Formula (A).

A compound of Formula (I) may be used in any suitable application, for example, in an agricultural product, a medicament, a material, and/or scientific research.

Pharmaceutical Compositions

Some embodiments described herein relate to a pharmaceutical composition, that can include an effective amount of one or more compounds described herein (e.g., a compound of Formula (I), or a pharmaceutically acceptable salt thereof) and a pharmaceutically acceptable carrier, diluent, excipient or combination thereof.

The term "pharmaceutical composition" refers to a mixture of one or more compounds and/or salts disclosed herein with other chemical components, such as diluents or carriers. The pharmaceutical composition facilitates administration of the compound to an organism. Pharmaceutical compositions will generally be tailored to the specific intended route of administration. In some instances, salts can be obtained by reacting compounds with inorganic or organic acids such as hydrochloric acid, hydrobromic acid, sulfuric acid, nitric acid, phosphoric acid, methanesulfonic acid, ethanesulfonic acid, p-toluenesulfonic acid, and salicylic acid.

The term "physiologically acceptable" defines a carrier, diluent or excipient that does not abrogate the biological activity and properties of the compound nor cause appreciable damage or injury to an animal to which delivery of the composition is intended.

As used herein, a "carrier" refers to a compound that facilitates the incorporation of a compound into cells or tissues. For example, without limitation, dimethyl sulfoxide (DMSO) is a commonly utilized carrier that facilitates the uptake of many organic compounds into cells or tissues of a subject.

As used herein, a "diluent" refers to an ingredient in a pharmaceutical composition that lacks appreciable pharmacological activity but may be pharmaceutically necessary or desirable. For example, a diluent may be used to increase the bulk of a potent drug whose mass is too small for manufacture and/or administration. It may also be a liquid for the dissolution of a drug to be administered by injection, ingestion or inhalation. A common form of diluent in the art is a buffered aqueous solution such as, without limitation, phosphate buffered saline that mimics the pH and isotonicity of human blood.

As used herein, an "excipient" refers to an essentially inert substance that is added to a pharmaceutical composition to provide, without limitation, bulk, consistency, stability, binding ability, lubrication, disintegrating ability etc., to the composition. A "diluent" is a type of excipient.

The pharmaceutical compositions described herein can be administered to a human patient per se, or in pharmaceutical compositions where they are mixed with other active ingredients, as in combination therapy, or carriers, diluents, excipients or combinations thereof. Proper formulation is dependent upon the route of administration chosen. Techniques for formulation and administration of the compounds described herein are known to those skilled in the art.

The pharmaceutical compositions disclosed herein may be manufactured in a manner that is itself known, e.g., by means of conventional mixing, dissolving, granulating, dragee-making, levigating, emulsifying, encapsulating, entrapping or tableting processes. Additionally, the active ingredients are contained in an amount effective to achieve its intended purpose. Many of the compounds used in the pharmaceutical combinations disclosed herein may be provided as salts with pharmaceutically compatible counterions.

Multiple techniques of administering a compound, salt and/or composition exist in the art including, but not limited to, oral, rectal, pulmonary, topical, aerosol, injection, infusion and parenteral delivery, including intramuscular, subcutaneous, intravenous, intramedullary injections, intrathecal, direct intraventricular, intraperitoneal, intranasal and intraocular injections.

One may also administer the compound, salt and/or composition in a local rather than systemic manner, for example, via injection or implantation of the compound directly into the affected area, often in a depot or sustained release formulation. Furthermore, one may administer the compound in a targeted drug delivery system, for example, in a liposome coated with a tissue-specific antibody. The liposomes will be targeted to and taken up selectively by the organ. For example, intranasal or pulmonary delivery to target a respiratory disease or condition may be desirable.

The compositions may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration. The pack or dispenser may also be accompanied with a notice associated with the container in form prescribed by a governmental agency regulating the manufacture, use, or sale of pharmaceuticals, which notice is reflective of approval by the agency of the form of the drug for human or veterinary administration. Such notice, for example, may be the labeling approved by the U.S. Food and Drug Administration for prescription drugs, or the approved product insert. Compositions that can include a compound and/or salt described herein formulated in a compatible pharmaceutical carrier may also be prepared, placed in an appropriate container, and labeled for treatment of an indicated condition.

EXAMPLES

Additional embodiments are disclosed in further detail in the following examples, which are not in any way intended to limit the scope of the claims.

Compounds

Table 1 provides compounds of Formula (I) prepared by the methods disclosed herein.

TABLE 1

| # | $R^1$ | $X^1$ | $R^2$ | $X^2$ | Catalyst(s) |
|---|---|---|---|---|---|
| 1 | pinacol boronate | pinacol boronate | 4-MeO-phenyl | Br | $Pd(PPh_3)_4$ |
| 2 | 4-methylphenyl | –C(O)OH | pyrimidin-5-yl | Br | $Ir[dF(CF_3)ppy]_2(dtbpy)PF_6$, $NiCl_2 \cdot DME$ |
| 3 | 4-methylphenyl | –C(O)OH | 2-$CF_3$-pyridin-5-yl | Br | $Ir[dF(CF_3)ppy]_2(dtbpy)PF_6$, $NiCl_2 \cdot DME$ |
| 4 | 6-methylbenzoxazol-2-yl | pinacol boronate | 4-MeO-phenyl | Br | $Pd(PPh_3)_4$ |
| 5 | 6-methylbenzoxazol-2-yl | pinacol boronate | quinolin-3-yl | Br | $Pd(dppf)Cl_2$ |
| 6 | $MeO_2C$– | phthalimido ester | 4-methylphenyl | MgBr | $NiCl_2 \cdot DME$ |

Example 1

Preparation of Compound 1

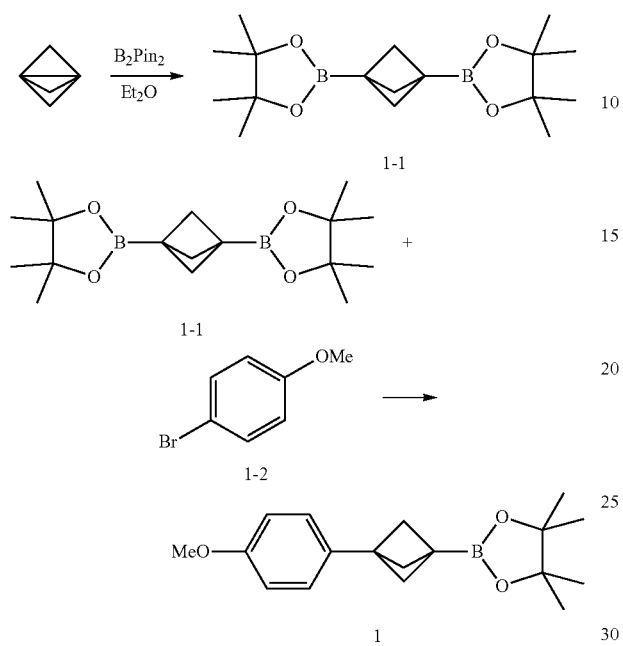

A vial containing a solution of [1.1.1]propellane (0.25M in $Et_2O$) was treated with bis(pinacolato)diboron (120 mol %) at room temperature (RT) and sealed under an atmosphere of $N_2$. After 3 days, the reaction was filtered and the collected solid was washed with $Et_2O$ and dried in vacuo to provide compound 1-1 as a white solid. $^1$H NMR (400 MHz, $CDCl_3$) δ 2.03 (s, 6H), 1.22 (s, 24H).

To a flame dried vial with stir bar was added compound 1-1, followed by $Pd(PPh_3)_4$ (20 mol %), and 4-bromoanisole 1-2 (120 mol %). The reaction vial was purged with $N_2$, and THF (0.08 M in compound 1-1) followed by tBuOK (1M in THF, 300 mol %) was added. The mixture was heated at 85° C. for 20 h. The reaction was cooled to RT, and concentrated in vacuo to provide the crude product. Purification of the crude product by column chromatography ($SiO_2$, Hexanes/EtOAc) afforded compound 1 as a white solid. $^1$H NMR (400 MHz, $CDCl_3$) δ 7.12 (d, J=8.6 Hz, 2H), 6.83 (d, J=8.7 Hz, 2H), 3.78 (s, 3H), 2.13 (s, 6H), 1.26 (s, 12H).

Example 2

Preparation of Compound 2

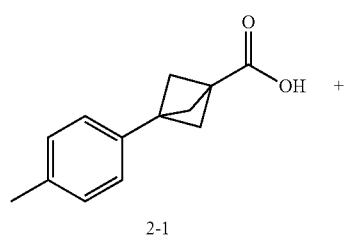

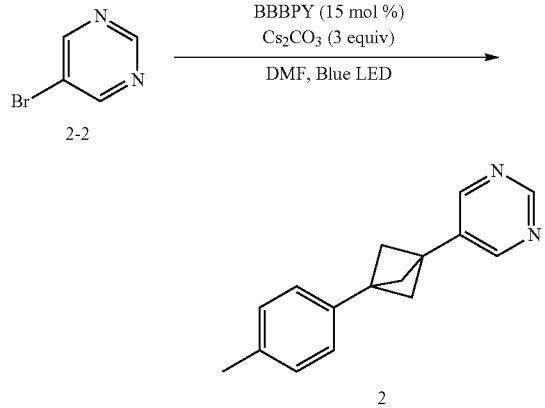

An oven dried vial containing a stir bar was charged with 5-bromopyrimidine 2-2, compound 2-1 (300 mol %), 4,4'-di-tert-butyl-2,2'-bipyridine (15 mol %), nickel(II) chloride (dimethoxyethane adduct) (10 mol %), cesium carbonate (300 mol %), Iridium catalyst [Ir{dF($CF_3$)ppy}$_2$(dtbpy)]$PF_6$ (1 mol %), and DMF (0.02M in compound 2-2). The solution was degassed via freeze-pump-thaw cycle (3×) then irradiated with a 3 W blue LED light for 4 h. The mixture was diluted with water and extracted with EtOAc (4×). The combined organics were dried ($Na_2SO_4$) and concentrated to provide the crude product which was further purified by column chromatography ($SiO_2$, EtOAc/Hexanes) to afford compound 2 as a pale yellow residue. $^1$H NMR (400 MHz, $CDCl_3$) δ 9.21 (s, 1H), 8.71 (d, J=5.3 Hz, 1H), 7.34 (d, J=5.3 Hz, 1H), 7.17 (m, 2H), 7.11 (m, 2H), 2.45 (s, 6H), 2.35 (s, 3H); LC/MS (APCI) m/z 237.1 $[C_{16}H_{16}N_2+H]^+$.

Example 3

Preparation of Compound 3

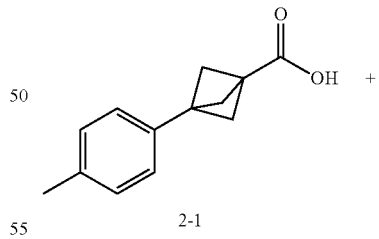

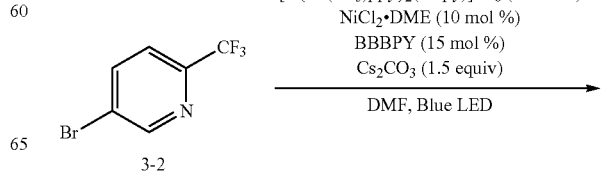

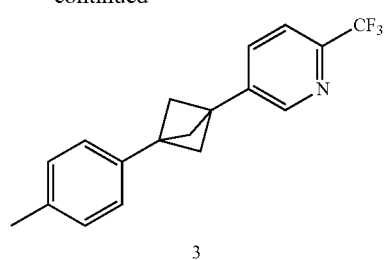

3

An oven dried vial containing a stir bar was charged with compound 3-2, compound 2-1 (150 mol %), 4,4'-di-tert-butyl-2,2'-bipyridine (15 mol %), nickel(II) chloride (dimethoxyethane adduct) (10 mol 1%), cesium carbonate (150 mol %), iridium catalyst [Ir{dF(CF$_3$)ppy}$_2$(dtbpy)]PF$_6$ (1 mol %), and DMF (0.02 M in compound 3-2). The solution was degassed via freeze-pump-thaw cycle (3×) then irradiated with a 3 W blue LED light for 4 h. The mixture was diluted with water and extracted with EtOAc (4×). The combined organics were dried (Na$_2$SO$_4$) and concentrated to provide the crude product which was further purified by column chromatography (SiO$_2$, EtOAc/Hexanes) to afford compound 3 as a pale yellow residue. $^1$H NMR (400 MHz, CDCl$_3$) δ 8.66 (d, J=5.0 Hz, 1H), 7.56 (s, 1H), 7.37 (d, J=4.9 Hz, 1H), 2.37 (s, 6H), 2.35 (s, 3H); LC/MS (APCI) m/z 304.1 [C$_{18}$H$_{16}$F$_3$N+H]$^+$.

Example 4

Preparation of Compound 4

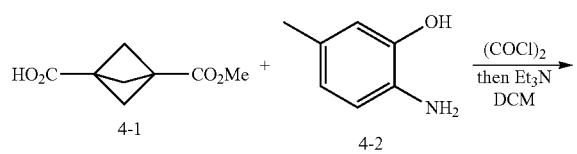

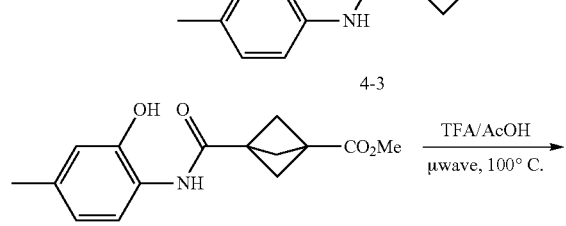

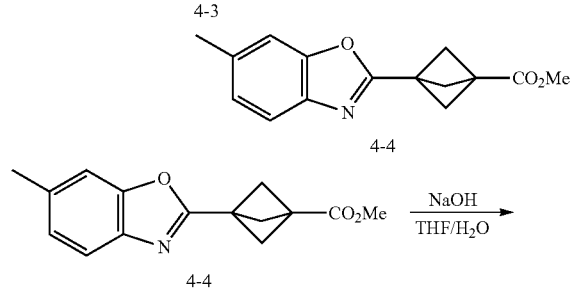

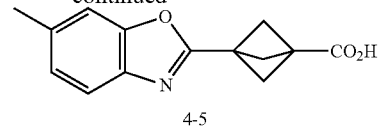

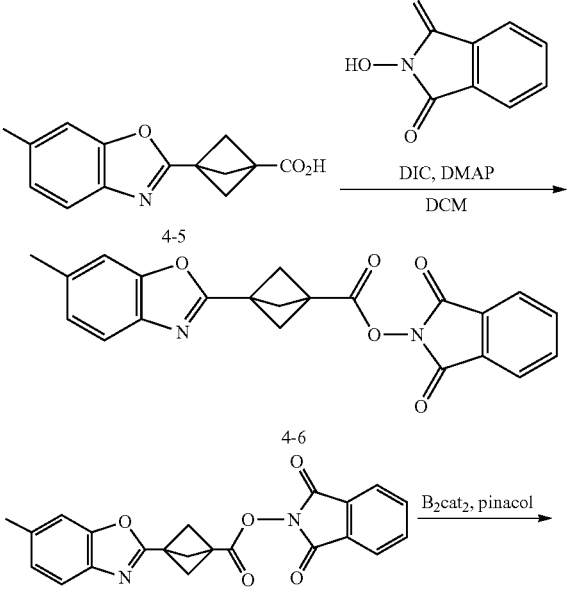

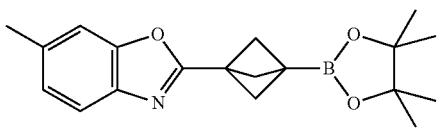

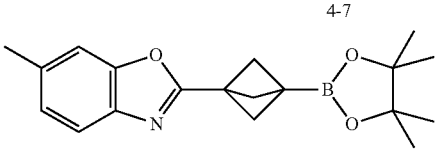

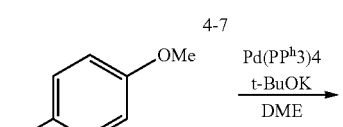

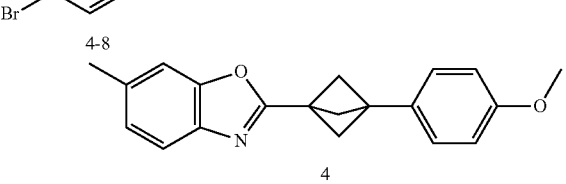

A solution of compound 4-1 (2.00 g, 11.8 mmol) in DCM (23.5 mL) was treated with 2 drops of DMF and cooled to 0° C. Oxalyl chloride (1.21 mL, 14.1 mmol) was added slowly, and the resulting solution was allowed to stir at RT for 2 h. The solution was concentrated under reduced pressure to provide the acid chloride which was dissolved in DCM (58.8 ml) and cooled to 0° C. The solution was treated with Et$_3$N (4.91 mL, 35.3 mmol) followed by compound 4-2 (1.45 g, 11.8 mmol). The mixture was stirred at RT for 2 h then concentrated under reduced pressure to provide compound 4-3 which was used without further purification. LC/MS (APCI) m/z 276.1 [C$_{15}$H$_{17}$NO$_4$+H]$^+$.

A solution of crude compound 4-3 in AcOH (19.6 mL) and TFA (19.6 mL) was divided into 2 microwave vials and each was irradiated at 100° C. for 70 mins. The contents of the two vials were recombined and concentrated under reduced pressure to provide the crude product which was further purified and purified by column chromatography (SiO$_2$, EtOAc/Hexanes) to provide compound 4-4, which was used without further purification. $^1$H NMR (400 MHz, CDCl$_3$) δ 7.69 (d, J=8.3 Hz, 1H), 7.35 (m, 1H), 7.24-7.22 (m, 1H), 3.76 (s, 3H), 2.63 (s, 6H), 2.50 (s, 3H); LC/MS (APCI) m/z 258.1 [C$_{15}$H$_{15}$NO$_3$+H]$^+$.

A solution of semi-crude compound 4-4 (3.03 g, 11.8 mmol) in THF (29.4 mL) was treated with 2 M NaOH (17.7 mL, 35.3 mmol). The mixture was stirred at RT for 2 h. The volatiles were then removed under reduced pressure. The basic aqueous layer was washed with EtOAc (1×20 mL) and then the aqueous layer was acidified with 1 N HCl. The resultant white precipitate was collected by filtration. The filter cake was washed with H$_2$O (20 mL) and dried to afford compound 4-5 as a beige solid. $^1$H NMR (400 MHz, DMSO-d$_6$) δ 12.68 (s, 1H), 7.56 (d, J=8.2 Hz, 1H), 7.50 (s, 1H), 7.18 (d, J=7.9 Hz, 1H), 2.45 (s, 6H), 2.43 (s, 3H); LC/MS (APCI) m/z 244.1 [C$_{14}$H$_{13}$NO$_3$+H]$^+$.

Compound 4-5 (1.98 g, 8.13 mmol), NHPI (1.33 g, 8.13 mmol) and DMAP (0.099 g, 0.813 mmol) were added to a vial and suspended in anhydrous DCM (81 mL). DIC (1.26 mL, 8.13 mmol) was added, and the resulting solution was stirred at RT overnight. The mixture was concentrated under reduced pressure. The resultant residue was deposited onto Celite and further purified by column chromatography (SiO$_2$, Hexanes/EtOAc) to provide compound 4-6 as an off-white solid. $^1$H NMR (400 MHz, DMSO-d$_6$) δ 7.97-7.86 (m, 2H), 7.85-7.80 (m, 2H), 7.57 (d, J=8.1 Hz, 1H), 7.31 (s, 1H), 7.15 (d, J=8.2 Hz, 1H), 2.81 (s, 6H), 2.49 (s, 3H); LC/MS (APCI) m/z 389.0 [C$_{22}$H$_{16}$N$_2$O$_5$+H]$^+$.

A vial containing a solution of compound 4-6 (1.20 g, 3.09 mmol) and B$_2$cat$_2$ (0.92 g, 3.86 mmol) in DMA (31 mL) was purged with N$_2$ for 10 min, sealed and then irradiated by a blue LED strip surrounding the vial. After 40 h, triethylamine (12.1 mL, 87.0 mmol) was added to the mixture followed by pinacol (1.46 g, 12.4 mmol). After 3 h, the mixture was concentrated and purified by column chromatography (SiO$_2$, EtOAc/Hexanes) to afford compound 4-7 as a white solid. $^1$H NMR (400 MHz, CDCl$_3$) δ 7.53 (d, J=8.1 Hz, 1H), 7.27 (br s, 1H), 7.10 (d, J=8.1 Hz, 1H), 2.46 (s, 3H), 2.40 (s, 6H), 1.27 (s, 12H).

To a vial with stir bar was added compound 4-7 (50.0 mg, 0.15 mmol), followed by Pd(PPh$_3$)$_4$(17.8 mg, 0.015 mmol), and 4-bromoanisole 4-8 (38.0 µL, 0.31 mmol). The reaction vial was purged with N$_2$, and DME (1.1 mL) followed by tBuOK (0.46 mL, 0.46 mmol, 1M in tBuOH) were added. The mixture was heated at 85° C. for 20 h. The reaction was cooled to RT, and concentrated to provide the crude product. Purification of the crude product by column chromatography (SiO$_2$, Hexanes/EtOAc) afforded compound 4 as a white solid. $^1$H NMR (400 MHz, CDCl$_3$) δ 7.56 (d, J=8.0 Hz, 1H), 7.31-7.29 (m, 1H), 7.23-7.20 (m, 2H), 7.14-7.11 (m, 1H), 6.90-6.86 (m, 2H), 3.81 (s, 3H), 2.54 (s, 6H), 2.48 (s, 3H). LC/MS (APCI) m/z 306.1 [C$_{20}$H$_{19}$NO$_2$+H]$^+$.

Example 5

Preparation of Compound 5

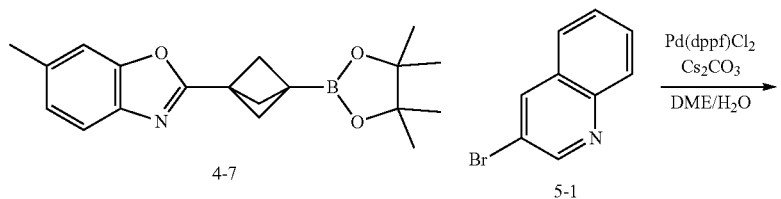

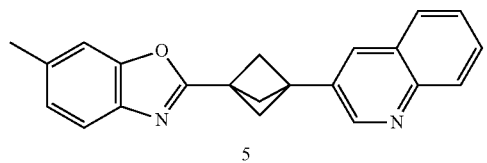

To a vial with stir bar was added compound 4-7 (100 mg, 0.31 mmol), followed by Cs$_2$CO$_3$ (301 mg, 0.92 mmol), Pd(dppf)Cl$_2$ (45.0 mg, 0.061 mmol) and 2-bromoquinoline 5-1 (84.0 µL, 0.62 mmol). The reaction vial was purged with N$_2$, and DME (2.8 mL) followed by H$_2$O (0.28 mL) were added. The mixture was heated at 85° C. for 20 h. The mixture was cooled to RT, and concentrated to provide the crude product. Purification of the crude product by column chromatography (SiO$_2$, Hexanes/EtOAc) followed by reverse phase column chromatography (C18, H$_2$O/CH$_3$CN) afforded compound 5 as a white solid. $^1$H NMR (400 MHz, CDCl$_3$) δ 8.89 (d, J=2.2 Hz, 1H), 8.11 (d, J=8.8 Hz, 1H), 8.00 (ap dd, J=2.2, 0.8 Hz, 1H), 7.83-7.81 (m, 1H), 7.70 (ddd, J=8.4, 6.9, 1.5 Hz, 1H), 7.58 (d, J=8.1 Hz, 1H), 7.56

(ddd, J=8.4, 7.0, 1.3 Hz, 1H), 7.33-7.32 (m, 1H), 7.17-7.14 (m, 1H), 2.73 (s, 6H), 2.50 (s, 3H). LC/MS (APCI) m/z 327.1 $[C_{22}H_{18}N_2O+H]^+$.

Example 6

Preparation of Compound 6

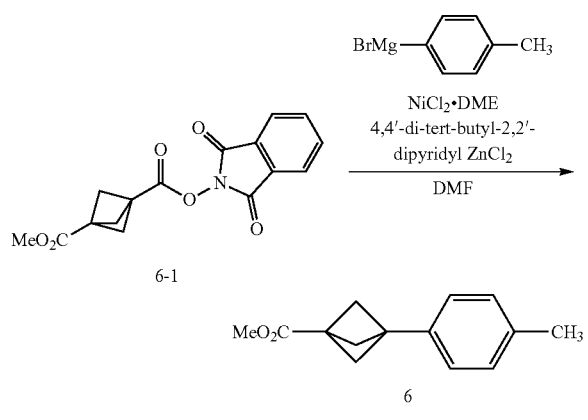

A vial was charged with NiCl$_2$*DME (0.028 g, 0.127 mmol), 4,4'-di-tert-butyl-2,2'-bipyridine (0.068 g, 0.254 mmol), and compound 6-1 (0.200 g, 0.634 mmol) then flushed with N$_2$. Anhydrous DMF (2.53 ml) was added, and the mixture was stirred for 2 mins prior to the addition of the arylzinc reagent. In a separate vial, the arylzinc reagent was prepared by adding a solution of p-tolylmagnesium bromide solution (1.90 mL, 1.90 mmol) to a solution of ZnCl$_2$ (1 M in diethyl ether) (1.90 mL, 1.90 mmol), and the mixture was allowed to stir for 10 mins. The arylzinc solution was then added to the vial containing the catalyst solution in one portion. The resulting mixture was allowed to stir at RT overnight. The mixture was concentrated and purified by column chromatography (SiO$_2$, EtOAc/Hexanes) to afford compound 6 as an off-white solid. $^1$H NMR (400 MHz, CDCl$_3$) δ 7.12 (s, 4H), 3.71 (s, 3H), 2.33 (s, 3H), 2.30 (s, 3H); LC/MS (APCI) m/z 217.1 $[C_{14}H_{16}O_2+H]^+$.

Table 2 provides compounds of Formula (A) prepared by the methods disclosed herein.

TABLE 2

| # | R$^1$ | X$^1$ |
|---|---|---|
| 7 | 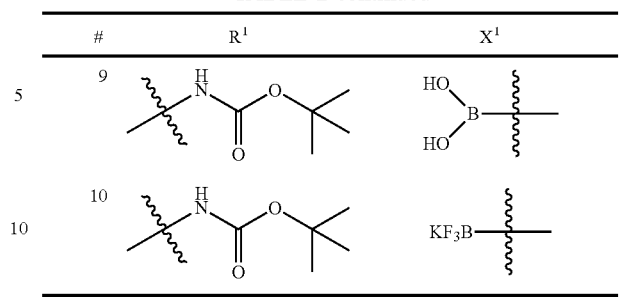 | |
| 8 | | |
| 9 | | |
| 10 | | |

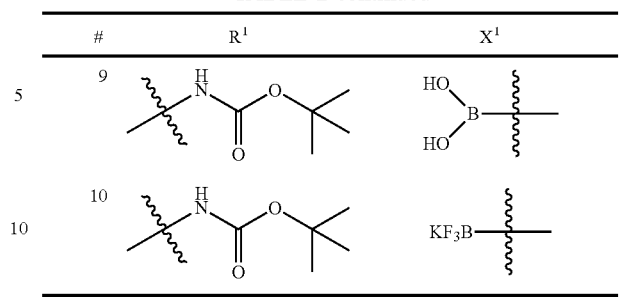

Example 7

Preparation of Compound 7

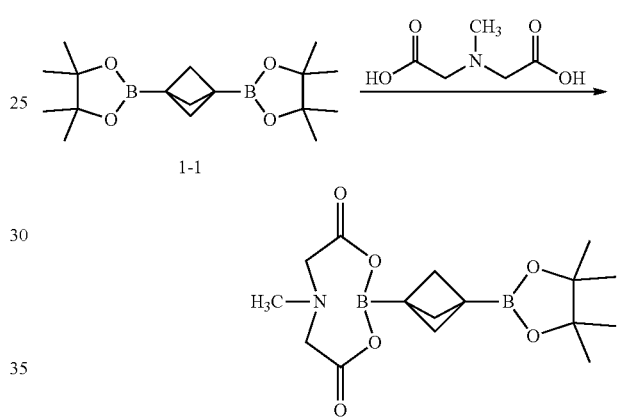

A heterogeneous solution of compound 1-1 (150 mg, 0.47 mmol) and N-methyliminodiacetic acid (103 mg, 0.7 mmol) in DMSO (4.7 mL), and 1,2-DCE (2.0 mL) was heated at 120° C. in a Biotage® Initiator+ Microwave Reactor for 1 h. The reaction was then cooled to RT, diluted with water and extracted with EtOAc (3×). The combined organic layers were dried (MgSO$_4$), and concentrated to provide the crude product which was further purified by column chromatography (SiO$_2$, DCM/CH$_3$CN) to afford compound 7 as a white solid. $^1$H NMR (400 MHz, CDCl$_3$) δ 3.75 (d, J=16.1 Hz, 2H), 3.61 (d, J=16.0 Hz, 2H), 2.98 (s, 3H), 2.00 (s, 6H), 1.22 (s, 12H).

Example 8

Preparation of Compound 8

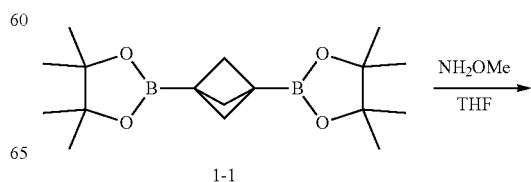

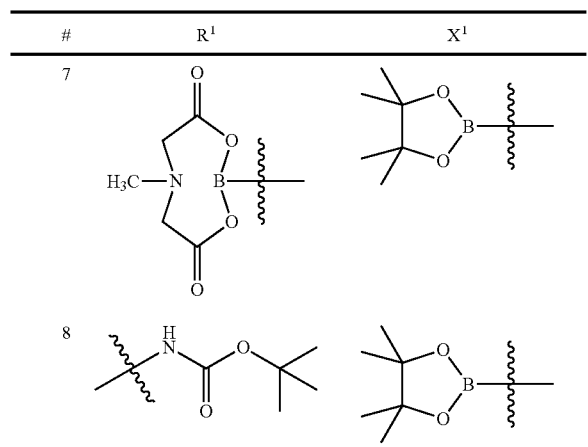

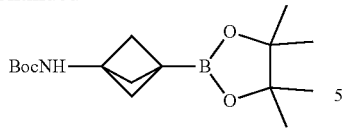

8

A solution of methoxyamine (1.91 mL, 1.88 mmol, 0.98 M in THF) was diluted with THF (4 mL), cooled to −78° C. and treated with t-BuLi (1.14 mL, 1.94 mmol, 1.7 M in pentane). After 30 min, compound 1-1 (200 mg, 0.63 mmol) was added in a single portion to the reaction mixture. After 5 min, the reaction was sealed, warmed to RT and then heated to 60° C. After 16 h the reaction was cooled to RT and treated with Boc anhydride (477 mg, 2.19 mmol). After 1 h, DCM was added to the reaction, and the reaction was filtered over a plug of Celite. The Celite plug was washed with DCM, and the combined filtrates were concentrated to provide the crude product. Purification of the crude product by column chromatography (SiO$_2$, Hexanes/EtOAc) afforded compound 8 as a white solid. $^1$H NMR (400 MHz, CDCl$_3$) δ 4.85 (s, 1H), 2.07 (s, 6H), 1.44 (s, 9H), 1.24 (s, 12H).

Example 9

Preparation of Compound 9

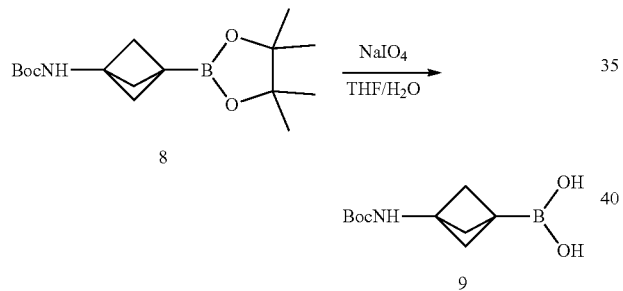

A solution of compound 8 (127.9 mg, 0.41 mmol) in THF (2.2 mL) and H$_2$O (0.55 mL) was treated with sodium periodate (265 mg, 1.241 mmol). After 5 min, 1 N HCl(aq) (0.83 mL) was added. After 1 h the reaction was extracted with EtOAc (2×), and the combined organic layers were washed with water, and concentrated to provide compound 9 as a white solid. $^1$H NMR (400 MHz, DMSO-d$_6$) δ 1.84 (s, 6H), 1.37 (s, 9H).

Example 10

Preparation of Compound 10

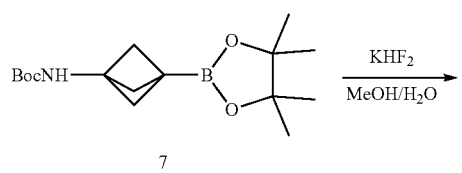

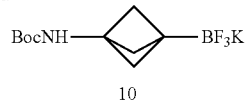

10

A solution of compound 7 (290.4 mg, 0.94 mmol) in MeOH (6.5 mL) was treated with KHF$_2$ (1.69 mL, 4.23 mmol, 2.5M in H$_2$O) at RT. After 2 h, the reaction was concentrated, dissolved in 1:1 MeOH: H$_2$O (8 mL) and the re-concentrated. This process was repeated 1 additional time. Acetone was then added to the reaction mixture. The reaction was filtered, and the collected solid was washed with additional acetone. The combined filtrate was concentrated to provide a white solid that was then washed with Et$_2$O to remove residual pinacol to provide compound 10 as a white solid. $^1$H NMR (400 MHz, DMSO-d$_6$) δ 1.46 (s, 6H), 1.35 (s, 9H); $^{19}$F NMR (376 MHz, DMSO-d$_6$, unreferenced) 6-141.09.

Furthermore, although the foregoing has been described in some detail by way of illustrations and examples for purposes of clarity and understanding, it will be understood by those of skill in the art that numerous and various modifications can be made without departing from the spirit of the present disclosure. Therefore, it should be clearly understood that the forms disclosed herein are illustrative only and are not intended to limit the scope of the present disclosure, but rather to also cover all modification and alternatives coming with the true scope and spirit of the invention.

What is claimed is:

1. A method for preparing a substituted bicyclo[1.1.1] pentane compound of Formula (I), comprising:
   reacting a compound of Formula (A) with a compound of Formula (B) in the presence of a first transition metal catalyst, optionally a second transition metal catalyst, and optionally a base, under conditions selected to form a compound of Formula (I);
   wherein the compound of Formula (A) has the structure:

(A)

wherein R$^1$ is selected from the group consisting of hydrogen, an optionally substituted C$_{1-30}$ alkyl, an optionally substituted C$_{2-30}$ alkenyl, an optionally substituted C$_{3-10}$ monocyclic cycloalkyl, an optionally substituted aryl, an optionally substituted heteroaryl, an optionally substituted heterocyclyl, a halogen, an optionally substituted C-carboxy, an amino, a monosubstituted amino, a di-substituted amino, an optionally substituted C-amido, an optionally substituted N-amido, an optionally substituted C$_{1-30}$ alkoxy, a hydroxy, an optionally substituted C$_{1-30}$ haloalkyl, a cyano, an optionally substituted S-sulfonamido, an optionally substituted N-sulfonamido, an optionally substituted O-carboxy, an optionally substituted C$_{2-30}$ alkynyl, an optionally substituted C$_{3-10}$ cycloalkenyl, an optionally substituted aryl(alkyl), an optionally substituted heteroaryl(alkyl), an optionally substituted heterocyclyl(alkyl), an optionally substituted acyl, an optionally substituted thiocarbonyl, an optionally substituted O-carbamyl, an optionally substituted N-carbamyl, an optionally substituted O-thiocarbamyl, an optionally substituted N-thiocarbamyl, an optionally substituted C-thioamido, an optionally substituted N-thioamido, an optionally substituted sulfenyl, an optionally substituted sulfinyl, an optionally substituted sulfonyl, an optionally substituted haloalkoxy, and a first boron-containing moiety, wherein the first boron-containing moiety is connected by the boron;

wherein the first boron-containing moiety is selected from the group consisting of an organoborane, a boronic ester, a boronic acid, a trifluoroborate salt, an N-coordinated boronate, a boronate and a boronamide;

wherein $X^1$ is selected from the group consisting of a —C(=O)Y, and a second boron-containing moiety;

wherein the second boron-containing moiety is selected from the group consisting of an organoborane, a boronic ester, a boronic acid, a trifluoroborate salt, an N-coordinated boronate, a boronate and a boronamide, wherein the second boron-containing moiety is connected by the boron;

wherein the compound of Formula (B) has the structure $R^2-X^2$;

wherein $R^2$ is selected from the group consisting of an optionally substituted $C_{1-30}$ alkyl, an optionally substituted $C_{2-30}$ alkenyl, an optionally substituted $C_{3-10}$ cycloalkyl, an optionally substituted $C_{3-10}$ cycloalkenyl, an optionally substituted aryl, an optionally substituted heteroaryl and an optionally substituted heterocyclyl;

wherein $X^2$ is selected from the group consisting of a halide, a pseudohalide, a —C(=O)Y, a zinc halide, a zinc pseudohalide, a magnesium halide, a magnesium pseudohalide and a third boron-containing moiety selected from the group consisting of an organoborane, a boronic ester, a boronic acid, a trifluoroborate salt, an N-coordinated boronate, a boronate and a boronamide;

wherein the first transition metal catalyst is selected from the group consisting of a Pd catalyst and a Ni catalyst;

wherein the second transition metal catalyst is selected from the group consisting of an Ir catalyst, a Cu catalyst and an Ru catalyst;

wherein the compound of Formula (I) has the structure:

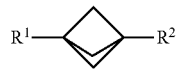

(I)

wherein the bond between $R^2$ and the bicyclo[1.1.1]pentane in the compound of Formula (I) is a carbon-carbon bond;

wherein each Y is independently selected from the group consisting of a halide, an optionally substituted heterocyclyl, an optionally substituted heteroaryl, $SR^6$, $OR^6$, SM and OM;

wherein each $R^6$ is independently selected from the group consisting of a hydrogen, an optionally substituted $C_{1-30}$ alkyl, an optionally substituted $C_{2-30}$ alkenyl, an optionally substituted $C_{3-30}$ cycloalkyl, an optionally substituted heterocyclyl, an optionally substituted heteroaryl, and an optionally substituted aryl; and wherein each M is independently selected from the group consisting of a monovalent cation and a divalent cation; provided that at least one of $X^1$ and $X^2$ is not a boron-containing moiety; and provided that when the second transition metal catalyst is present, either $X^1$ or $X^2$ is a —C(=O)Y.

2. The method of claim 1, wherein the first transition metal catalyst is selected to undergo oxidative addition to the compound of Formula (A) or the compound of Formula (B).

3. The method of claim 2, wherein the first transition metal catalyst is a Pd catalyst comprising a Pd atom.

4. The method of claim 2, wherein the first transition metal catalyst is a Ni catalyst comprising a Ni atom.

5. The method of claim 1, wherein the first transition catalyst is selected from the group consisting of $PdCl_2$, $Pd(ACN)_2Cl_2$, Pd(benzonitrile)$_2Cl_2$, Pd(1,5-COD)Cl$_2$, allylpalladium chloride dimer, Pd(dba)$_2$, Pd$_2$(dba)$_3$, Pd(OAc)$_2$, Pd(AmPhos)$_2$, Pd(P(tBu)$_3$)$_2$, Pd(AmPhos)$_2Cl_2$, Pd(P(o-tolyl)$_3$)$_2$, Pd(PPh$_3$)$_4$, Pd(QPhos)$_2$, PdCl$_2$(dtbpf), Pd(PCy$_3$)$_2$, bis(di-t-butyl-phenylphosphine)Pd(Cl)$_2$, PdCl$_2$(PPh$_3$)$_4$, PdCl$_2$(dppf), Chloro {2-[1-(N-methoxy)iminoethyl]phenyl}{[1,3-bis(2,6-di-i-propylphenyl]imidzole-2-ylidene}palladium(II), Chloro {2-[(1-(N-phenyl)iminoethyl [phenyl]{[1,3-bis(2,6-di-i-propylphenyl]imidzole-2-ylidene}palladium(II), Methanesulfonato(1,1-bis(di-t-butylphosphino)ferrocene)(2'-amino-1,1'-biphenyl-2-yl)palladium(II), Methanesulfonato(2-di-t-butylphosphino-3,4,5,6-tetramethyl-2',4',6'-tri-i-propylbiphenyl)(2'-amino-1,1'-biphenyl-2-yl)palladium(II), Allyl(cyclopentadienyl)palladium(II), Methanesulfonato(2-di-t-butylphosphino-1,1'-binaphthyl)(2'-amino-1,1'-biphenyl-2-yl)palladium(II), Di-MU-iodobis(tri-t-butylphosphino)dipalladium(I), Methanesulfonato[2-diethylphosphino-2',6'-bis(dimethylamino)-1,1-biphenyl](2'-amino-1,1'-biphenyl-2-yl)palladium(II), Acetato(2'-di-t-butylphosphino-1,1'-biphenyl-2-yl)palladium(II), Acetato(2,9-dimethyl-1,10-phenanthroline)palladium(II) dimer bis(trifluoromethanesulfonate), Allylchloro[1,3-bis(2,6-di-i-propylphenyl)-4,5-dihydroimidazol-2-ylidene]palladium(II), Allylchloro[1,3-bis(2,6-di-i-propylphenyl)imidazol-2-ylidene]palladium(II), Allylchloro[1,3-bis(2,4,6-trimethylphenyl)imidazol-2-ylidene]palladium(II), trans-Bis(dicyclohexylamine)bis(acetato)palladium(II), Bis {[4-(N,N-dimethylamino)phenyl]di-t-butylphosphino}palladium(0), N,N'-[Bis(2,6-dimethylphenyl)-1,3-dimethyl-1,3-propanediylidene](methyl)(triethylphosphine)palladium(II), [1,3-Bis(2,6-di-i-propylphenyl)-4,5-dihydroimidazol-2-ylidene]{2-[(dimethylamino-kN)methyl]phenyl-kC}(pyridine) palladium(II) tetrafluoroborate, 1,3-Bis(2,6-di-i-propylphenyl)imidazol-2-ylidene(1,4-naphthoquinone) palladium(0), [P,P'-1,3-Bis(di-i-propylphosphino)propane][P-1,3-bis(di-i-propylphosphino)propane]palladium(0), 1,2-Bis(phenylsulfinyl)ethanepalladium(II) acetate, Bis(tri-t-butylphosphine)palladium(0), [1,3-Bis(2,4,6-trimethylphenyl)-4,5-dihydroimidazol-2-ylidene]{2-[(dimethylamino-kN)methyl]phenyl-kC}(pyridine) palladium (II) tetrafluoroborate, 1,3-Bis(2,4,6-trimethylphenyl)imidazol-2-ylidene(1,4-naphthoquinone) palladium(0) dimer, Bis(tri-o-tolylphosphine)palladium(0), Chloro(1-t-butylindenyl) [1,3-bis(2,6-di-i-propylphenyl) imidazol-2-yl]palladium(II), Chloro(1-t-butylindenyl)[2-(dicyclohexylphosphino)-2',6'-dimethoxy-1,1'-biphenyl] palladium(II), Chloro(1-t-butylindenyl) [2-(dicyclohexylphosphino)-2',6'-di-i-propoxy-1,1'-biphenyl] palladium(II), Chloro(1-t-butylindenyl) [2-(dicyclohexylphosphino)-2',4',6'-tri-i-propyl-1,1'-biphenyl] palladium(II), Chloro(1-t-butylindenyl)palladium(II) dimer, Chloro(2-di-t-butylphosphino-2',4',6'-tri-i-propyl-1,1'-biphenyl) [2-(2-aminoethyl)phenyl]palladium(II), Chloro(2-dicyclohexylphosphino-2',6'-dimethoxy-1,1'-biphenyl)(2'-amino-1,1'-biphenyl-2-yl)palladium(II), Chloro(2- dicyclohexylphosphino-2',6'-dimethoxy-1,1'-biphenyl)[2-(2-aminoethylphenyl)]palladium(II), Chloro(2-dicyclohexylphosphino-3,6-dimethoxy-2',4',6'-tri-i-propyl-1,1'-biphenyl)(2'-amino-1,1'-biphenyl-2-yl)palladium(II), Chloro[2-(dicyclohexylphosphino)-3,6-dimethoxy-2',4',6'-tri-i-propyl-1,1'-biphenyl][2-(2-aminoethyl)phenyl]palladium(II), Chloro[2-(dicyclohexylphosphino)-2'-(N,N-dimethylamino)-1,1'-biphenyl[(2'-amino-1,1'-biphenyl-2-yl)palladium(II), Chloro(2-dicyclohexylphosphino-2',6'-di-i-propoxy-1,1'-biphenyl)(2'-amino-1,1'-biphenyl-2-yl)palladium(II), Chloro(2-dicyclohexylphosphino-2',6'-di-i-propoxy-1,1'-biphenyl) [2-(2-aminoethylphenyl)]palladium(II), Chloro(2-dicyclohexylphosphino-2',4',6'-tri-i-propyl-1,1'-biphenyl)(2'-amino-1,1'-biphenyl-2-yl) palladium(II), Chloro(2-dicyclohexylphosphino-2',4',6'-tri-i-propyl-1,1'-biphenyl)[2-(2-aminoethyl)phenyl]palladium(II), Chloro{[4-(N,N-dimethylamino)phenyl]di-t-butylphosphino}(2'-amino-1,1'-biphenyl-2-yl)palladium(II), Chloro[9,9-dimethyl-4,5-bis(diphenylphosphino)xanthene][2'-amino-1,1'-biphenyl]palladium(II), Chloro(di-2-norbornylphosphino)(2'-dimethylamino-1,1'-biphenyl-2-yl)palladium(II), Chloro(di-2-norbornylphosphino)(2-dimethylaminomethylferrocen-1-yl)palladium(II), Chloro[(1,2,3-η)-1-phenyl-2-propen-1-yl]-{[1,3-bis[2,6-bis(diphenylmethyl)-4-methylphenyl]-2H-imidazol-2-ylidene}palladium(II), Chloro[(1,2,3-η)-3-phenyl-2-propenyl][1,3-bis(2,6-di-i-propylphenyl)-4,5-dihydroimidazol-2-ylidene]palladium(II), Chloro[(1,2,3-η)-3-phenyl-2-propenyl][1,3-bis(2,6-di-i-propylphenyl)imidazol-2-ylidene]palladium(II), Chloro(tri-t-butylphosphine)(2'-amino-1,1'-biphenyl-2-yl)palladium(II), Diacetato[1,3-bis(diphenylphosphino)propane]palladium(II), trans-Di(μ-acetato)bis[o-(di-o-tolylphosphino)benzyl]dipalladium(II), Di-μ-bromobis(tri-t-butylphosphino)dipalladium(I), Dichlorobis(acetonitrile)palladium(II), Dichlorobis(benzonitrile)palladium(II), Dichlorobis(di-t-butylphenylphosphino)palladium(II), Dichloro[1,1'-bis(dicyclohexylphosphino)ferrocene]palladium(II), Dichloro[(R)-(+)-2,2'-bis(di-2-furanylphosphino)-6,6'-dimethoxy-1,1'-biphenyl]palladium(II), Dichlorobis{[4-(N,N-dimethylamino)phenyl]di-t-butylphosphino}palladium(II), Dichloro[(R)-(+)-2,2'-bis(diphenylphosphino)-1,1'-binaphthyl]palladium(II), Dichloro[(S)-(−)-2,2'-bis(diphenylphosphino)-1,1'-binaphthyl]palladium(II), Dichloro[1,4-bis(diphenylphosphino)butane]palladium(II), Dichloro[1,1'-bis(diphenylphosphino)ferrocene]palladium(II), Dichloro{bis[2-(diphenylphosphino)phenyl]ether}palladium(II), Dichloro[1,1'-bis(di-i-propylphosphino)ferrocene]palladium(II), trans-Dichlorobis(triphenylphosphine)palladium(II), Dichloro(di-μ-chloro)bis[1,3-bis(2,6-di-i-propylphenyl)imidazol-2-ylidene]dipalladium(II), Dichloro[9,9-dimethyl-4,5-bis(diphenylphosphino)xanthene]palladium(II), Dichloro(norbornadiene)palladium(II), Methanesulfonato[2,2'-bis(diphenylphosphino)-1,1'-binaphthyl](2'-amino-1,1'-biphenyl-2-yl)palladium(II), Methanesulfonato[1,1'-bis(diphenylphosphino)ferrocene)](2'-amino-1,1'-biphenyl-2-yl)palladium(II), Methanesulfonato[4,6-bis(diphenylphosphino)phenoxazine](2'-amino-1,1'-biphenyl-2-yl)palladium(II), Methanesulfonato[2-bis(3,5-di(trifluoromethyl)phenylphosphino)-3,6-dimethoxy-2',4',6'-tri-i-propyl-1,1'-biphenyl](2'-amino-1,1'-biphenyl-2-yl)palladium(II), Methanesulfonato(diadamantyl-n-butylphosphino)-2'-amino-1,1'-biphenyl-2-yl)palladium(II), Methanesulfonato[2-(di-1-adamantylphosphino)-3,6-dimethoxy-2',4',6'-tri-i-propyl-1,1'-biphenyl](2'-amino-1,1'-biphenyl-2-yl)palladium(II), Methanesulfonato[di-t-butyl(n-butyl)phosphine](2'-amino-1,1'-biphenyl-2-yl)palladium(II), Methanesulfonato(di-t-butylneopentylphosphine)(2'-amino-1,1'-biphenyl-2-yl)palladium(II), Methanesulfonato[2-(di-t-butylphosphino)-2'-(N,N-dimethylamino)-1,1'-biphenyl](2'-amino-1,1'-biphenyl-2-yl)palladium(II), Methanesulfonato(2-(di-t-butylphosphino)-3,6-dimethoxy-2',4',6'-tri-i-propyl-1,1'-biphenyl)(2'-amino-1,1'-biphenyl-2-yl)palladium(II), Methanesulfonato(2-(di-t-butylphosphino)-3-methoxy-6-methyl-2',4',6'-tri-i-propyl-1,1'-biphenyl)(2'-amino-1,1'-biphenyl-2-yl)palladium(II), Methanesulfonato(2-di-t-butylphosphino-2',4',6'-tri-i-propyl-1,1'-biphenyl)(2'-amino-1,1'-biphenyl-2-yl)palladium(II), Methanesulfonato(2-di-t-butylphosphino-2',4',6'-tri-i-propyl-1,1'-biphenyl)(2'-methylamino-1,1'-biphenyl-2-yl)palladium(II), Methanesulfonato(2-dicyclohexylphosphino-2',6'-bis(dimethylamino)-1,1'-biphenyl)(2'-amino-1,1'-biphenyl-2-yl)palladium(II), Methanesulfonato(2-dicyclohexylphosphino-2',6'-dimethoxy-1,1'-biphenyl)(2'-amino-1,1'-biphenyl-2-yl)palladium(II), Methanesulfonato(2-dicyclohexylphosphino-2',6'-dimethoxy-1,1'-biphenyl)(2'-methylamino-1,1'-biphenyl-2-yl)palladium(II), Methanesulfonato(2-dicyclohexylphosphino-3,6-dimethoxy-2',4',6'-tri-i-propyl-1,1'-biphenyl)(2'-amino-1,1'-biphenyl-2-yl)palladium(II), Methanesulfonato(2-dicyclohexylphosphino-3,6-dimethoxy-2',4',6'-tri-i-propyl-1,1'-biphenyl)(2'-methylamino-1,1'-biphenyl-2-yl)palladium(II), Methanesulfonato[2-(dicyclohexylphosphino)-2'-(N,N-dimethylamino)-1,1'-biphenyl](2'-amino-1,1'-biphenyl-2-yl)palladium(II), Methanesulfonato(2-dicyclohexylphosphino-2',6'-di-i-propoxy-1,1'-biphenyl)(2'-amino-1,1'-biphenyl-2-yl)palladium(II), Methanesulfonato(2-dicyclohexylphosphino-2',6'-di-i-propoxy-1,1'-biphenyl)(2'-methylamino-1,1'-biphenyl-2-yl)palladium(II), Methanesulfonato{(R)-(−)-1-[(S)-2-(dicyclohexylphosphino)ferrocenyl]ethyldi-t-butylphosphine}(2'-amino-1,1'-biphenyl-2-yl)palladium(II), Methanesulfonato(2-dicyclohexylphosphino-2',4',6'-tri-i-propyl-1,1'-biphenyl)(2'-amino-1,1'-biphenyl-2-yl)palladium(II), Methanesulfonato(2-dicyclohexylphosphino-2',4',6'-tri-i-propyl-1,1'-biphenyl)(2'-methylamino-1,1'-biphenyl-2-yl)palladium(II), Methanesulfonato{[4-(N,N-dimethylamino)phenyl]di-t-butylphosphino}(2'-amino-1,1'-biphenyl-2-yl)palladium(II), Methanesulfonato[9,9-dimethyl-4,5-bis(diphenylphosphino)xanthene][2'-amino-1,1'-biphenyl]palladium(II), Methanesulfonato[9,9-dimethyl-4,5-bis(diphenylphosphino)xanthene](2'-methylamino-1,1'-biphenyl-2-yl)palladium(II), Methanesulfonato(tri-t-butylphosphino)(2'-amino-1,1'-biphenyl-2-yl)palladium(II), Methanesulfonato(tri-t-butylphosphino)(2'-methylamino-1,1'-biphenyl-2-yl)palladium(II), Methanesulfonato(tricyclohexylphosphine)(2'-amino-1,1'-biphenyl-2-yl)palladium(II), Methanesulfonato(tricyclohexylphosphino)(2'-methylamino-1,1'-biphenyl-2-yl)palladium(II), (2'-Methylamino-1,1'-biphenyl-2-yl)methanesulfonatopalladium(II) dimer, Tris{tris[3,5-bis(trifluoromethyl)phenyl]phosphine}palladium(0), chloro($\eta^2$-P,C-tris(2,4-di-tert-butylphenyl)phosphite)(tricyclohexylphosphine)palladium(II), 2-(2'-di-tert-butylphosphine)biphenylpalladium(II) acetate, di-μ-chlorobis[5-chloro-2-[(4-chlorophenyl)(hydroxyimino-kN)methyl]phenyl-kC]palladium dimer, di-μ-chlorobis[5-hydroxy-2-[1-(hydroxyimino-kN)ethyl]phenyl-KC]palladium(II) dimer, dicyclohexyl[9-(3-phenylpropyl)-9-fluorenyl]phosphonium tetrafluoroborate, dicyclohexyl-{2-sulfo-9-[3-(4-sulfo-phenyl)propyl]-9-fluorenyl}phosphonium-hydrogensulfate, 2'-(dimethylamino)-2-biphenylyl-palladium(II) chloride dinorbornylphosphine complex, 2-(dimethylaminomethyl)ferrocen-1-yl-palladium(II) chloride dinorbornylphosphine, a cyclopalladated 2-aminobiphenylmesylate, a Bedford catalyst, a Nájera catalyst, a Pd nanoparticle catalyst, NiCl$_2$(dtbpy), chloro(2-methylphenyl)bis(triphenylphosphine)nickel(II), [1,2-bis(diphenylphosphino)ethane]dichloronickel(II), Ni(acac)$_2$, NiCl$_2$(PCy$_3$)$_2$, Ni(1,5-COD)$_2$, NiCl$_2$dimethoxyethane, NiCl$_2$-glyme, NiCl$_2$, NiCl$_2$(dppf), NiCl$_2$(dppe), Bis(cyclopentadienyl)nickel(II), 2,3-Bis(2,6-diisopropylphenylimino)butane nickel(II) dibromide, Bis[(2-dimethylamino)phenyl]amine nickel(II) chloride, Bis(isopropylcyclopentadienyl)nickel, Bis(methylcyclopentadienyl)nickel(II), N,N'-Bis(salicylidene)ethylenediaminonickel(II), Bis(triphenylphosphine)nickel(II) dichloride, Chloro(cyclopentadienyl)(triphenylphosphine)nickel(II), Chloro(ethylcyclopentadienyl)(triphenylphosphinenickel(II), Chloro(2-methylphenyl)bis(triphenylphosphine)nickel(II), Chloro(1-naphthyl)bis(triphenylphosphine)nickel(II), Dibromobis(tributylphosphine)nickel(II), Dibromobis(triphenylphosphine)nickel(II), Dichlorobis(tributylphosphine)nickel(II), Dichlorobis(trimethylphosphine)nickel(II), methallylnickel chloride dimer, Hexamminenickel(II) bromide, Nickel(II) acetate, Nickel(II) acetylacetonate, Nickel(II) bis(trifluoromethanesulfonimide), Nickel(II) bromide, Nickel(II) hexafluoroacetylacetonate, Nickel(II) trifluoromethanesulfonate, Tetrakis(triphenylphosphite)nickel(0), Trovitch Ni-Precatalyst and NiCl$_2$(dppp).

6. The method of claim 1, wherein the second transition metal catalyst is a Ru catalyst comprising a Ru atom.

7. The method of claim 1, wherein the second transition metal catalyst is an Ir catalyst comprising an Ir atom.

8. The method of claim 1, wherein the second transition metal catalyst is selected from the group consisting of Ru(bpy)$_3$Cl$_2$, Ru(bpm)$_3$(PF$_6$)$_2$, Ru(bpz)$_3$(PF$_6$)$_2$, Ru(bpy)$_3$(PF$_6$)$_2$ Ru(menbpy)$_3$(PF$_6$)$_2$ Ru(bpm)$_3$(PF$_6$)$_2$, Ru(phen)$_3$(PF$_6$)$_2$Ir[dF(CF$_3$)ppy]$_2$(bpy)PF$_6$, Ir[dF(Me)ppy]$_2$(dtbpy)PF$_6$, Ir[dF(CF$_3$)ppy]$_2$(dtbpy)PF$_6$, Ir(ppy)$_2$(dtbpy)PF$_6$, Ir(ppy)$_3$, Ir[p-F(t-Bu)ppy]$_3$, Ir(dFppy)$_3$ and Ir(Fppy)$_3$.

9. The method of claim 1, wherein the second transition metal catalyst is a Cu catalyst comprising a Cu atom.

10. The method of claim 2, wherein the compound of Formula (A) has the structure:

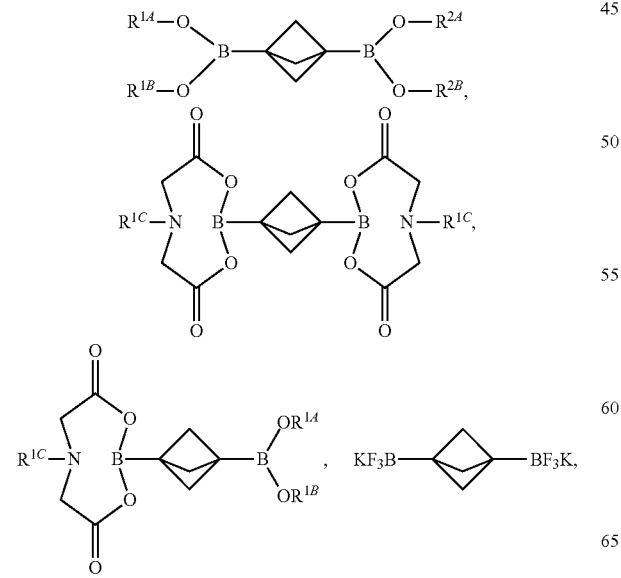

-continued

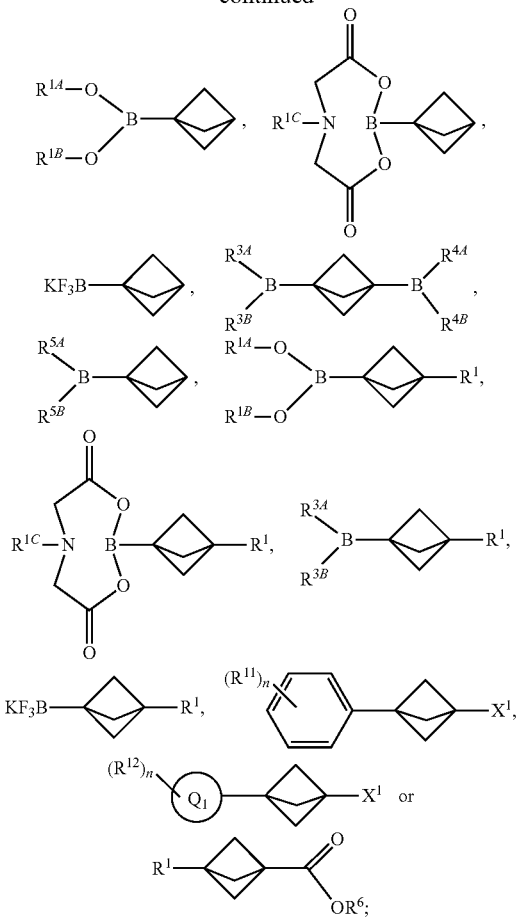

wherein:
R$^{1A}$ and R$^{1B}$ are each independently hydrogen, an optionally substituted C$_{1-30}$ alkyl or an optionally substituted C$_{3-10}$ cycloalkyl, or OR$^{1A}$, OR$^{1B}$ and the boron atom to which they attach are taken together to form an optionally substituted heterocyclyl;

each R$^{1C}$ is independently hydrogen, an optionally substituted C$_{1-30}$ alkyl or an optionally substituted C$_{3-10}$ cycloalkyl;

R$^{2A}$ and R$^{2B}$ are each independently hydrogen or an optionally substituted C$_{1-30}$ alkyl, or OR$^{2A}$, OR$^{2B}$ and the boron atom to which they attach can be taken together to form an optionally substituted heterocyclyl;

R$^{3A}$ and R$^{3B}$ are each independently an optionally substituted C$_{1-30}$ alkyl, an optionally substituted C$_{3-10}$ cycloalkyl, an amine, an arylamine, or an alkylamine, or R$^{3A}$, R$^{3B}$ and the boron atom to which they attach are taken together to form an optionally substituted heterocyclyl;

R$^{4A}$ and R$^{4B}$ are each independently an optionally substituted C$_{1-30}$ alkyl, an optionally substituted C$_{3-10}$ cycloalkyl, an amine, an arylamine, or an alkylamine, or R$^{4A}$, R$^{4B}$ and the boron atom to which they attach are taken together to form an optionally substituted heterocyclyl; and R$^{5A}$ and R$^{5B}$ are each independently an optionally substituted C$_{1-30}$ alkyl, an optionally substituted C$_{3-10}$ cycloalkyl, an amine, an arylamine, or an alkylamine, or $R^{5A}$, $R^{5B}$ and the boron atom to which they attach are taken together to form an optionally substituted heterocyclyl;

$Q_1$ is an optionally substituted monocyclic or bicyclic heteroaryl or an optionally substituted monocyclic or bicyclic heterocyclyl including 0 to 4 heteroatom moieties selected from —N=, —N($R^{2B}$)—,

—O— and —S—;

wherein each $R^{2B}$ is selected from the group consisting of D (deuterium), hydroxy, $C_{1-4}$ alkoxy, $C_{1-4}$ alkyl, $C_{3-10}$ cycloalkyl, aryl, heteroaryl, $C_{1-6}$ haloalkyl, alkenyl, alkynyl, cycloalkenyl, aryl(alkyl), heteroaryl(alkyl), heterocyclyl(alkyl), acyl, sulfenyl, sulfinyl, sulfonyl, an amino, a mono-substituted amino group or a di-substituted amino group;

each $R^{11}$ and each $R^{12}$ is independently selected from the group consisting of D (deuterium), halogen, hydroxy, $C_{1-4}$ alkoxy, $C_{1-4}$ alkyl, $C_{3-10}$ cycloalkyl, an optionally substituted $C_{3-10}$ cycloalkenyl, aryl, heteroaryl, $C_{1-6}$ haloalkyl, cyano, alkenyl, alkynyl, cycloalkenyl, aryl (alkyl), heteroaryl(alkyl), heterocyclyl(alkyl), acyl, thiocarbonyl, O-carbamyl, N-carbamyl, O-thiocarbamyl, N-thiocarbamyl, C-amido, N-amido, C-thioamido, N-thioamido, S-sulfonamido, N-sulfonamido, C-carboxy, O-carboxy, sulfenyl, sulfinyl, sulfonyl, haloalkoxy, an amino, a mono-substituted amino group or a di-substituted amino group; and each n is independently an integer from 0 to 4.

11. The method of claim 2, wherein the compound of Formula (A) is selected from the group consisting of:

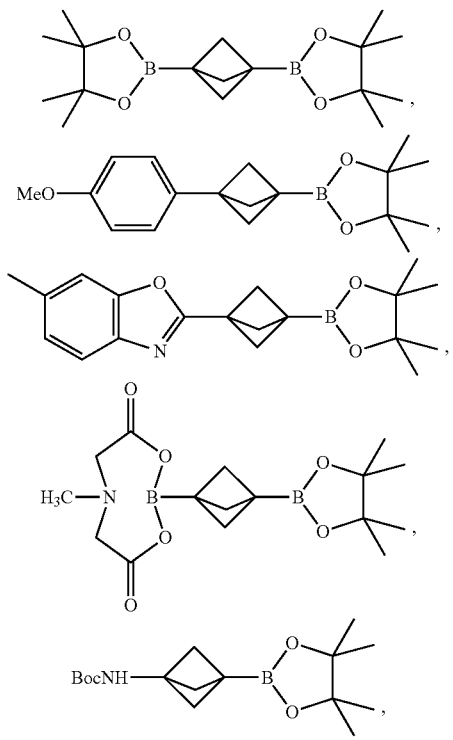

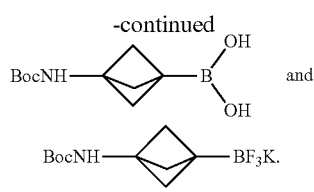

12. The method of claim 1, wherein said reacting is in the presence of a ligand.

13. The method of claim 12, wherein the ligand is selected from the group consisting of A-caPhos, a-taPhos, Binap, BIPHEP, BippyPhos, Ad-BrettPhos, ditBuBrettPhos, BrettPhos, CataCXcium POMeCy, CataCXcium PtB, CataCXium PiCy, CataCXium FBn, CataCXium PCy, CataCXium PInCy, CataCXium POMetB, CataXCium A, CataXCium ABn, CataXCium AHI, CataXCium C, CataXCium FBu, CataXCium FPrPh, CataXCium FSulf, CataXCium PIntB, CPhos, Cy-BIPHEP, Cy-BippyPhos, Cy-JohnPhos, Cy-PhenCarPhos, DavePhos, DCEPhos, DCyPF, DiPPF, di-tBu-neopentylPhosphonium $HBF_4$, DPEPhos, DPPBz, DPPE, DPPF, DtBPF, DTP-DPEPhos, JackiePhos, JohnPhos, Me4XPhos, Me4t-BuXPhos, MeDalPhos, MePhos, MorDalPhos, N-dicyclohexylphosphino-2-(2'-methylphenyl)-1H-indole, XantPhos, $PCy_3$ $HBF_4$, P(o-OMePh)$_3$, $PPh_3$, $PtBu_3$ $HBF_4$, $PXy_3$, QPhos, PhDavePhos, RockPhos, RuPhos, SL-J003-1, SL-J009-1, SPhos, SPhos-$SO_3Na$, SymPhos, tBuBiNap, tBuDavePhos, tBuMePhos, tBuXantPhos, tBuXPhos, TrixiePhos, XantPhos, XPhos, XPhos-$SO_3Na$, $Me_3P$ $HBF_4$, $Et_3P$ $HBF_4$, xylBinap, CycBRIDP, AmindolePhos, NPCy o-Andole-Phos, NPCy Phendole-Phos, cBRIDP, vBRIDP, CyvBRIDP, CM-Phos, KitPhos, 4,4'-di-tert-butyl-2,2'-dipyridyl, 2,2'-bipyridyl, 4,4'-dimethoxy-2,2'-bipyridyl, 2,2'-biquinoline, bathophenanthroline, s-BuPyBox, neocuproine, trans-2-aminocyclohexanol, and combinations thereof.

14. The method of claim 1, wherein said reacting is in the presence of a precatalyst.

15. The method of claim 14, wherein the precatalyst is selected from the group consisting of XantPhos 3rd gen, tBuXPhos 3rd gen, CPhos 3rd gen, APhos 3rd gen, phosphaadamantane 3rd gen, XPhos 3rd gen, RuPhos 3rd gen, JackiePhos 3rd gen, 1st gen BrettPhos, 1st gen ditBuXPhos, 1st gen RuPhos, 1st gen SPhos, 1st gen XPhos, 2nd gen RuPhos, 2nd gen SPhos, 2nd gen XPhos, OMs Pd Dimer, and combinations thereof.

16. The method of claim 1, wherein the base is selected from the group consisting of a metal hydroxide base, a metal carbonate base, a metal bicarbonate base, an amine base, a metal fluoride base, a metal alkoxide base, a metal carboxylate base and a metal phosphate base.

17. The method of claim 16, wherein the base is selected from the group consisting of $Et_3N$, Hunig's base, pyridine, piperidine, morpholine, 1,8-Bis(dimethylamino)naphthalene, DBU, $Na_2CO_3$, $K_2CO_3$, $Li_2CO_3$, $Cs_2CO_3$, KOtBu, $K_2HPO_4$, $Na_2HPO_4$, $Na_3PO_4$, $K_3PO_4$, NaOH, KOH, CsOH, LiOH, KF, CsF, NaOAc, KOAc, CsOAc, LiOAc, LiOtBu, NaOtBu, $NaHCO_3$, $KHCO_3$, $CsHCO_3$, and $LiHCO_3$.

18. The method of claim 1, wherein M is selected from the group consisting of $Li^+$, $Na^+$, $K^+$, $Rb^+$, $Cs^+$, a quaternary nitrogen, $Mg^{+2}$, $Ca^{+2}$, $Sr^{+2}$, and $Ba^{+2}$.

19. The method of claim 1, wherein said reacting is in the presence of visible light.

20. A compound selected from the group consisting of Formula (A1a), Formula (A1b), Formula (A1c) and Formula (A1d):

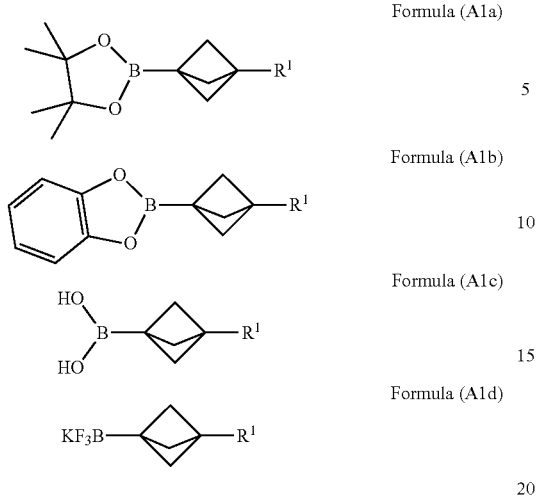

Formula (A1a)

Formula (A1b)

Formula (A1c)

Formula (A1d)

wherein $R^1$ is selected from the group consisting of an optionally substituted $C_{1-30}$ alkyl, an optionally substituted $C_{2-30}$ alkenyl, an optionally substituted $C_{3-10}$ monocyclic cycloalkyl, an optionally substituted aryl, an optionally substituted heteroaryl, an optionally substituted heterocyclyl, a halogen, an optionally substituted C-carboxy, an amino, a mono-substituted amino, a di-substituted amino, an optionally substituted C-amido, an optionally substituted N-amido, an optionally substituted $C_{1-30}$ alkoxy, a hydroxy, an optionally substituted $C_{1-30}$ haloalkyl, a cyano, an optionally substituted S-sulfonamido, an optionally substituted N-sulfonamido, an optionally substituted O-carboxy, an optionally substituted $C_{2-30}$ alkynyl, an optionally substituted $C_{3-10}$ cycloalkenyl, an optionally substituted aryl(alkyl), an optionally substituted heteroaryl(alkyl), an optionally substituted heterocyclyl(alkyl), an optionally substituted acyl, an optionally substituted thiocarbonyl, an optionally substituted O-carbamyl, an optionally substituted N-carbamyl, an optionally substituted O-thiocarbamyl, an optionally substituted N-thiocarbamyl, an optionally substituted C-thioamido, an optionally substituted N-thioamido, an optionally substituted sulfenyl, an optionally substituted sulfinyl, an optionally substituted sulfonyl, an optionally substituted haloalkoxy, and a first boron-containing moiety, wherein the first boron-containing moiety is connected by the boron.

21. The compound of claim 20 selected from the group consisting of:

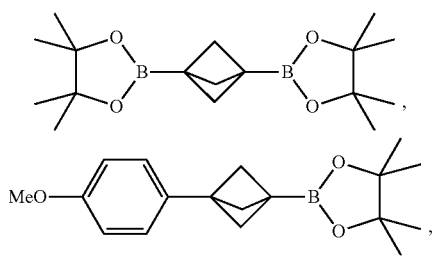

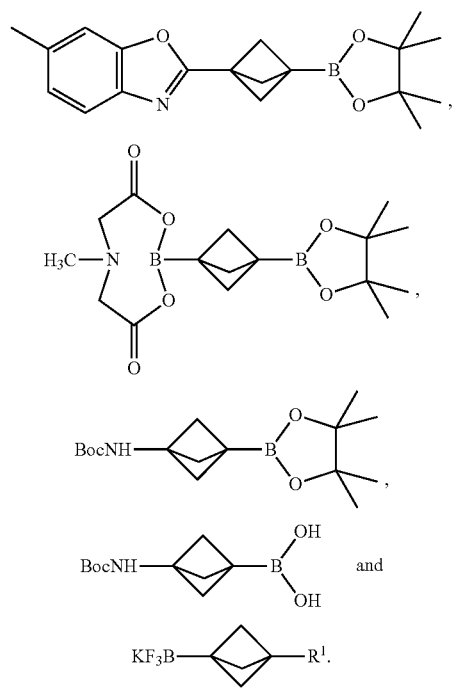

22. A compound selected from the group consisting of:

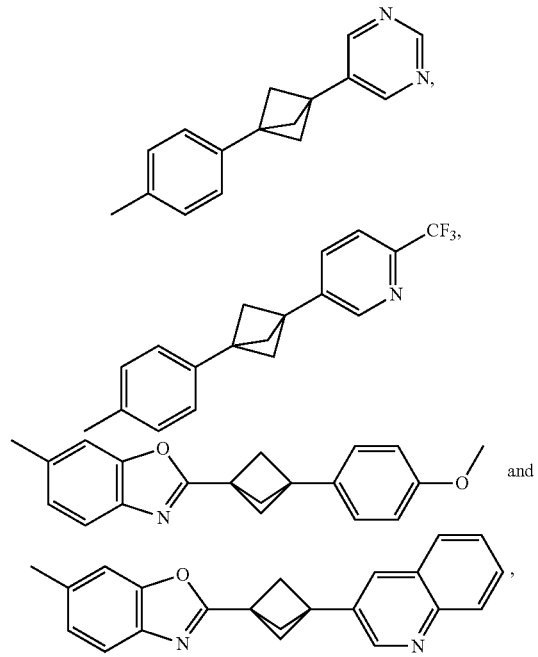

or a pharmaceutically acceptable salt of any of the foregoing.